United States Patent
Burke et al.

(10) Patent No.: US 10,370,393 B2
(45) Date of Patent: Aug. 6, 2019

(54) STEREORETENTIVE CROSS-COUPLING OF BORONIC ACIDS

(71) Applicant: The Board of Trustees of the University of Illinois, Urbana, IL (US)

(72) Inventors: Martin D. Burke, Champaign, IL (US); Ian Crouch, Urbana, IL (US); Jonathan Lehmann, Urbana, IL (US); Andrea Palazzolo, Urbana, IL (US); Claire Simons, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/959,986

(22) Filed: Apr. 23, 2018

(65) Prior Publication Data
US 2018/0305381 A1 Oct. 25, 2018

Related U.S. Application Data

(60) Provisional application No. 62/659,258, filed on Apr. 18, 2018, provisional application No. 62/488,332, filed on Apr. 21, 2017.

(51) Int. Cl.
| | |
|---|---|
| B01J 31/24 | (2006.01) |
| C07F 9/50 | (2006.01) |
| C07F 5/02 | (2006.01) |
| C07B 37/04 | (2006.01) |
| C07F 15/00 | (2006.01) |

(52) U.S. Cl.
CPC ......... *C07F 9/5022* (2013.01); *B01J 31/2404* (2013.01); *C07B 37/04* (2013.01); *C07F 5/025* (2013.01); *C07F 15/006* (2013.01); *C07F 15/0066* (2013.01); *B01J 2231/4277* (2013.01); *B01J 2531/824* (2013.01)

(58) Field of Classification Search
None
See application file for complete search history.

(56) References Cited

U.S. PATENT DOCUMENTS

| | | |
|---|---|---|
| 2009/0030238 A1 | 1/2009 | Burke et al. |
| 2010/0121062 A1 | 5/2010 | Burke et al. |
| 2011/0201806 A1 | 8/2011 | Burke et al. |
| 2012/0059184 A1 | 3/2012 | Burke et al. |
| 2013/0331585 A1 | 12/2013 | Duncton et al. |
| 2014/0094615 A1 | 4/2014 | Burke et al. |
| 2016/0280721 A1 | 9/2016 | Burke et al. |

FOREIGN PATENT DOCUMENTS

DE 4408500 * 9/1994

OTHER PUBLICATIONS

Kambe et al. Chem. Soc. Rev., 2011, 40, 4937-4947.*
Takeda et al. Heteroatom Chemistry, 2014, 25(6), 628-635.*
Hoang et al., "Enantioselective γ-borylation of Unsaturated Amides and Stereoretentive Suzuki-Miyaura Crosscoupling," Chem Sci., 8:4511-4516, Apr. 2017.
Imao et al., "Cross Coupling Reactions of Chiral Secondary Organoboronic Esters with Retention of Configuration," J. Am. Chem. Soc., 131(14):5024-5025, Mar. 2009.
Li et al., "Stereospecific Pd-Catalyzed Cross-Coupling Reactions of Secondary Alkylboron Nucleophiles and Aryl Chlorides," J. Am. Chem. Soc., 136(40):14027-14030, Sep. 2014.
Rygus et al., "Enantiospecific and Iterative Suzuki-Miyaura Cross-Couplings," J. Am. Chem. Soc., 139(50):18124-18137, Nov. 2017.
Sandrock et al., "Stereospecific Cross-Coupling of Secondary Alkyl β-Trifluoroboratoamides," J. Am. Chem. Soc., 132(48):17108-17110, Nov. 2010.
Thomas et al., "Structural, Kinetic, and Computational Characterization of the Elusive Arylpalladium(II)boronate Complexes in the Suzuki-Miyaura Reaction," J. Am. Chem. Soc., 139(10):3805-3821, Mar. 2017.

* cited by examiner

*Primary Examiner* — Ana Z Muresan
(74) *Attorney, Agent, or Firm* — Haukaas Fortius PLLC; Michael H. Haukaas

(57) ABSTRACT

The present disclosure provides tri-orthoalkylphenyl phosphine catalysts of formula I

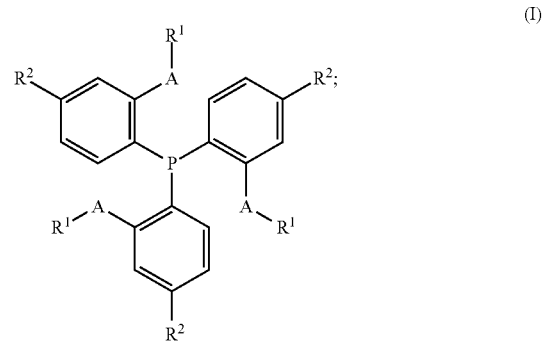

(I)

wherein A is CH2, C=O, or NR$^4$; R$^1$ is aryl, heteroaryl, isopropyl, tert-butyl, cycloalkyl, or heterocycloalkyl, wherein aryl, heteroaryl, cycloalkyl and heterocycloalkyl are optionally substituted; R$^2$ is H, (C$_1$-C$_8$) alkyl, (C$_1$-C$_8$)alkoxy, N(R$^4$)$_2$, or an electron withdrawing group; and each R$^4$ is independently H or (C$_1$-C$_8$) alkyl; that are tuned electrically and sterically.

7 Claims, 10 Drawing Sheets

STEREORETENTIVE CROSS-COUPLING OF BORONIC ACIDS

RELATED APPLICATIONS

This application claims priority under 35 U.S.C. § 119(e) to U.S. Provisional Patent Application Nos. 62/659,258 filed Apr. 18, 2018 and 62/488,332 filed Apr. 21, 2017, which applications are incorporated herein by reference.

GOVERNMENT SUPPORT

This invention was made with government support under Grant No. GM118185 awarded by the National Institutes of Health. The government has certain rights in the invention.

BACKGROUND OF THE INVENTION

The complex three-dimensional structures of $Csp^3$- and stereocenter-rich small molecules offer tremendous potential to serve transformative roles in society. For instance, there is a strong positive correlation between $Csp^3$ content and successful drug development. Natural products rich in $sp^3$ carbons and stereocenters also perform a plethora of remarkable, albeit frequently underutilized, functions. Understanding and harnessing the functional potential of these and many other natural products often requires synthetic access to the parent molecule and many structural derivatives, but due to their inherent complexity, the requisite time and labor to create customized total syntheses still remains a major bottleneck. To accelerate synthetic access to complex small molecules, we need to begin the transition away from the traditional approach of using highly customized routes featuring many different kinds of reactions towards a more generalized, rapid, and automatable synthesis platform.

Stereochemically-complex, $Csp^3$-rich small molecules can perform extraordinary functions, but accessing this potential often requires the time-consuming optimization of highly customized synthetic routes. The development of a more generalized building block-based synthesis strategy has the potential to substantially improve the efficiency and flexibility of small molecule synthesis. However, applying this approach to structurally complex small molecules requires highly precise $Csp^3$ coupling methods that form discrete products free of stereo- and regioisomers.

Lego-like assembly of pre-fabricated organoboronate building blocks has emerged as a promising strategy for generalizing and automating the synthesis of complex molecules (Burke and coworkers, *Science* 2015, 347 (6227), 1221-6). Already, this approach has accelerated synthetic access to many different types of compounds rich in $Csp^2$ carbons, including natural products, pharmaceuticals, biological probes, and materials components.

The problem is that the synthesis of stereochemically complex $Csp^3$-rich small molecules remains a highly customized, slow, and specialist-dependent process, and thus represents a major bottleneck in efforts to access the substantial untapped functional potential that this class of chemical matter possesses. Accordingly, there is a need for catalysts with specialized ligands that can efficiently, and cost effectively, catalyze the stereospecific formation of carbon-carbon bonds.

SUMMARY

Lego-like synthesis of $Csp^3$-rich small molecules would greatly improve access to their exceptional functional potential. But achieving this goal requires advanced $Csp^3$ cross-coupling methods with heightened stereocontrol. Although they proceed through stereospecific mechanisms, cross-couplings of secondary $Csp^3$ organoboronates yield mixtures of stereoisomers. This is attributable to energetically similar stereodivergent stereospecific pathways for retentive and invertive transmetalation. Because the latter should uniquely require association of the organoboronate above or below the square plane of a Pd(II) complex, we hypothesized that phosphine ligands which selectively shield these positions would promote stereoretentive $Csp^3$ cross-couplings. Here we report new phosphine ligands, for example, tri(2-benzyl-phenyl)phosphine, which enables the cross-coupling of unactivated secondary $Csp^3$ boronic acids with near perfect site- and stereoretention. X-ray studies and systematic electronic tuning of variably shielded phosphine [Pd(II)] complexes collectively support realization of this ligand design principle. This method enables the simple, Lego-like synthesis of complex $Csp^3$-rich natural products, and all of their $Csp^3$ stereoisomers, from off-the-shelf chiral building blocks.

Accordingly, this disclosure provides a phosphine compound of Formula I:

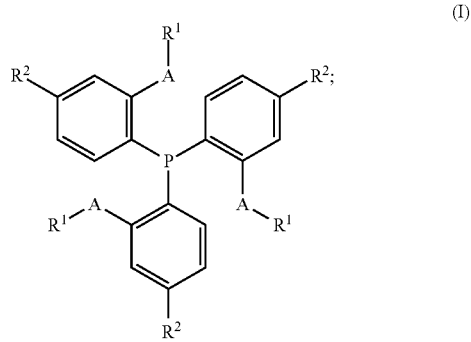

wherein
A is $CH_2$, $C=O$, $NR^4$, or O;
$R^1$ is aryl, heteroaryl, isopropyl, tert-butyl, cycloalkyl, or heterocycloalkyl, wherein aryl, heteroaryl, cycloalkyl and heterocycloalkyl are optionally substituted;
$R^2$ is H, $(C_1-C_8)$alkyl, $(C_1-C_8)$alkoxy, $N(R^4)_2$, or an electron withdrawing group; and
each $R^4$ is independently H or $(C_1-C_8)$alkyl.

This disclosure also provides a composition comprising a phosphine compound described above and a palladium catalyst.

In addition, this disclosure provides a method to form a stereoretentive carbon-carbon bond comprising:
a) combining a cross-coupling substrate, a secondary $Csp^3$ boronic acid, a palladium catalyst, and a phosphine compound of Formula I to form a reaction mixture; and
b) heating the reaction mixture;
thereby forming a cross-coupling product of the cross-coupling substrate and the boronic acid, wherein a stereoretentive carbon-carbon bond is formed in the cross-coupling product.

The invention provides novel compounds of Formulas I-III, intermediates for the synthesis of compounds of Formulas I-III, as well as methods of preparing compounds of Formulas I-III. The invention also provides compounds of Formulas I-III that are useful as intermediates for the synthesis of other useful compounds. The invention provides for the use of compounds of Formulas I-III for the manufacture of catalysts and compositions that are useful for organic synthesis.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION $Csp^3$-rich small molecules have exceptional functional potential. A correlation between $Csp^3$ content and successful development of new pharmaceuticals is now widely appreciated. Natural products, which tend to contain a relatively large percentage of $Csp^3$ centers, inspired more than half of all clinically approved drugs. And because each carbon atom can be a stereogenic center, the information density in $Csp^3$-rich molecules can far exceed that of their $Csp^2$-rich counterparts, making such compounds especially attractive for developing next generation probes, medicines, sensors, materials and nanotechnologies that perform higher-order molecular functions.

Figure 1:
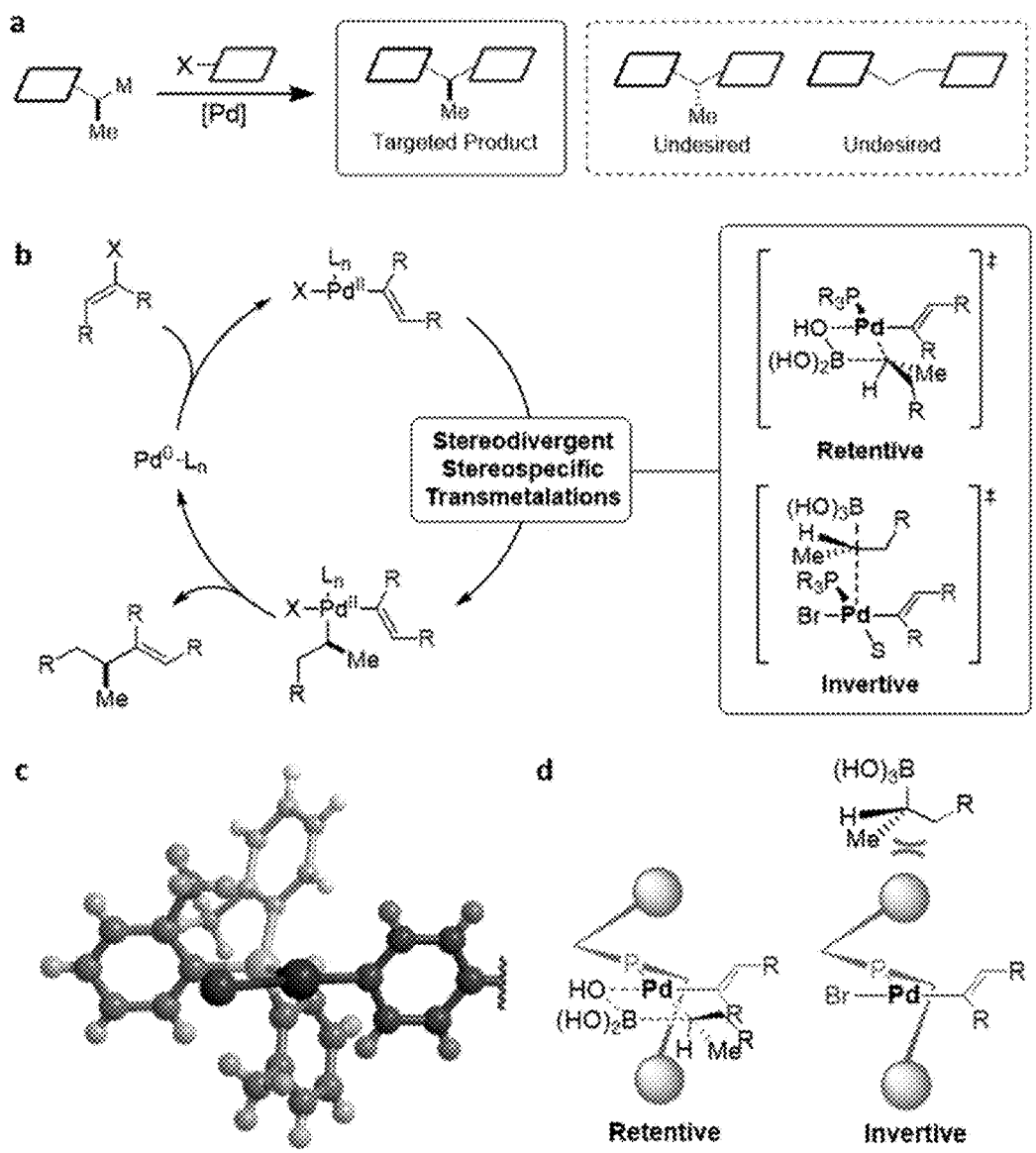
FIG. 1. Challenges to Pd-catalyzed Csp3 coupling. (A) Effect of [Pd] catalyst selectivity on product outcome. (B) A stereoisomeric product mixture can arise due to a competition between stereodivergent stereospecific transmetalation mechanisms. (C) orthosubstituted triarylphosphine ligands are capable of blocking the axial coordination sites on palladium, as can be seen in the crystal structure of $\{[(o\text{-}MeC_6H_4)_3P]Pd(4\text{-}nBuPh)(Br)\}_2$. (D) Blocking axial coordination sites with a "zig-zag"-shaped phosphine ligand could selectively inhibit the stereoinvertive transmetalation mechanism.

Progress toward efficient, flexible, and even automated Lego-like synthesis of $Csp^2$-rich small molecules from prefabricated organoboronate building blocks has recently been made. Expanding this approach to include a wide range of $Csp^3$-rich small molecules now represents a frontier objective. Achieving this requires the cross-coupling of $Csp^3$ boronate building blocks with outstanding levels of stereocontrol to avoid the formation of challenging-to-separate mixtures of isomeric products (FIG. 1a).

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, or two substituents on the phenyl ring.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983);

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

The term "alkyl" refers to a branched or unbranched hydrocarbon having, for example, from 1-20 carbon atoms, and often 1-12, 1-10, 1-8, 1-6, or 1-4 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, 3-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or (C$_1$-C$_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "enantiomerically enriched" ("ee") as used herein refers to mixtures that have one enantiomer present to a greater extent than another. Reactions that provide one enantiomer present to a greater extent than another would therefore be "enantiospecific" (or demonstrate "enantiospecificity"). In one embodiment of the invention, the term "enantiomerically enriched" refers to a mixture having at least about 2% ee; in another embodiment of the invention, the term "enantiomerically enriched" refers to a mixture having at least about 5% ee; in another embodiment of the invention, the term "enantiomerically enriched" refers to a mixture having at least about 20%; in another embodiment of the invention, the term "enantiomerically enriched" refers to a mixture having at least about 50%; in another embodiment of the invention, the term "enantiomerically enriched" refers to a mixture having at least about 80%; in another embodiment of the invention, the term "enantiomerically enriched" refers to a mixture having at least about 90%; in another embodiment of the invention, the term "enantiomerically enriched" refers to a mixture having at least about 95%; in another embodiment of the invention, the term "enantiomerically enriched" refers to a mixture having at least about 98%; in another embodiment of the invention, the term "enantiomerically enriched" refers to a mixture having at least about 99%. The term "enantiomerically enriched" includes enantiomerically pure mixtures which are mixtures that are substantially free of the species of the opposite optical activity or one enantiomer is present in very low quantities, for example, 0.01%, 0.001% or 0.0001%.

The term "organoboronic acid" or "boronic acid" means a compound represented by R*—B(OH), where R* is an organic group that is bonded to the boron through a boron-carbon bond.

The term "sp$^3$ hybridization" means that an atom is bonded and/or coordinated in a configuration having a tetrahedral character of at least 50%. For tetracoordinate boron atoms, the tetrahedral character of the boron atom is calculated by the method of Hopfl, H., *J. Organomet. Chem.* 1999, 581, 129-149.

The term "secondary Csp$^3$ boronic acid" refers to an asymmetric secondary carbon substituted with a boronic acid moiety (or boronate moiety). For example, CHR$^7$R$^8$R$^9$ wherein R$^7$ and R$^8$ are different substituents and R$^9$ is a boronic acid moiety (or boronate moiety).

Embodiments of the Invention

This disclosure provides various embodiments of a phosphine compound of Formula I:

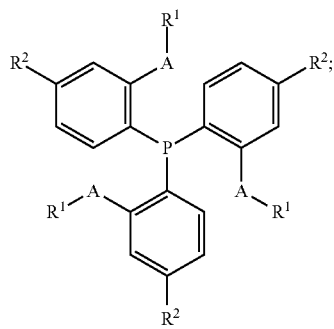

(I)

wherein

A is CH$_2$, C=O, NR$^A$, or O;

R$^1$ is aryl, heteroaryl, isopropyl, tert-butyl, cycloalkyl, or heterocycloalkyl, wherein aryl, heteroaryl, cycloalkyl and heterocycloalkyl are optionally substituted;

R$^2$ is H, (C$_1$-C$_8$)alkyl, (C$_1$-C$_8$)alkoxy, N(R$^A$)$_2$, or an electron withdrawing group; and each R$^A$ is independently H or (C$_1$-C$_8$)alkyl.

In some embodiments, R$^1$ is aryl or (C$_3$-C$_8$)cycloalkyl, wherein aryl and (C$_3$-C$_8$)cycloalkyl are optionally mono- or disubstituted. In other embodiments, the electron withdrawing group is halo, trifluoromethyl, pentafluoroethyl, trifluoromethoxy, nitrile, nitro, CO$_2$R$^A$, C(O)N(R$^A$)$_2$, SO$_2$R$^A$, SO$_2$N(R$^A$)$_2$, or P(O)[N(R$^A$)$_2$]$_2$.

In additional embodiments, the phosphine compound is a phosphine compound of Formula II:

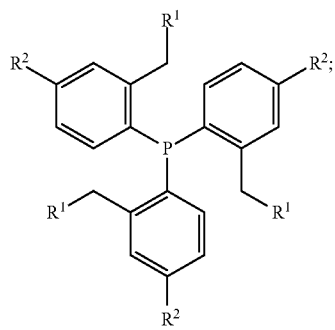

(II)

wherein

R$^1$ is phenyl or (C$_3$-C$_6$)cycloalkyl, wherein phenyl and (C$_3$-C$_6$)cycloalkyl are optionally mono- or disubstituted; and R$^2$ is H, (C$_1$-C$_5$)alkyl, (C$_1$-C$_5$)alkoxy, N(R$^A$)$_2$, halo, trifluoromethyl, pentafluoroethyl, trifluoromethoxy, nitrile, nitro, CO$_2$R$^A$, or C(O)N(R$^A$)$_2$.

In other embodiments, R$^2$ is H, halo, trifluoromethyl, pentafluoroethyl, trifluoromethoxy, nitrile, nitro, CO$_2$R$^A$, or C(O)N(R$^A$)$_2$.

In yet other additional embodiments, the phosphine compound is phosphine compound of Formula III:

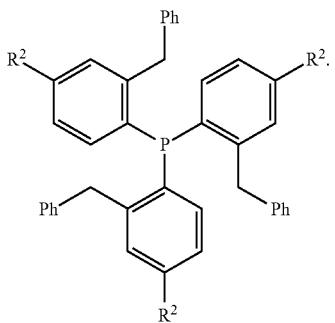

(III)

In various embodiments, R$^2$ is as described above for Formula II, or R$^2$ is H, methyl ethyl, methoxy, ethoxy, dimethylamine, diethylamine, halo, trifluoromethyl, pentafluoroethyl, trifluoromethoxy, nitrile, nitro, CO$_2$R$^A$, or C(O)N(R$^A$)$_2$.

In some embodiments, the phosphine compound is one of phosphine compounds IIIA-IIIC:

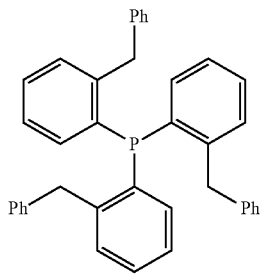

IIIA

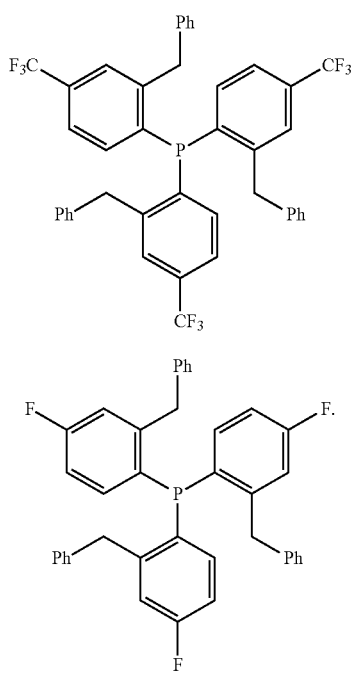

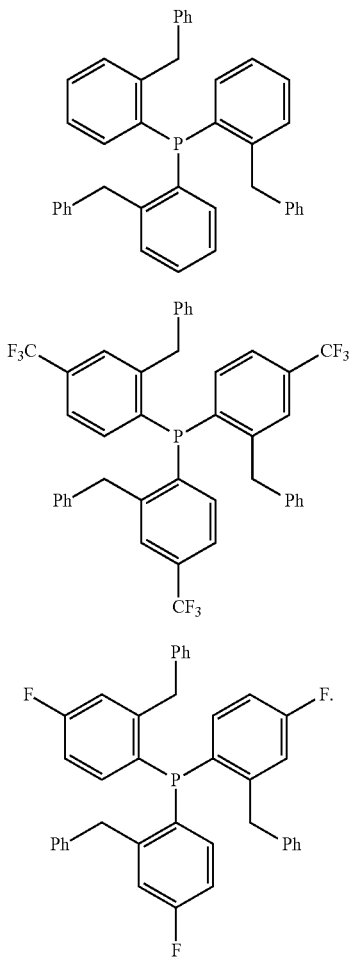

This disclosure also provides various embodiments of a composition comprising a phosphine compound described herein and a palladium catalyst.

In additional embodiments, the disclosed composition comprises an oxidative addition adduct of a cross-coupling substrate inserted into the palladium catalyst to form the oxidative addition adduct, wherein the composition catalyzes the formation of a stereoretentive cross-coupling product with greater than about 90% enantiospecificity when in contact with a secondary $Csp^3$ boronic acid.

This disclosure provides various embodiments of a method to form a stereoretentive carbon-carbon bond comprising:
 a) combining a cross-coupling substrate, a secondary $Csp^3$ boronic acid, a palladium catalyst, and a phosphine compound disclosed above to form a reaction mixture; and
 b) heating the reaction mixture;
 thereby forming a cross-coupling product of the cross-coupling substrate and the boronic acid, wherein a stereoretentive carbon-carbon bond is formed in the cross-coupling product.

In various embodiments, the phosphine compound is used in about 1 mole % to about 25 mole % with respect to the moles of the cross-coupling substrate. In various embodiments, an oxidative addition adduct of the cross-coupling substrate, the palladium catalyst and the phosphine compound forms a square planar palladium (II) stereoretentive transmetalation species with the boronic acid, wherein $R^1$ moieties of the phosphine compound inhibit stereoinvertive transmetalation, thereby forming the stereoretentive carbon-carbon bond from the stereoretentive transmetalation species.

In various embodiments, the stereoretentive carbon-carbon bond is formed with greater than about 90% enantiospecificity. In additional embodiments, the enantiospecificity increases when $R^2$ of the phosphine compound is an electron withdrawing group. In some embodiments, the cross-coupling substrate comprises a vinyl halide or an aryl halide. In certain embodiments, the reaction mixture comprises a silver additive. The silver additive can be, for example, a salt or an oxide of silver.

In yet other embodiments, the phosphine compound is IIIA, IIIB, or IIIC:

In some additional embodiments, a branched product is formed in favor of a linear product in a ratio of greater than about 20:1. In other embodiments the B:L ratio (branched to linear ratio) is about 20:1 to about 1000:1. In yet other embodiments, the B:L ratio is greater than about 50:1, 75:1, 100:1, 150:1, 200:1, 250:1, 300:1, 400:1, 500:1, 600:1, 700:1, 800:1, 900:1, or 1000:1. In various additional embodiments, the secondary $Csp^3$ boronic acid is enantiomerically enriched. In some other embodiments, tri(2-benzyl-phenyl)phosphine (and other disclosed phosphine ligands disclosed herein) promotes highly stereoretentive cross-couplings of unactivated secondary Csp3 boronic acids or boronates.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Development of Novel Phosphine Ligands for Catalysts

Metal mediated cross-couplings that proceed via stereospecific transmetalation pathways have the theoretical potential to perfectly translate the stereochemical information pre-installed in chiral building blocks into chiral products. Given all the practical benefits of organoboronates, Crudden's 2009 report (*J. Amer. Chem. Soc.* 2010, 132 (48), 17108) of stereospecific cross-couplings of secondary pinacol boronic esters was a key advance. Many advances in stereospecific cross-couplings with different types of stereochemically defined $Csp^3$ organoboronates have since been reported. An important challenge has generally emerged in these types of couplings, however. Albeit stereospecific, these reactions often proceed with suboptimal levels of stereocontrol, which can also vary considerably and even reverse depending on the reaction conditions. These observations are attributable to energetically similar stereodivergent stereospecific pathways for transmetalation of $Csp^3$-B bonds to Pd(II) (FIG. 1b). The enantiospecificity (% es) of a coupling reaction, defined as $$\% \, es = \frac{ee_{product}}{ee_{reactant}},$$

should serve as a readout of the relative rates of the stereoretentive and stereoinvertive transmetalation pathways.

Recent evidence supports that stereoretentive transmetalation proceeds via initial formation of a Pd—O—B bound pre-transmetalation complex followed by inner sphere transfer of carbon from boron to palladium within the Pd(II) square plane. Alternatively, consistent with canonical associative ligand substitution on 16 electron d8 square planar complexes, invertive transmetalation likely involves initial outer sphere associative addition of the organoboronate above or below the square plane of the Pd(II) oxidative addition adduct. The differences in spatial orientation for these two types of transmetalations suggested an opportunity for rationally discriminating between these stereodivergent stereospecific pathways.

Figure 7:
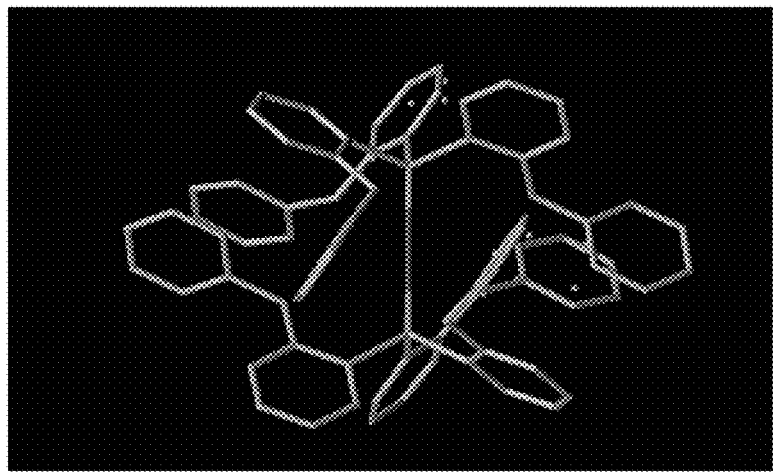
FIG. 7. Structure of $Pd[P(o\text{-}Bn\text{-}Ph)_3]_2$ showing pathways for stereoretentive and stereoinvertive transmetalation.
Figure 7:
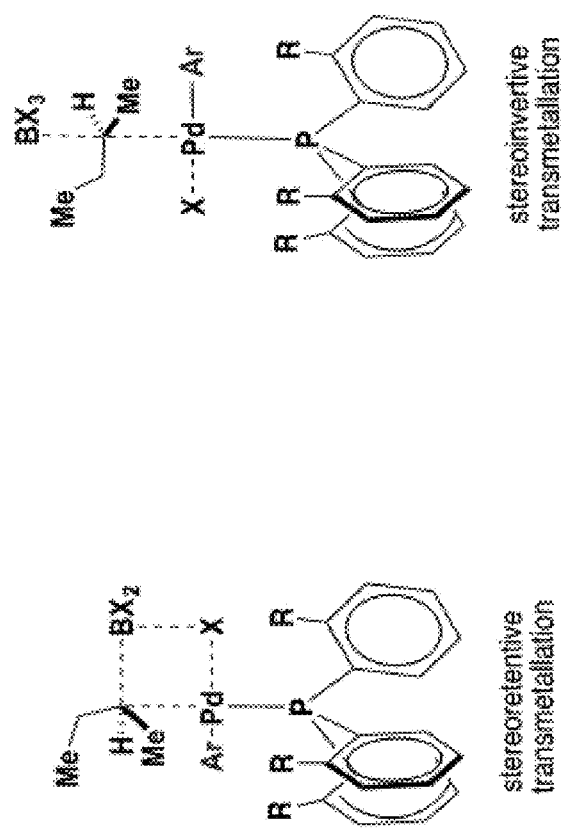

We specifically hypothesized that a ligand which selectively projects steric bulk above and below the Pd(II) square plane should block the stereoinvertive transmetalation mechanism while still allowing stereoretentive transmetalation to occur (FIG. 1c and FIG. 7). Encouraging precedent for this concept can be found in Brookhart's (*J. Amer. Chem. Soc.* 1995, 117, 6414) sterically bulky diimine ligands that promote high molecular weight polymerization of ethylene by minimizing associative displacement of the growing polymer chain. To our knowledge, such an approach has not previously been found to differentiate stereodivergent modes of transmetalation.

With this concept in mind, we were intrigued by a crystal structure of the oxidative addition adduct $\{[(o-MeC_6H_4)_3P]Pd(4-nBu-Ph)(Br)\}_2$. This phosphine ligand, tri(ortho-tolyl)phosphine, has previously been shown to disfavor β-hydride elimination. We noted that in this Pd(II) complex one ortho-methyl group projects above and the other projects below the Pd(II) square plane. The resulting zig-zag-like orientation is represented schematically in FIG. 1d. This analysis suggests that increasing steric bulk at the ortho-positions of triphenylphosphine would increasingly block the stereoinvertive associative addition pathway and thus maximize stereoretentive $Csp^3$ cross-coupling.

Results

We first tested how different ortho-substituted triarylphosphine ligands would affect the enantiospecificity of a prototypical $Csp^3$ coupling reaction. When unactivated chiral nonracemic 2-butylboronic acid was cross-coupled to para-bromo-biphenyl using $Pd_2dba_3$, triphenylphosphine, and silver oxide (FIG. 2a, entry 1), only 21% enantiospecificity was observed. Replacing triphenylphosphine with tri(ortho-tolyl)phosphine (entry 2) caused the enantiospecificity to increase to 86%. Further increasing the size of the ortho substituent to an ethyl group increased the enantiospecificity to 91% (entry 3), and near perfect enantiospecificity (98%) was achieved with the novel ligand, tri(2-benzyl-phenyl)phosphine, $[(2-Bn-Ph)_3]P$ (entry 4). Notably, across the same series of ligands, the yield and branched:linear ratios progressively increased as well, such that $[(2-Bn-Ph)_3]P$ provided an excellent yield of 72% and a near perfect B:L ratio (>250:1).

To gain further insight into how $[(2-Bn-Ph)_3]P$ promotes such high levels of stereoretention, we obtained a crystal structure of the dimeric Pd(II) oxidative addition adduct $[(2-Bn-Ph)_3PPd(p-OMePh)Br]_2$. Similar to the structure of the corresponding tri(ortho-tolyl)phosphinepalladium complex (cutaway shown in FIG. 1c), one of the benzyl groups is rotated to project away from Pd center, and the remaining two sterically bulky benzyl substituents are projected above and below the square plane of the Pd(II) complex. These observations are consistent with our hypothesis in which sterically blocking the sites above and below the Pd(II) square plane should selectively inhibit stereoinvertive transmetalation while permitting stereoretentive transmetalation to occur (FIG. 1d).

We recognized a complementary opportunity to probe this mechanistic model via electronic tuning of the phosphine ligands. In the proposed transition state for stereoretentive transmetalation, there is a trans relationship between the phosphine ligand and the nascent Pd-$Csp^3$ bond (FIG. 1b). Electron tuning of the phosphine ligand should thus strongly influence the rate of stereoretentive transmetalation, with electron poor ligands leading to faster transfer. In contrast, in the proposed transition state for stereoinvertive transmetalation, there is a cis relationship between the ligand and incoming carbon nucleophile, and thus ligand electronics should have relatively minor effect. Collectively, this analysis leads to the interesting prediction of a linear free-energy relationship and positive rho value for enantiospecificity as a function of electronically tuned tri-ortho-alkylphenylphosphine ligands.

Figure 6:
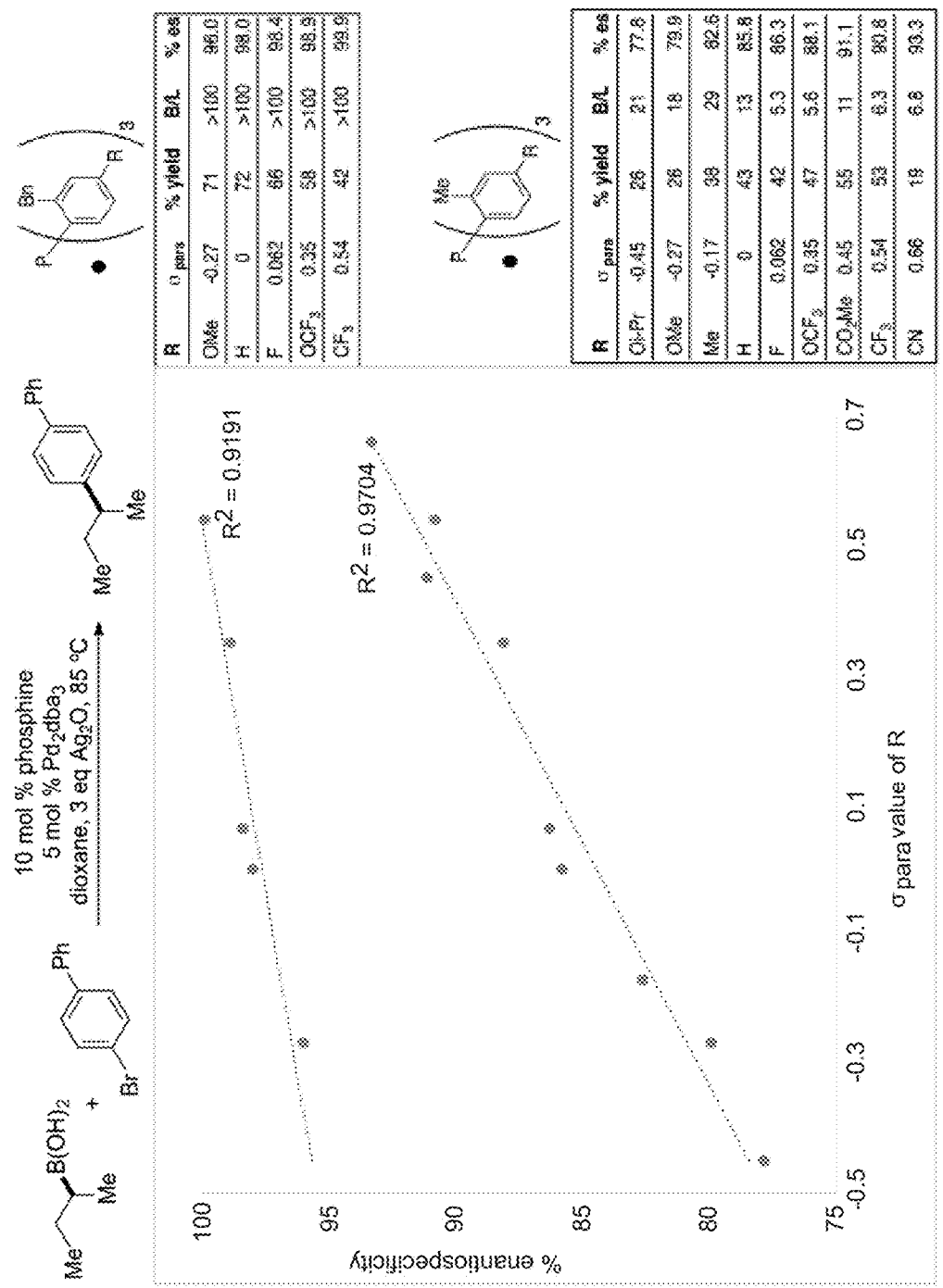
FIG. 6. Graph showing an increase in stereoretention through phosphine electronic tuning.

We thus synthesized series of $P(2-Me-Ph)_3$ and $P(2-Bn-Ph)_3$ derivatives with a range of electron-rich and poor substituents at the para positions of the corresponding aryl groups and employed them to promote the same $Csp^3$ cross-coupling (FIG. 2a and FIG. 6). Consistent with differentiation of the stereodiverent stereospecific transition states (FIG. 1b), we observed strong correlations ($R^2$=0.96 and 0.93) for enantiospecificity as a function of the sigma value of the para-substituents on both $P(2-Me-Ph)_3$ and $P(2-Bn-Ph)_3$. The most electron-deficient derivative of the P(2-Bn-Ph)$_3$ ligand, (4-CF$_3$-2-Bn-Ph)$_3$P, achieved perfect stereoretention (100%), albeit with somewhat reduced yield.

To further probe this mechanistic model, we performed similar cross-couplings using recently reported (*J. Amer. Chem. Soc.* 2014, 136 (40), 14027) aqueous basic conditions that have been shown to favor stereoinversion. Such conditions likely increase concentrations of the trihydroxyborate complex relative to the free boronic acid and thereby promote stereoinvertive transmetalation. Consistent with this hypothesis, when such couplings are performed with tri-tert-butyl phosphine as ligand and aqueous K$_2$CO$_3$ as base, we observed primarily stereoinvertive products (FIG. 2*e*). Simply replacing tri-tert-butyl phosphine with tri-ortho-tolyl-phosphine under otherwise identical conditions caused a turnover in stereochemical outcome, with stereoretention now being favored. Testing the same series of electronically tuned tri-ortho-tolylphonsphine derivatives again revealed a strong correlation between enantiospecificity and ligand electron-deficiency, with a much larger dynamic range in this case (9-73% es).

Collectively, these results provide strong support for the mechanistic model in which stereodivergent stereospecific pathways for transmetalation are differentiated by tri-ortho-alkylarylphosphines with selectively block associative addition of the organoboronate above and below the Pd(II) square plane.

Figure 3:
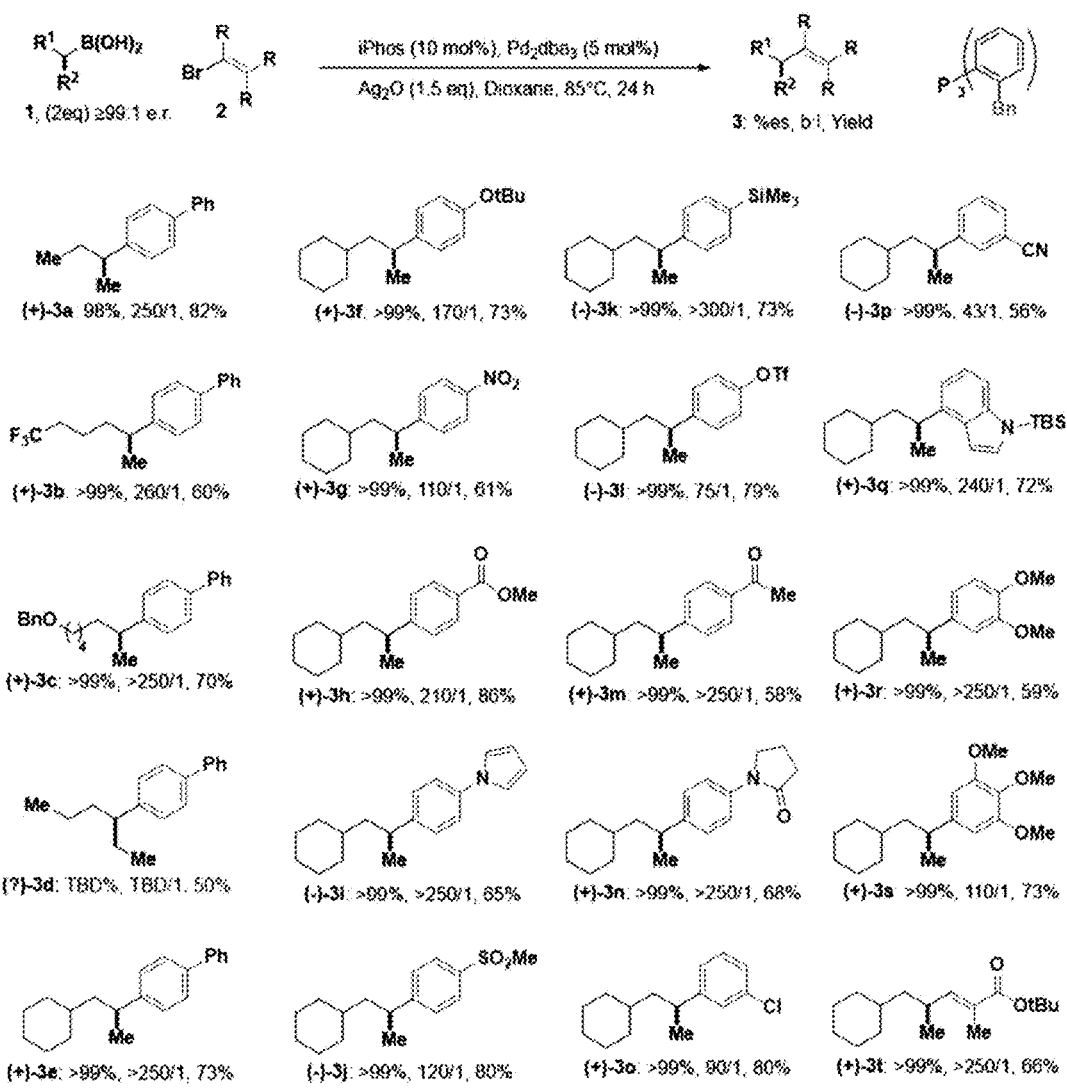
FIG. 3. Substrate scope of cross-coupling reaction. Branched/linear ratios were determined by HPLC analysis of the crude reaction using an authentic linear product standard. Yields were determined by isolation, and enantiospecificities were determined by chiral HPLC of the purified product.

Given the high enantiospecificity, yield, and B/L ratios observed for [(2-Bn-Ph)$_3$]P, we preliminarily examined the substrate scope for this highly stereoretentive cross-coupling reaction (FIG. 3). This first required a general method for practically accessing unactivated chiral nonracemic boronic acids in highly enantiomerically enriched form. Homochiral derivatives of N-methyliminodiacetic acid (MIDA) have previously been used for promoting diastereoselective epoxidations and resolution of atropdiastereomeric biaryl boronic acid adducts. We found that upon complexing a range of racemic secondary alkylboronic acids with a chiral MIDA variant, N-2-benzyloxycyclopentyl-iminodiacetic acid (BIDA; see US 2016/0280721, incorporated herein by reference), the corresponding diastereomeric BIDA boronates could be readily separated by chromatography and/or recrystallization to provide the corresponding highly enantioenriched boronic acids (≥99:1 e.r.) masked as air-stable building blocks.

Figure 8:
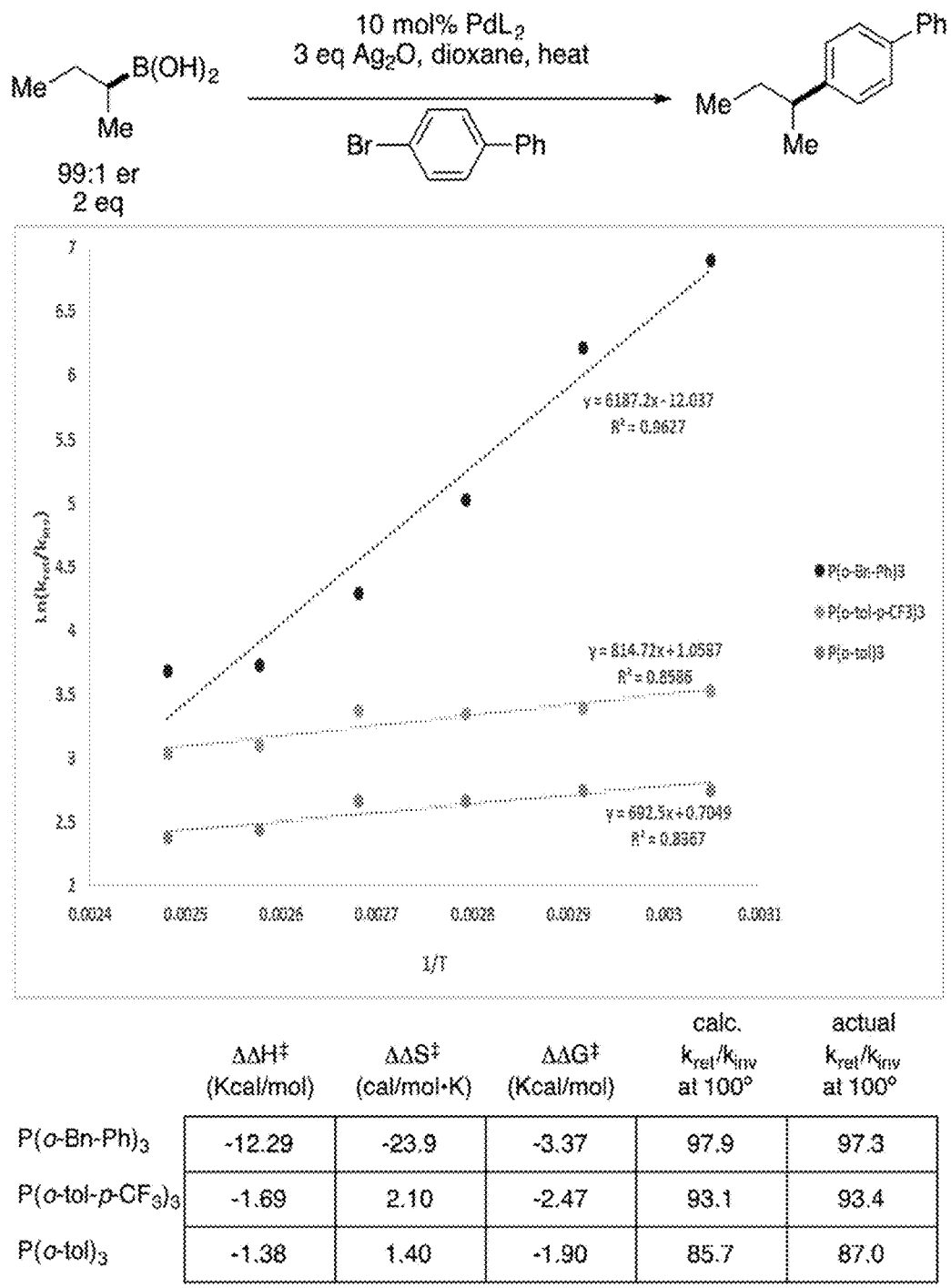
FIG. 8. Graph of $Ln(k_{ret}/k_{inv})$ versus $1/T$.

Using this methodology, a range of different unactivated secondary Csp$^3$ boronic acids were prepared in ≥99:1 e.r. and tested in the cross-coupling reaction under optimized conditions (FIG. 3 and FIG. 8). Various types of branching on the boronic acid were compatible, as were functional groups such as benzyl ethers and trifluoromethyl groups. Encouragingly, all of these coupling partners gave enantiospecificities ranging from 98→99%, branched/linear product ratios greater than 100:1, and good to excellent isolated yields of the targeted products.

The functional group tolerance of the reaction was further explored on the organohalide and found to include esters, ketones, ethers, nitro groups, nitriles, silanes, and sulfones. Moreover, perfect stereoretention was observed for cross-couplings with all the corresponding electron-rich and electron-poor aryl halides. Although aryl chlorides and aryl triflates were poor coupling partners, their lack of reactivity presented opportunities for orthogonal, halide-selective couplings. Some heterocycles, including pyrroles and indoles, were also well-tolerated. Finally, we observed a unique example of double stereoretentive Csp$^3$-Csp$^2$ cross-coupling between an unactivated secondary boronic acid and an activated vinyl halide. Unactivated vinyl halides provided little or no reactivity under these conditions.

We finally tested the capacity of this method to enable simple assembly of Csp$^3$-rich natural products and their stereoisomers. One of the key strengths of this approach is the potential to also readily access all possible Csp3 stereoisomers with the same outstanding level of stereocontrol by taking advantage of the stereospecific nature of the cross-coupling process. The recently discovered antifungal natural product xylarinic acid B served as an excellent case study.

Leveraging the simple BIDA boronate resolution method, all the required secondary Csp$^3$ boronate building blocks were readily accessed in ≥99:1 d.r. All four of these building blocks proved to be air- and chromatographically stable crystalline solids.

Figure 4:
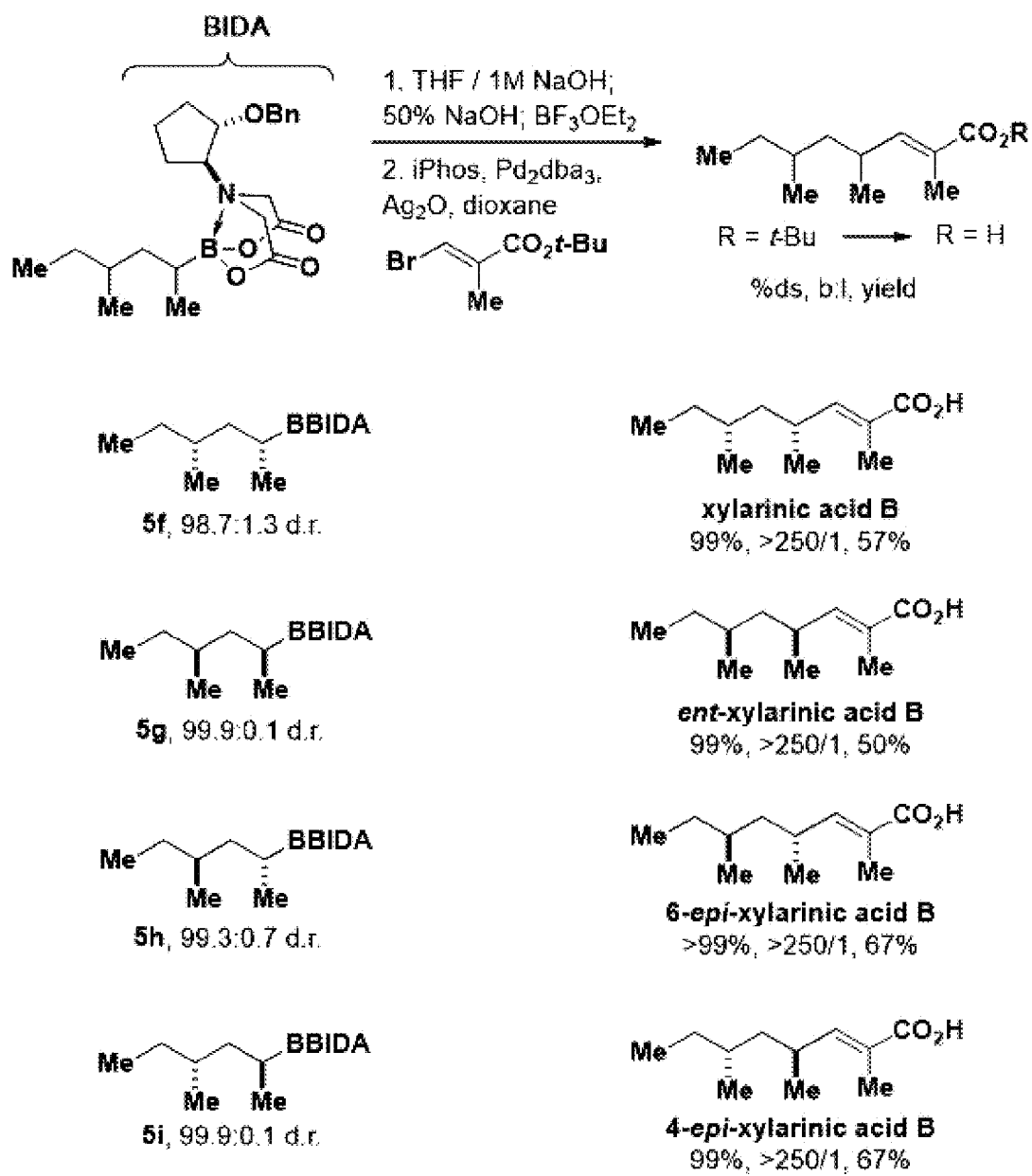
FIG. 4. Building block-based synthesis of all possible stereoisomers of the natural products xylarinic acid B.

This set the stage for the simple Lego-like assembly of xylarinic acid B, and all of its Csp$^3$ stereoisomers, via simple utilization of these four stereodefined building blocks. Specifically, each building block was deprotected to the corresponding boronic acid, and then stereospecifically cross-coupled to the relevant vinyl bromide using iPhos, and then deprotected under standard conditions. Through this simple approach, xylarinic acid B and all three of its Csp$^3$ stereoisomers of were readily accessed in ≥99% ds and >250/1 b:l ratios (FIG. 4).

Discussion

To simplify and generalize synthesis with off-the-shelf Csp$^3$ boronic acid building blocks, Csp$^3$ coupling methods require very high stereochemical control. Theoretically, this could be accomplished either with stereoselective or stereospecific Csp$^3$ couplings. Stereoselective couplings that proceed through single electron transmetalation mechanisms have the advantages of mild reaction conditions and high functional group tolerance. However, because the origin of stereochemical control in these systems is derived from subtle interactions between a prochiral substrate and a complementary chiral catalyst, even minor differences in substrate structure can cause large perturbations. As a result, the degree of stereochemical control can vary widely depending on the substrate, often requiring reoptimization for each new structural class of coupling partner.

In contrast, stereospecific couplings employ chiral non-racemic reactants that go through transition states that dictate only one stereochemical outcome. In these kinds of couplings, loss of stereochemical fidelity comes from a different cause, competing stereodivergent stereospecific transition states (FIG. 1*b*). In theory, strategies that allow for differentiating between these dissimilar transition states should be more independent of differences in substrate structure. Previously, competing stereodivergent stereospecific transmetalation mechanisms have been observed in the couplings of other configurationally stable organometallics, including chiral benzylic silanes and alkylstannanes. Activated organoboronate substrates have been reported to couple with primarily stereoinvertive or stereoretentive outcomes, depending on the activating group employed. Suginome has also shown that the choice of additive (PhOH or Zr(Oi-Pr)$_4$) can change the stereochemical course from invertive to retentive in couplings of α-(acetylamino)ben-zylboronic esters.

With the goal of developing a more general Csp$^3$ cross-coupling platform, methods are needed for highly stereocontrolled couplings of unactivated alkylboronic acids. To date, one example of the stereospecific coupling of unactivated alkylboronates has been reported, an invertive coupling between alkyltrifluoroborates and aryl halides, but the stereochemical control is variable. Guided by the working hypothesis that stereoinvertive transmetalation requires the approach of the trihydroxyborate to an axial coordination site on palladium, we sought strategies for mitigating reactivity at these sites. We specifically hypothesized that phosphine ligands with steric bulk projected above and below the palladium coordination sphere should be able to selectively inhibit the stereoinvertive transmetalation mechanism.

Figure 5:
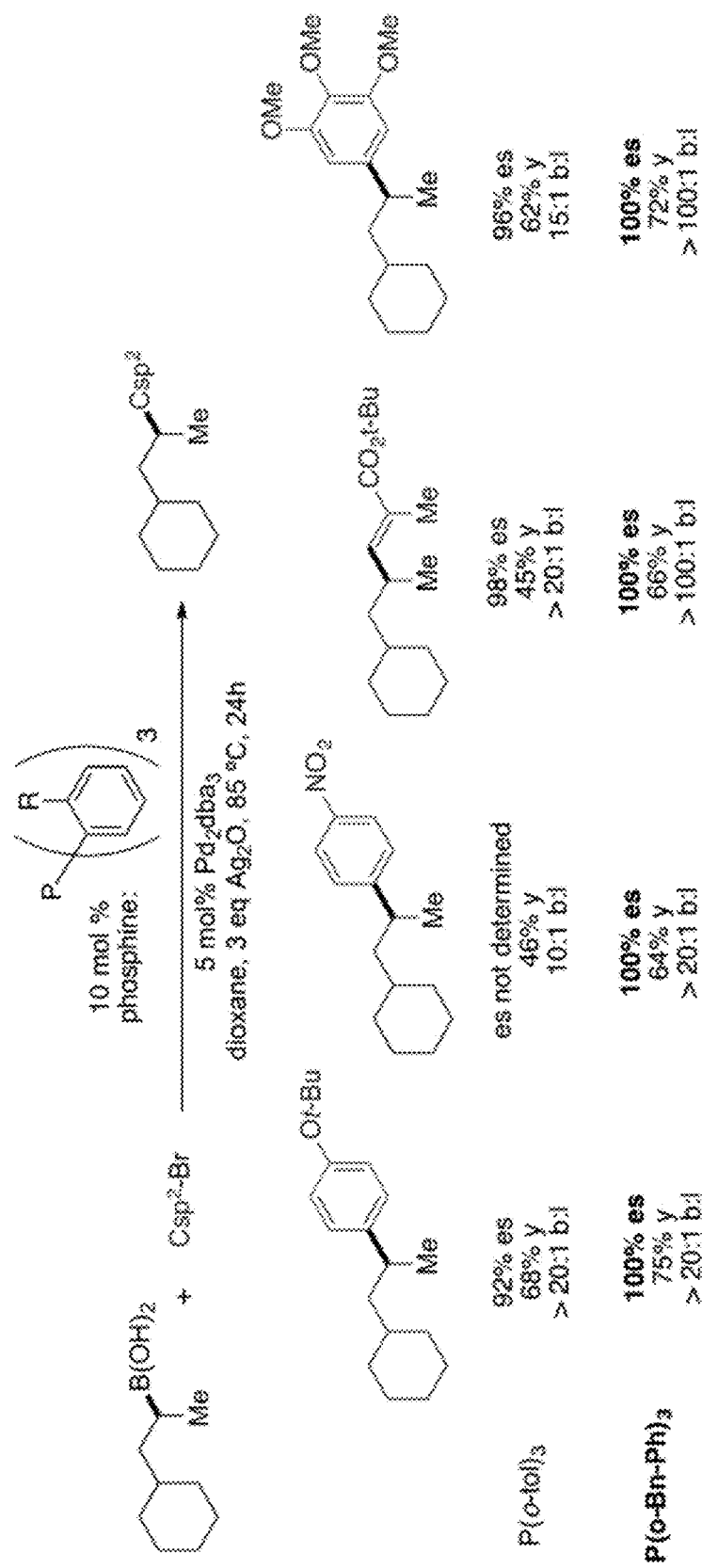
FIG. 5. Comparison of $P(o\text{-}tol)_3$ and $P(o\text{-}Bn\text{-}Ph)_3$.

When we tested this strategy on a triarylphosphine ligand scaffold, we observed a correlation between increasing steric bulk of the ortho-substituent (H, Me, Et, Bn) and the enantiospecificity of the stereoretentive coupling reaction. The optimized ligand P(2-Bn-Ph)$_3$ catalyzed the coupling with outstanding levels of stereocontrol over the entire substrate scope (FIG. 3 and FIG. 5), consistent with the idea that the inhibition of a competing stereospecific reaction mechanism should be relatively insensitive to substrate structure. It is also possible to bias this competition by accelerating the rate of the stereoretentive transmetalation pathway. Guided again by the model of competing stereodivergent stereospecific transition states (FIG. 1b), we predicted that electron-deficient phosphine ligands should accelerate the retentive mechanism (due to a trans effect) but have a minimal impact on the invertive mechanism.

Upon testing a range of electronically-tuned ligand derivatives, we found that there was a strong correlation between ligand electron-deficiency and stereoretention. The fact that this correlation was present on multiple ligand scaffolds (2-Me-Ph and 2-Bn-Ph phosphines) and multiple reaction conditions (anhydrous and aqueous biphasic) suggests that ligand electronics could serve as a design principle in other Csp$^3$ cross-coupling reactions. The electronically tuned ligand P(2-Bn-4-CF$_3$-Ph)$_3$, which gave the highest enantiospecificity in the model coupling reaction, also generated branched/linear ratios of >250/1. Although this hybrid ligand gave a somewhat lower yield (50%), tuning ligand electronics still be a promising avenue for further development.

We anticipate that the ligand design principles disclosed here may also be relevant to the development of new Csp$^3$ cross-coupling methodologies, accelerating the generalization of building block-based synthesis.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Preparation and Use of Novel Phosphine Ligands for Catalysis of Cross-Coupling Reactions The present disclosure provides novel phosphine ligands, such as, tri-orthoalkylphenyl phosphine ligands that, for the first time, enable stereospecific cross-couplings of unactivated secondary Csp$^3$ organoboronates with near-perfect levels of enantiospecificity and site-retention. This unprecedented high selectivity is general to wide range of reaction temperatures, halide substrates, and boronic acid substrates, thus enabling the building block-based syntheses of Csp$^3$- and stereocenter-rich targets. These new tri-orthoalkylphenyl phosphine catalysts, tuned electronically and sterically, enable, for the first time, cross-couplings of unactivated secondary boronic acids with near-perfect levels of site- and stereoretention.

The present disclosure describes the synthesis of these novel phosphine ligands, such as, tri-orthoalkylphenyl phosphines which provide higher yields and higher levels of stereospecificity and branched to linear product ratio than those obtained with the commercially available catalyst Pd[P(o-tol)$_3$]$_2$. The commercially available 2-bromobenzyl alcohol 1 or 2-bromo-5-trifluoromethyl-benzyl alcohol 2 is reacted with benzene and catalytic iron trichloride with heating to give the substituted diphenylmethane derivatives 3 and 4 (Scheme 1). After purification with silica gel and recrystallization, the phosphines 5 and 6 were obtained in pure form and were used in the cross-coupling reaction without further manipulation.

Scheme 1. A general procedure for the synthesis of phosphines and compounds 5 and 6.

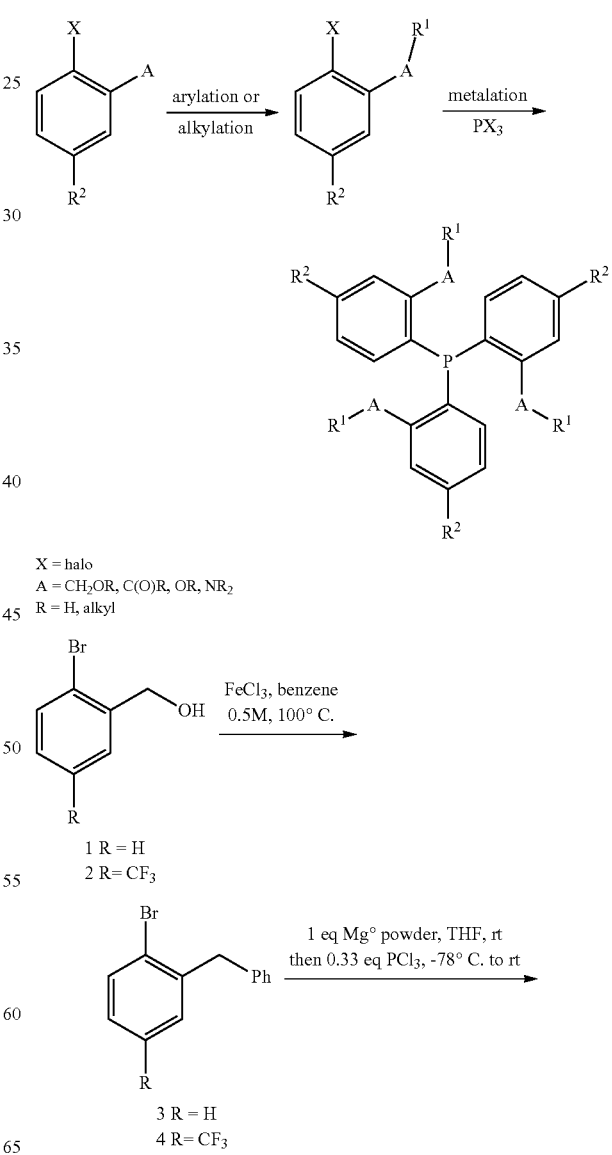

Preparation of Phosphine Ligands 5 and 6

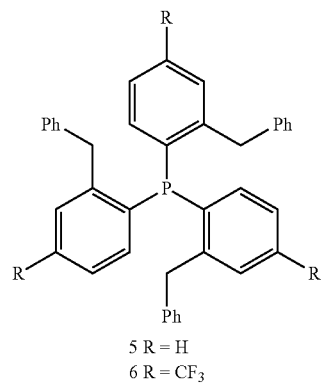

5 R = H
6 R = CF$_3$

Preparation of Intermediates 3 and 4.

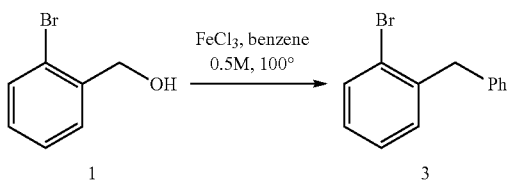 [SMILES: OCc1ccccc1Br ; Brc1ccccc1Cc1ccccc1]

Reagents:

Substrate 1: 4.68 g (25 mmol), anhydrous FeCl$_3$: 405 mg (2.5 mmol), anhydrous benzene: 50 mL.

To an oven-dried 200 mL high-pressure round-bottomed flask with screw-cap and stir bar was added 1 and FeCl$_3$ followed by benzene. The cap was tightly fitted and the flask was stirred in 100° oil bath for 12 hours. A TLC check in 100% hexanes under short wave UV indicated complete conversion of the starting alcohol. The reaction was filtered through a silica plug in a glass fritted funnel, washing through with 50 mL of Et$_2$O. The combined solution was concentrated under vacuum to a brown oil. This was purified by silica column chromatography, eluting with 100% hexanes. Concentration of the pure fractions under vacuum gave the known compound 3 as 4.02 g of colorless oil, 65%.

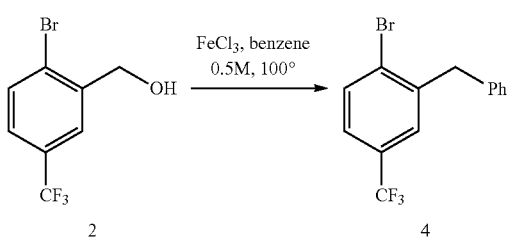 [SMILES: OCc1cc(C(F)(F)F)ccc1Br ; FC(F)(F)c1ccc(Br)c(Cc2ccccc2)c1]

Starting from 25.0 g (98.0 mmol) of alcohol 2, 4 was synthesized and isolated by an identical procedure as that described for the synthesis of 3. 4 was obtained as 24.3 g of a white crystalline solid. 77% yield.

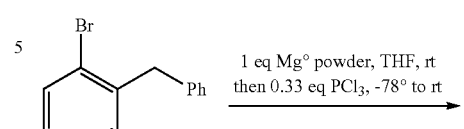

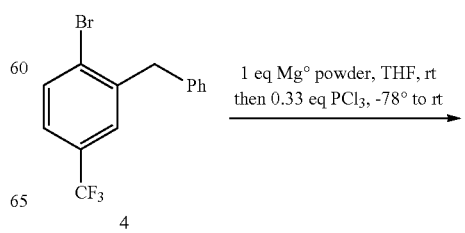

Substrate 3: 3.95 g (16 mmol), Mg powder: 389 mg (16 mmol) THF: 16 mL, PCl$_3$: 725 mg (5.33 mmol) 3 was added to a suspension of Mg powder in 16 mL THF (SDS) by syringe in a 40 mL vial under N$_2$ at rt. Catalytic I2 and brief heating was required to initiate the reaction as seen by a disappearance of the I2 color. This was stirred overnight at room temperature. TLC (100% hexanes) of a quenched aliquot showed complete consumption of 3. The solution was cooled to −78° in an acetone/dry ice bath and neat PCl$_3$ was added dropwise by syringe. The reaction was stirred 1 hour at −78°, then at room temperature overnight. Solids formed in the orange reaction. TLC (5% EtOAc/hexanes) showed nearly complete conversion of the intermediate dehalogenated compound. Saturated NH$_4$Cl was added, followed by H$_2$O. The aqueous phase was extracted twice with EtOAc. The combined organic phase was dried with Na$_2$SO$_4$ and concentrated to a red oil under vacuum. This was filtered through a silica plug with 5% EtOAc/hexanes in a glass frit to remove the red, baseline material and the flow-through was concentrated to an oil.

Figure 9:
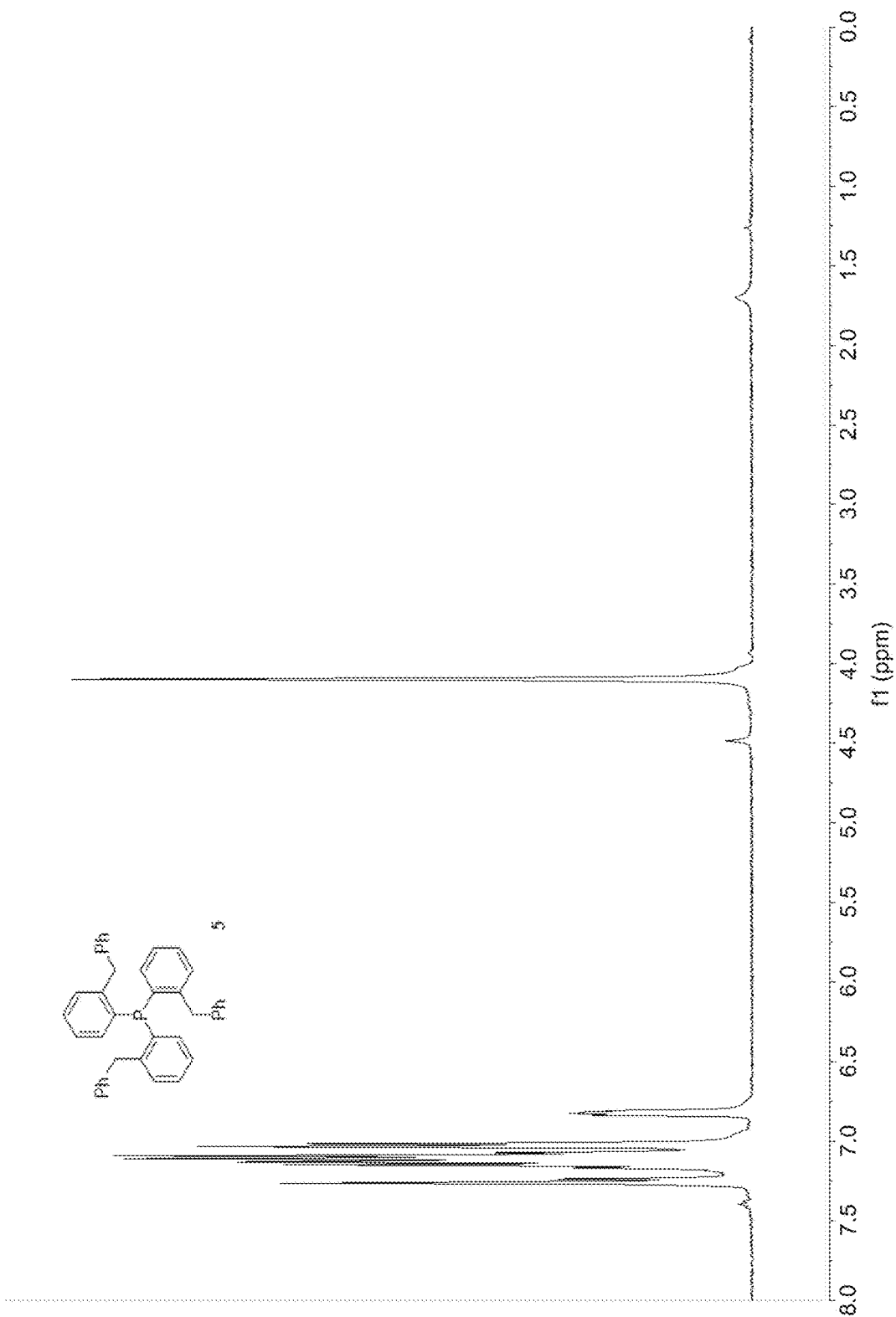
FIG. 9. $^1H$ NMR of $P(o\text{-}Bn\text{-}Ph)_3$.

This material was dissolved in a minimal amount of DCM with heating. Upon cooling to room temperature, 7 volumes of hexanes were added. This was stirred in an ice bath for ~30 minutes to induce crystallization of the product. This was done a second time on the collected solids. 1.88 g of 5 was obtained as white solid. 22% yield (FIG. 9).

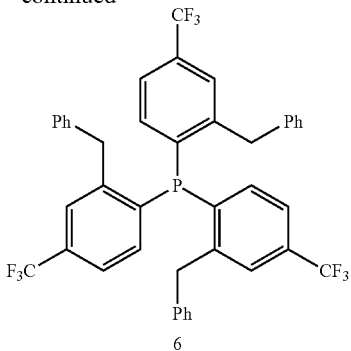

6

Starting from 2.16 g of 4, 6 was synthesized by an identical procedure as that described for the synthesis of 5. After filtration of the crude through a silica plug to remove baseline impurities as described above, the concentrated flow-through was recrystallized by dissolving in 7 mL of hot MeOH and was stirred 30 minutes in an ice bath. Collection of the solid by filtration gave 6 as 530 mg of a white crystalline solid. 31% yield.

Example 2. General Methods, Procedures, and Ligand Analysis

Materials.

Commercial reagents were purchased from Sigma-Aldrich, Fisher Scientific, Alfa Aesar, TCI America, or Frontier Scientific, and were used without further purification, with the following exception. All commercially available aryl halides were dissolved in DCM and passed through a silica plug to remove baseline impurities, followed by concentration under vacuum. Pd(P(o-tol)$_3$)$_2$, and Ag$_2$O were purchased from Sigma-Aldrich. A gift of Pd(P(o-tol)$_3$)$_2$ was donated by Johnson Matthey. Solvents were purified via passage through packed columns as described by Pangborn and coworkers (Pangborn et al., *Organometallics*, 1996, 15, 1518-1520) (THF, Et$_2$O, CH$_3$CN, CH$_2$Cl$_2$: dry neutral alumina; hexane, benzene, and toluene, dry neutral alumina and Q5 reactant; DMSO, DMF: activated molecular sieves). Acetone was dried by stirring 24 hours with boric anhydride followed by distillation. Anhydrous 1,4-dioxane was purchased from Sigma-Aldrich and used without further manipulation. All water was deionized prior to use.

General Experimental Procedures.

Unless noted, all reactions were performed in round bottom flasks fitted with rubber septa or Teflon-lined screw-cap vials (vials: VWR catalog number 66022-300; vial caps: VWR catalog number 16198-911) under argon or nitrogen. Organic solutions were concentrated via rotary evaporation under reduced pressure with a bath temperature of 30° C. unless otherwise noted. Reactions were monitored by analytical thin layer chromatography (TLC) performed using the indicated solvent on Merck silica gel 60 F254 plates (0.25 mm). Compounds were visualized by exposure to a UV lamp (λ=254 nm), and/or a solution of KMnO4 and/or a solution of cerium ammonium molybdate followed by brief heating using a Varitemp heat gun. Column chromatography was performed using Merck silica gel grade 9385 60 Å (230-400 mesh). Preparative HPLC was performed with a Waters SunFire™ Prep C18 OBD™ 5 µm 30 mm×150 mm column, Part No. 186002797. Chiral HPLC was performed with a Chiralcel® OD-H column, 4.6 mm×250 mm, 5 µm particle size, part No. 14325, and a Chiralcel® AD-H column, 4.6 mm×250 mm, 5 µm particle size, part No. 19325.

Structural Analysis.

$^1$H NMR and $^{13}$C NMR spectra were recorded on Varian Unity 500, Varian Unity Inova 500NB, Varian Unity 400 or Varian Unity 500 instruments. Chemical shifts (δ) are reported in parts per million (ppm) downfield from tetramethylsilane and referenced to residual protium in the NMR solvent (benzene, δ=7.16; CHCl$_3$, δ=7.26; acetone, δ=2.05, center line; DMSO δ=2.50, center line) or to added tetramethylsilane (δ=0.00). $^{13}$C NMR spectra in D$_2$O are referenced to added acetonitrile (δ=119.68, 1.47). For $^1$H spectra taken at 50° C., the HOD peak was set to 4.496 ppm (Gottlieb et al., *J. Org. Chem.* 1997, 62, 7512-7515). Data are reported as follows: chemical shift, multiplicity (s=singlet, d=doublet, t=triplet, q=quartet, quint=quintet, sept=septet, m=multiplet, b=broad, app=apparent), coupling constant (J) in Hertz (Hz), and integration. Chemical shifts (δ) for $^{13}$C NMR are reported in ppm downfield from tetramethylsilane and referenced to carbon resonances in the NMR solvent (benzene-d6, δ=128.06, center line; CDCl$_3$, δ=77.0, center line; acetone-d$_6$, δ=29.5, center line; DMSO-d$_6$ δ=39.52, center line). Carbons bearing boron substituents were not observed (quadrupolar relaxation). High resolution mass spectra (HRMS) were performed at the University of Illinois School of Chemical Sciences Mass Spectrometry Laboratory.

General Procedures

A. Synthesis of MIDA and BIDA Boronates

To a 250-mL round-bottom flask with a stir bar was added (±)-1a (1.02 g, 10 mmol, 1.0 eq, obtained from Frontier Scientific), N-methyliminodiacetic acid (MIDA) (1.77 g, 12 mmol, 1.2 eq), DMSO (10 mL, 1 Molar), and toluene (90 mL, 0.11 Molar). The mixture was fitted with a Dean Stark trap, on top of which was fitted a reflux condenser. The mixture was heated to reflux and water was collected in the trap for 2 hours, at which point complete conversion of the boronic acid was confirmed by TLC (100% EtOAc, KMnO$_4$). The toluene was then removed by rotary evaporation. 75 mL of H$_2$O was added, and the mixture was extracted with EtOAc (5×75 mL). The combined organic phase was washed with H$_2$O (75 mL×5). The organic phase was then dried over Na$_2$SO$_4$ and concentrated under vacuum to give (±)-6a as a white solid (1.49 g, 70%), which was used without purification. This material was stable in a capped vial under air on a bench top for at least 4 months (see below).

The synthesis of BIDA boronates was performed with this same procedure, using BIDA (0.83 eq) instead of MIDA. The resulting diastereomeric mixtures were resolved by recrystallization and/or column chromatography. Specifically, crude BIDA boronate (mixture of 5a and epi-5a, prepared from 41.2 mmol of boronic acid (±)-1a and 34.4 mmol BIDA) was filtered through a pad of silica gel, rinsing with acetone. After rotary evaporation, the crude product (12.03 g, 94% crude yield) was dissolved under nitrogen in anhydrous boiling acetone (35 mL). After cooling to room temperature, anhydrous Et$_2$O (70 mL) was added gradually. The mixture was cooled to 0° C. and filtered through a medium porosity glass frit, affording a partially resolved product (4.72 g, 12.7 mmol). This diastereomeric mixture was recrystallized in the same manner (24 mL acetone, 48 mL Et$_2$O, giving 9.37 mmol product, 98:2 d.r.). A third recrystallization (20 mL acetone, 40 mL Et$_2$O) gave the ≥99:1 d.r. BIDA boronate (2.836 g, 7.598 mmol, 22% yield).

$^1$H-NMR in CDCl$_3$ showed a diastereomeric ratio of ≥99:1 by integrating the methyl signals of 5a and epi-5a at 0.88 and 1.00 ppm, respectively.

5a, 99:1 d.r.: $^1$H NMR (500 MHz, CDCl$_3$) δ 7.46-7.37 (m, 2H), 7.35-7.26 (m, 3H), 4.67 (d, J=11.5 Hz, 1H), 4.40 (d, J=11.5 Hz, 1H), 4.03 (d, J=16.6 Hz, 1H), 3.93 (q, J=6.7 Hz, 1H), 3.69-3.59 (m, 2H), 3.46 (d, J=16.6 Hz, 1H), 3.35 (d, J=16.9 Hz, 1H), 2.31-2.19 (m, 1H), 2.15-2.03 (m, 1H), 1.93-1.62 (m, 4H), 1.56-1.46 (m, 1H), 1.35-1.23 (m, 1H), 0.95 (t, J=7.4 Hz, 3H), 0.90 (d, J=7.0 Hz, 3H), 0.82-0.72 (m, 1H). $^{13}$C NMR (126 MHz, CDCl$_3$) δ 168.91, 167.35, 136.41, 128.99, 128.76, 128.45, 79.16, 72.11, 72.09, 61.07, 56.13, 29.62, 26.60, 25.25, 21.42, 14.30, 12.79. $^{11}$B NMR (128 MHz, CDCl$_3$) δ 14.03. HRMS (ES$^+$) Calculated for C$_{20}$H$_{29}$BNO$_5$: 374.2139; Found: 374.2140.

B. Synthesis of Sodium Alkyltrihydroxyborate Salts

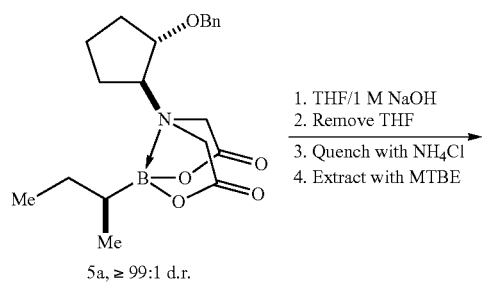

5a, ≥ 99:1 d.r.

1. THF/1 M NaOH
2. Remove THF
3. Quench with NH$_4$Cl
4. Extract with MTBE

To a stir bar-equipped 250-mL round-bottom flask under air was added BIDA boronate 5a (2.426 g, 6.499 mmol, 1.00 eq), THF (33 mL, 0.20 Molar) and freshly prepared 1 Molar NaOH (33 mL, 5.0 eq). The mixture was stirred at 23° C. until complete conversion was confirmed by TLC (1:1 Hex/EtOAc, KMnO$_4$). THF was removed under rotary evaporation (bath temperature 40° C.). When most of the THF was removed, the receiving flask was emptied and dried and rotary evaporation was then continued until water condensation began to collect in the receiving flask. Saturated NH$_4$Cl (33 mL) was added to the resulting aqueous solution and this was extracted with MTBE (4×33 mL) in a separatory funnel. The combined MTBE phase was dried over Na$_2$SO$_4$ and partially concentrated (volume=33 mL, 0.20 Molar) by rotary evaporation. To this solution was added aqueous 50% NaOH (0.343 mL, 0.520 g solution, 0.260 g NaOH, 6.50 mmol) over one minute with rapid stirring. The suspension was stirred for 20 minutes at 23° C., causing a white precipitate to form. The flask was then sonicated for 5 minutes. The white precipitate was collected by concentration in vacuo or by filtration through a medium porosity glass frit, rinsing with MTBE. The product was dried under vacuum at <1 mbar at 23° C. for 10 hours to give (S)-7a (0.8982 g, 6.328 mmol, 97% yield)), as a colorless, free-flowing powder. This product was generally stored at 23° C. under nitrogen. In a stability test, this material was stable on the benchtop under air for at least 4 months (see below).

$^1$H NMR (500 MHz, D$_2$O, 50° C.) δ 1.48-1.36 (m, 1H), 1.00-0.89 (m, 1H), 0.85 (t, J=7.2 Hz, 3H), 0.75 (d, J=7.5 Hz, 3H), 0.20 (m, 1H). $^{13}$C NMR (126 MHz, D$_2$O, 50° C.) δ 26.56, 15.52, 14.14. $^{11}$B NMR (128 MHz, D$_2$O, 50° C.) δ 8.29.

C. Synthesis of Boronic Acids as Dioxane Solutions

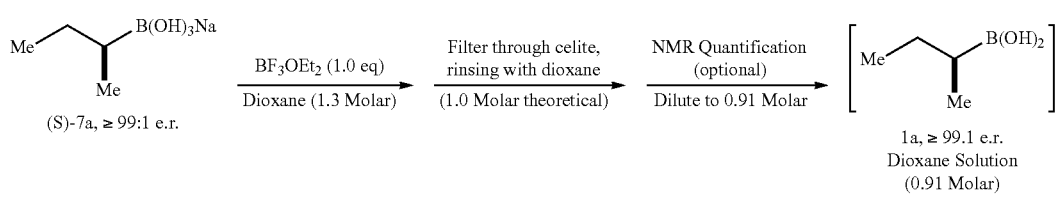

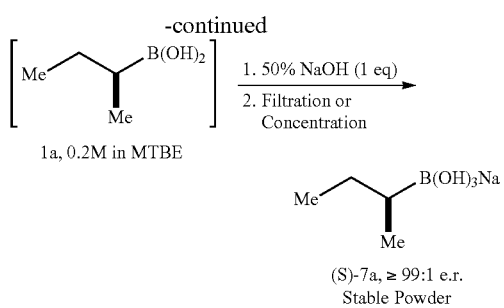

Sodium alkyltrihydroxyborate (S)-7a (0.213 g, 1.50 mmol, 1.00 eq) was added to a 2 mL screw-cap vial with a stir bar. Anhydrous dioxane (1.15 mL, 1.3 Molar) was added and the slurry was vigorously stirred. BF$_3$.OEt$_2$ (0.185 mL, 0.213 g, 1.50 mmol, 1.00 eq) was added dropwise over 15 minutes. If the mixture became unstirrable, it was periodically capped and shaken by hand. After completion of the addition, the vial was capped and stirred for 20 minutes. The resulting thin suspension was filtered by passing through a Pasteur pipette containing 40 mg of Celite over a small cotton plug, using pressure from an applied air hose. The residue from the vial was washed through with additional dioxane (0.35 mL, 1.0 Molar theoretical concentration). The resulting homogeneous solution amounted to 1.15 mL. An aliquot of this solution (30 µl, 30 µmol theoretical) was combined with a standard solution DMSO-d$_6$ and 1,4-dimethoxybenzene (0.050 Molar, 0.60 mL, 30 µmol 1,4-dimethoxybenzene) in an NMR tube. The boronic acid was analyzed by $^1$H-NMR with the relaxation delay (d1) set to 10 seconds. The concentration of boronic acid 1a was determined to be 1.07M, giving a yield of 82%. The only visible impurity was diethyl ether (see spectrum of 1a and standard). This solution was diluted to 0.91 Molar by adding dioxane (0.20 mL) and was then transferred in a capped vial into a glovebox and used in the cross coupling step. In a stability test, this boronic acid solution was stored on the benchtop under air for 4 months and showed less than 10% decomposition.

This procedure proved to be scalable and could also be carried out in 7 mL vials using 3-4 mmol of the sodium alkyltrihydroxyborate.

1a: $^1$H NMR (400 MHz, DMSO-$d_6$) δ 7.25 (s, 2H), 1.33 (dq, J=15.2, 7.8 Hz, 1H), 1.17 (dq, J=13.5, 6.7 Hz, 1H), 0.88-0.74 (m, 6H), 0.69 (p, J=7.2 Hz, 1H).

D. Set-Up of the Cross-Coupling Reaction

Ligand Testing.

To a stir bar-equipped 7 mL vial were added a phosphine ligand (0.010 mmol, 10 mol %), Pd$_2$dba$_3$ (4.6 mg, 0.0050 mmol, 5 mol %), 4-bromobiphenyl 2a (23.3 mg, 0.100 mmol, 1.00 eq), and Ag$_2$O (69.5 mg, 0.3 mmol, 3 eq). A dioxane solution of boronic acid 1a (0.91 Molar, 0.220 mL, 0.200 mmol, 2.00 eq) was added by pipette. The vial was tightly sealed with a teflon-lined screw cap and stirred at 200 rpm at 85° C. for 24 hours. Upon completion, the reaction mixture was filtered through a silica gel plug in a Pasteur pipette, rinsing with HPLC grade hexanes. The filtrate was collected in a 25 mL volumetric flask and diluted up to the mark. After thorough mixing, an aliquot of this solution was transferred to an HPLC vial and immediately subjected to HPLC analysis (OD-H chiral column, 2.0 mL/min, isocratic 100% hexanes, 214.4 nm absorbance). On each new day of HPLC analysis, a standard solution of the branched product standard was analyzed in duplicate to confirm the bulb brightness and to adjust response factors if necessary. If peak retention times drifted, standards were repeated as necessary to confirm the identity of the peaks.

Substrate Table.

The reaction was assembled as described above, except using 1.5 equivalents of Ag$_2$O (34.8 mg, 0.15 mmol). After 24 hours, the reactions were cooled and filtered through silica gel in a glass pipet, rinsing Et$_2$O or EtOAc. An aliquot of the crude reaction mixture was first subjected to HPLC analysis to determine the branched/linear product ratio, comparing with an authentic sample of the linear product isomer. The crude reaction was then purified by column chromatography, and then the enantiospecificity was determined by chiral HPLC.

E. Improved Synthesis and Recovery of the BIDA Ligand 2,2'-(((1S,2S)-2-(benzyloxy)cyclopentyl)azanediyl) diacetic acid (BIDA)

A stir bar-equipped, 3-neck 5 liter round bottom flask was fitted with a reflux condenser and thermometer. Under air, this flask was charged with K$_2$CO$_3$ (213 g, 1.54 mol, 5.00 eq), MeCN (500 mL), and (1S,2S)-(+)-2-benzyloxycyclopentylamine (58.8 g, 308 mmol, 1.00 eq). This mixture was cooled to 0° C., and a solution of tert-butyl bromoacetate (109 mL, 144 g, 740 mmol, 2.40 eq) in MeCN (250 mL) was added, rinsing with MeCN (for a total volume of 935 mL MeCN, 0.33 Molar). The mixture was stirred at 70° C. for 24 hours.

The next day, the mixture was filtered through celite, rinsing with EtOAc. The filtrate was concentrated thoroughly in vacuo to afford a viscous oil. Using formic acid (310 mL, 378 g, 8.21 mol, 26.7 eq), the crude product was transferred to a stir bar equipped 3-neck 3 liter round bottom flask. The flask was equipped with a Vigreux condenser and heated at 85° C. for 2 hours. An aliquot of the reaction was examined by NMR, confirming that the deprotection was complete.

The reaction was thoroughly concentrated in vacuo to remove all formic acid. The resulting viscous red oil was dissolved in hot EtOH (1250 mL), creating a super saturated solution. Soon after, a white powder began to crash out. The mixture was cooled to 0° C. and filtered through a medium porosity glass frit, rinsing with additional cold EtOH. The product was dried in vacuo to afford an off-white powder (56.6 g, 184 mmol, 70% overall yield). Product characterization matched a previous report (Li, J.; Burke, M. D., *J. Amer. Chem. Soc.* 2011, 133 (35), 13774).

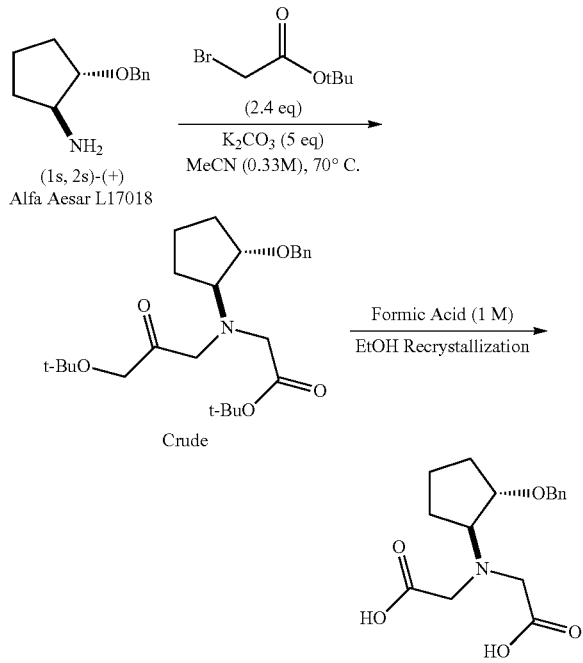

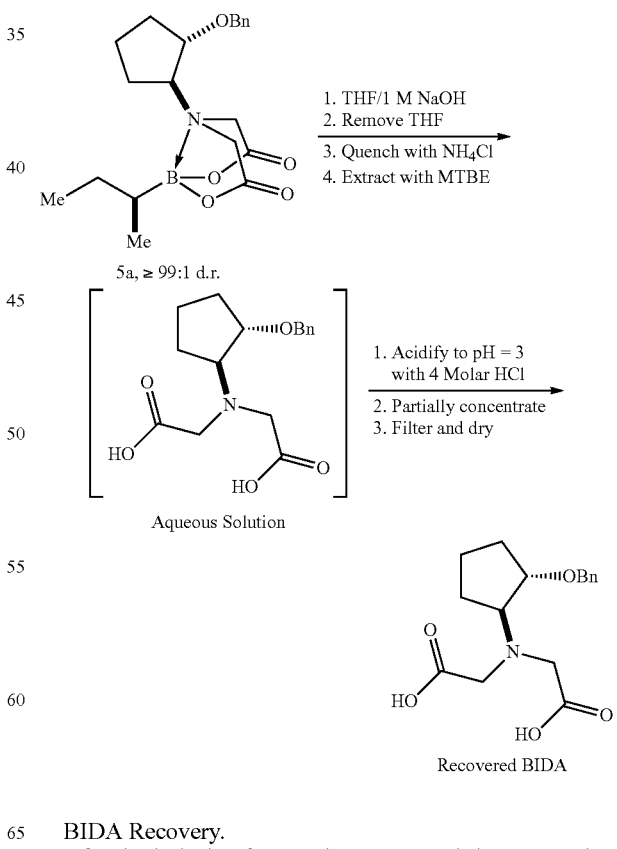

BIDA Recovery.

After hydrolysis of BIDA boronates and the preparation of sodium alkyltrihydroxyborate salts, the BIDA ligand could be recovered in 85% yield. Specifically, BIDA boronate 5a (≥99:1 d.r., 0.933 g, 2.50 mmol) was converted to sodium alkyltrihydroxyborate salt (S)-7a by General Procedure B. After addition of saturated aqueous NH$_4$Cl and MTBE extraction, the aqueous phase was acidified to pH 3 with 4 Molar HCl and then concentrated by rotary evaporation with a 40° C. bath until precipitation began. The solution was then stirred in an ice bath for one hour. Filtration through a medium porosity glass frit followed by drying on high vacuum afforded BIDA as a white solid (0.651 g, 2.12 mmol).

Figure 2:
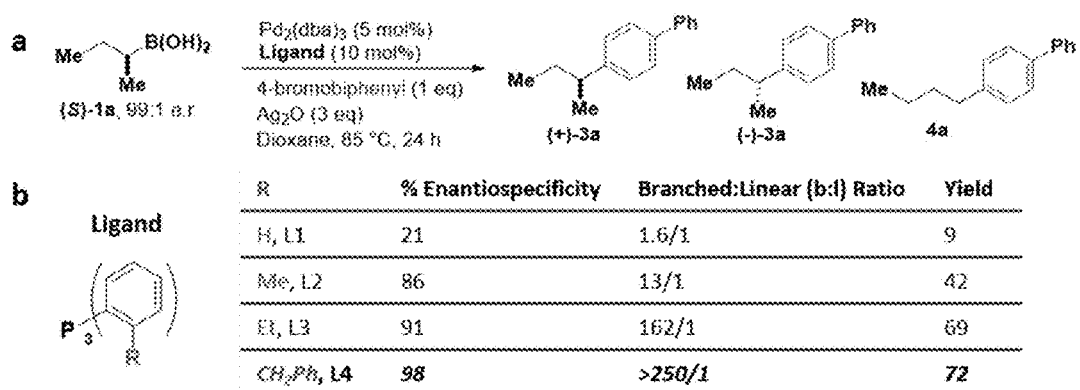
FIG. 2. Ligand optimization. (A) Test coupling reaction for optimizing ligands. (B) ortho-substituent optimization. (C) Oxidative addition adduct crystal structure showing that $P(2\text{-}Bn\text{-}Ph)_3$ is capable of blocking the axial sites on Pd. (D) Correlation between ligand electronics and enantiospecificity under anhydrous conditions from FIG. 2a. (E) Phosphine ligand as the determinant of the stereochemical outcome. (F) Correlation between ligand electronics and enantiospecificity under aqueous biphasic conditions from FIG. 2e.
Figure 2:
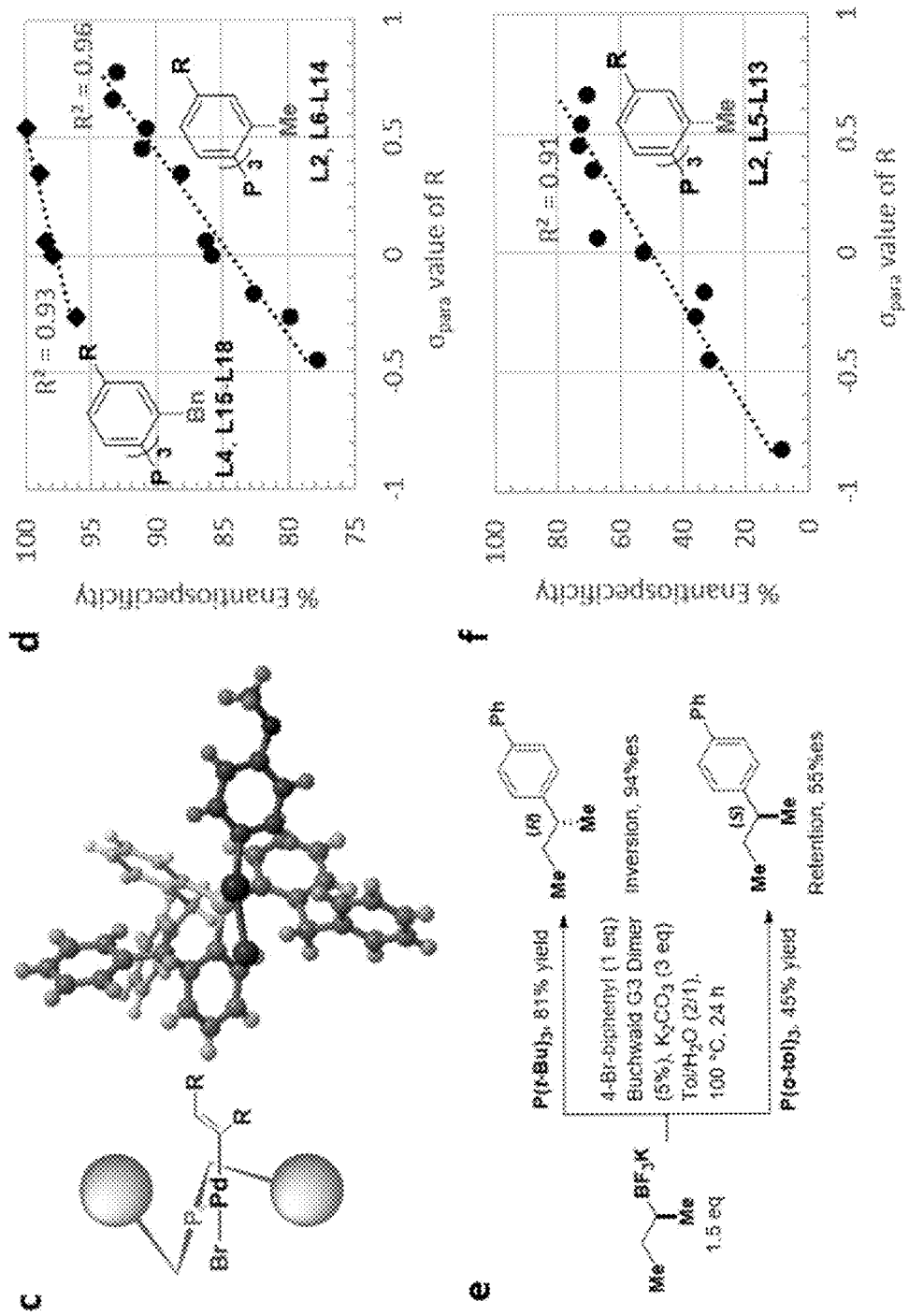

Synthesis and Characterization of Phosphine Ligands (FIGS. 2, 4, and 6)

Tris(2-methylphenyl)phosphine L2

This ligand was purchased from Sigma Aldrich (Product number 287822, Lot number MKBK8331V).

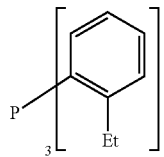

Tris(2-ethylphenyl)phosphine L3

An oven dried, 50 mL 3-neck round bottom flask equipped with a stir bar was fitted with a thermometer adapter, a nitrogen inlet, and a rubber septum. The apparatus was vac-filled three times with nitrogen and charged with 1-bromo-2-ethylbenzene (0.55 mL, 740 mg, 4.0 mmol, 1.0 equiv.) and THF (6.5 mL, 1.6 Molar). The RBF was lowered into a dry ice/acetone bath and allowed to equilibrate for over 20 minutes. nbutyllithium (1.6 Molar in hexanes, 2.4 mL, 3.8 mmol, 0.95 equiv.) was added dropwise over 10 minutes, keeping temperature below −60° C. The reaction appearance changed from colorless to green. Following the addition, the reaction mixture was allowed to stir for one hour and 50 minutes in the dry ice/acetone bath.

An oven dried 40 mL vial equipped with a stir bar was backfilled with nitrogen and charged with phosphorus trichloride (0.36 mL, 0.565 g, 4.12 mmol) and THF (8.0 mL; 0.515 Molar). 2.1 mL of the resulting PCl$_3$ solution (1.08 mmol, 0.27 eq) was transferred to the reaction mixture over 10 minutes (maintaining a temperature below −54° C.). Following the addition, the reaction mixture was allowed to stir and warm to room temp overnight. The reaction mixture was cooled to 0° C. in an ice/water bath and was quenched with 0.7 mL water and 8 mL NH$_4$Cl following equilibration. The quenched solution was then transferred to a separatory funnel, rinsing with water and toluene. After removing the organic layer, the aqueous layer was extracted with toluene (2×10 mL). Combined organics were washed with brine, dried over Na$_2$SO$_4$, filtered, and concentrated by rotary evaporation to afford a sticky white/yellow solid was allowed to dry overnight on high vac. The crude product was purified by normal phase column chromatography (4.5×9 cm silica gel column, isocratic 100% hexanes), affording the pure L3 as a white solid (251.4 mg, 0.7256 mmol, 67% yield).

$^1$H NMR (500 MHz, acetone-d6) δ 7.30-7.23 (m, 6H), 7.05 (m, 3H), 6.70 (m, 3H), 2.76 (dq, J=7.5, 1.2 Hz, 6H), 1.07 (t, J=7.5 Hz, 9H). $^{13}$C NMR (126 MHz, acetone-d6) δ 149.31 (d, J$_{C-P}$=25.7 Hz), 135.60 (d, J$_{C-P}$=11.6 Hz), 134.60, 130.06, 129.45 (d, J$_{C-P}$=5.0 Hz), 126.96, 28.19 (d, J$_{C-P}$=22.4 Hz), 15.69 (d, J$_{C-P}$=3.0 Hz). $^{31}$P NMR (202 MHz, acetone-d6, referenced to H$_3$PO$_4$ in D$_2$O) δ −35.62. Rf=0.31 on normal phase TLC in 100% hexanes. HRMS (ES$^+$) Calculated for C$_{24}$H$_{28}$P: 347.1929; Found: 347.1926.

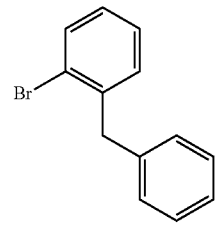 [SMILES: Brc1ccccc1Cc1ccccc1]

1-benzyl-2-bromobenzene SI-1

This procedure was based on a previous report of the selective coupling of benzylic bromides (Anselmi et al., *Synthesis* 2012, 44, 2023). While in an inert atmosphere glovebox, Pd(PPh$_3$)$_4$ (0.6933 g, 0.600 mmol, 2 mol %) was massed out into a stir bar-equipped, 3-neck 500 mL round bottom flask. The flask was sealed with three septa, brought out into a fume hood, and then equipped with a reflux condenser attached to a nitrogen inlet. After the system was put under nitrogen, additional reagents and solvents were added by briefly removing a septum while under a positive nitrogen pressure. In this manner, ethanol (48 mL, 0.63 Molar), water (13 mL, 2.3 Molar), toluene (58 mL, 0.52 Molar), 2-bromobenzyl bromide (7.498 g, 30.0 mmol, 1.00 eq), phenylboronic acid (3.66 g, 30.0 mmol, 1.00 eq), and an aqueous solution of sodium carbonate (3.58 g, 33.8 mmol, 1.13 eq in 34 mL H$_2$O) were added to the reaction.

The reaction was heated to 80° C. overnight and then filtered through celite. After concentration, the crude material was diluted with H$_2$O and extracted with Et$_2$O. Combined organics were washed with brine, dried with Na$_2$SO$_4$, decanted, and reconcentrated. The product was purified by normal phase column chromatography (100% hexanes) followed by vacuum distillation using a kugelrohr, giving aryl bromide SI-1 as a clear colorless oil (4.189 g, 16.95 mmol, 56% yield).

$^1$H NMR (500 MHz, CDCl$_3$) δ 7.57 (dd, J=8.0, 1.3 Hz, 1H), 7.30 (t, J=7.4 Hz, 2H), 7.25-7.18 (m, 4H), 7.14 (dd, J=7.6, 1.7 Hz, 1H), 7.09 (td, J=7.6, 1.7 Hz, 1H), 4.13 (s, 2H). $^{13}$C NMR (126 MHz, CDCl$_3$) δ 140.50, 139.60, 132.98, 131.21, 129.13, 128.60, 128.01, 127.58, 126.38, 125.03, 41.87.

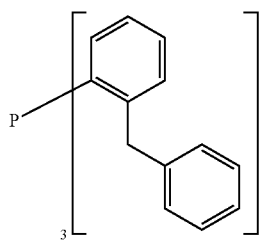

Tris(2-benzyl-phenyl)phosphine L4

A flame dried, 250 mL, 1 neck round bottom flask was equipped with a stir bar, sealed with a septum, and put under nitrogen. To a separate, flame-dried 40 mL vial was added 2-benzyl-1-bromobenzene (4.19 g, 16.95 mmol, 1.00 eq). The vial put under nitrogen, and THF (28 mL total) was used to transfer the aryl bromide to the reaction flask, with rinsing for quantitative transfer. The solution was cooled by submerging in a dry ice/acetone bath. To the −78° C. mixture was added n-butyllithium (1.6 Molar in hexanes, 9.5 mL, 15.3 mmol, 0.90 eq) dropwise over 5-10 minutes, causing the reaction to turn a cloudy brownish/yellow. The reaction was allowed to stir for 1.5 hours at −78° C. Phosphorus trichloride (0.37 mL, 0.582 g, 4.24 mmol, 0.25 eq) was added neat in a dropwise manner over 2-3 minutes. The reaction was allowed to gradually warm to room temperature and stirred overnight.

The next day, the reaction was quenched with NH$_4$Cl (40 mL). Water (80 mL) and DCM (120 mL) were added, and the aqueous layer was extracted (3×120 mL DCM). The combined organics were washed with brine (250 mL), dried (Na$_2$SO$_4$), decanted, and concentrated, giving a crude mixture consisting of a white solid and an oil. The crude product was purified by normal phase column chromatography (6 cm diameter, 500 mL SiO$_2$, isocratic 4/1 Hex/DCM), giving 1.96 grams of mostly pure product. This mixture was recrystallized from boiling hexanes (200-250 mL). After cooling to room temperature and then to 0° C., the product was filtered, giving L4 as a white crystalline powder (1.385 grams, 2.60 mmol, 61% yield).

$^1$H NMR (500 MHz, CDCl$_3$) δ 7.25 (td, J=7.3, 0.9 Hz, 3H), 7.14 (t, J=7.5 Hz, 6H), 7.12-7.06 (m, 9H), 7.02 (dd, J=7.0, 1.7 Hz, 6H), 6.82 (ddd, J=7.7, 4.0, 1.4 Hz, 3H), 4.09 (s, 6H). $^{13}$C NMR (126 MHz, CDCl$_3$) δ 145.78 (d, J$_{C-P}$=26.3 Hz), 140.73, 134.99 (d, J$_{C-P}$=11.7 Hz), 134.31, 130.13 (d, J$_{C-P}$=5.0 Hz), 129.44, 129.06, 128.27, 126.66, 125.94, 40.23 (d, J$_{C-P}$=22.3 Hz). $^{31}$P NMR (202 MHz, CDCl$_3$, referenced to H$_3$PO$_4$ in D$_2$O) δ −31.42 HRMS (EI$^+$) Calculated for C$_{39}$H$_{33}$P: 532.23199; Found: 532.23141.

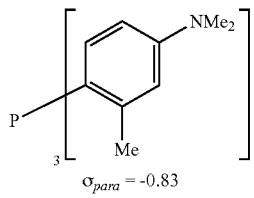

$\sigma_{para} = -0.83$

Tris(2-methyl-4-dimethylaminophenyl)phosphine L5

This procedure was based on previously reported synthesis of this compound (Heck et al., *J. Org. Chem.* 1977, 43 (15), 2941). A dry, stir bar-equipped 50 mL 3-neck round bottom flask was fitted with a reflux condenser and put under nitrogen. N,N,3-trimethylaniline (1.45 mL, 1.352 g, 10.0 mmol, 3.03 eq) was added, followed by pyridine (5.0 mL), resulting in a clear, homogeneous, slightly yellow solution. The mixture was cooled to 0° C., and phosphorus tribromide (0.31 mL, 0.901 g, 3.33 mmol, 1.00 eq) was added in a neat fashion dropwise over three or four minutes. The reaction immediately changed to a yellow color and precipitate began to gradually form. After five minutes of stirring at 0° C., the reaction was heated to 125° C. for one hour and then cooled to room temperature.

The crude reaction was diluted in benzene (50 mL) and washed with 6 N NaOH (20 mL), H$_2$O (20 mL), and brine (20 mL). The organic layer was dried with Na$_2$SO$_4$, decanted, and concentrated on strong vacuum to remove all solvent. The crude material was then transferred to a small round bottom flask (50 mL) and dissolved in degassed acetone. After heating to boiling and stirring, a white powder was present that still would not dissolve. The mixture was cooled to room temperature and filtered through a medium porosity glass frit. The filtrate was reconcentrated and triturated again, and this process was repeated once more. The combined crystals were triturated with acetone and filtered again, this time under nitrogen. The crystalline product L5 was crushed to a white powder and stored under inert atmosphere (0.233 g, 0.537 mmol, 16% yield).

$^1$H NMR (500 MHz, C$_6$D$_6$) δ 7.19 (dd, J=8.5, 4.2 Hz, 3H), 6.63 (t, J=3.4 Hz, 3H), 6.40 (dd, J=8.5, 2.7 Hz, 3H), 2.69 (s, 9H), 2.51 (s, 18H). $^{13}$C NMR (126 MHz, CDCl$_3$) δ 150.54, 143.32 (d, J=26.6 Hz), 134.36, 122.10 (d, J=6.3 Hz), 114.10 (d, J=5.0 Hz), 110.37, 40.46, 21.85 (d, J=21.0 Hz). $^{31}$P NMR (202 MHz, C$_6$D$_6$, referenced to H$_3$PO$_4$ in D$_2$O) δ −34.90. HRMS (ES$^+$) Calculated for C$_{27}$H$_{37}$N$_3$P: 434.2725; Found: 434.2714.

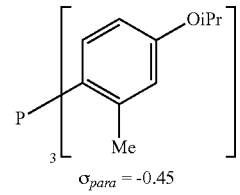

$\sigma_{para} = -0.45$

Tris(4-isopropoxy-2-methylphenyl)phosphine L6

A solution of 1-bromo-4-isopropoxy-2-methylbenzene (0.6874 g, 3.00 mmol, 1.00 eq) in dry THF (5.0 mL) in a three-neck, 100 mL round bottom flask was cooled to −78° C. before adding nbutyllithium (1.6 Molar in hexanes, 1.84 mL, 2.94 mmol, 0.98 eq) dropwise over five minutes. The reaction was allowed to stir for 1 hour and 45 minutes at −78° C., resulting in a cloudy, orange/sherbet-colored suspension. A solution of phosphorus trichloride (78 µL, 0.124 g, 0.90 mmol, 0.30 eq) in THF (2.0 mL) was added to the reaction dropwise over about five minutes. The resulting clear, homogeneous orange-colored reaction was stirred for 40 minutes at −78° C. and then allowed to warm to room temperature.

The reaction was quenched with saturated NH$_4$Cl (10 mL), and diluted with H$_2$O (20 mL) and DCM (30 mL). The aqueous layer was extracted with DCM (3×30 mL). The combined organics were washed with brine (100 mL), dried (MgSO$_4$), filtered, and concentrated to afford a viscous yellow oil. The crude product was purified by normal phase column chromatography (5 cm diameter, 200 mL silica gel, isocratic 30/1 Hex/EtOAc), giving L6 as a white powder (0.1876 g, 0.3920 mmol, 44% yield).

$^1$H NMR (500 MHz, C$_6$D$_6$) δ 7.08 (dd, J=8.4, 4.0 Hz, 3H), 6.88 (dd, J=4.0, 2.6 Hz, 3H), 6.59 (dd, J=8.4, 2.6 Hz, 3H), 4.20 (h, J=6.0 Hz, 3H), 2.50 (s, 9H), 1.11 (d, J=6.0 Hz, 18H). $^{13}$C NMR (126 MHz, CDCl$_3$) δ 158.44, 144.20 (d, J$_{C-P}$=27.4 Hz), 134.56, 126.11 (d, J$_{C-P}$=8.3 Hz), 117.77 (d, J=5.1 Hz), 112.99 (d, J=0.9 Hz), 69.61, 22.30, 21.49 (d, J=21.4 Hz). $^{31}$P NMR (202 MHz, C$_6$D$_6$, referenced to H$_3$PO$_4$ in D$_2$O) δ −33.72. Rf=0.20 on normal phase TLC in 20/1 Hex/EtOAc. HRMS (ES$^+$) Calculated for C$_{30}$H$_{40}$O$_3$P: 479.2715; Found: 479.2710.

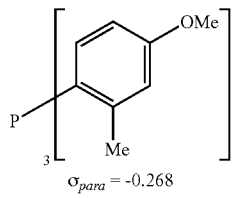

Tris(4-methoxy-2-methylphenyl)phosphine L7

This compound has been previously synthesized and characterized (Moore et al., *Organic letters* 2004, 6 (2), 225). A dry, stir bar-equipped 100 mL recovery flask was charged with magnesium turnings (0.3975 g, 16.35 mmol, 1.01 eq) in an inert atmosphere glovebox. The flask was sealed with a septum, brought out into the hood, equipped with a reflux condenser, attached to a Schlenk line, and put under nitrogen. Dry THF (8 mL) was added, followed by 1-bromo-4-methoxy-2-methylbenzene (2.29 mL, 3.26 g, 16.2 mmol, 1.00 eq) dropwise over eight minutes. An additional 8 mL of dry THF was added. The reaction began to reflux without any external heat or initiating agent. In a separate round bottom flask, a solution of phosphorus trichloride (0.44 mL, 0.69 g, 5.0 mmol, 0.31 eq) in dry THF (14 mL) was prepared under nitrogen. After the Grignard had turned to a cloudy grey and most of the magnesium was gone (about one hour), the solution of phosphorus trichloride was added at 0° C. dropwise over 10 minutes. The reaction was allowed to warm to room temperature and stirred overnight.

The next day, the reaction was quenched with addition of saturated NH$_4$Cl (40 mL) and diluted with H$_2$O (80 mL) and toluene (100 mL). The aqueous layer was extracted with toluene (3×100 mL), and the combined organics were washed with brine, dried with MgSO$_4$, filtered, and concentrated. The crude product was purified by column chromatography (4 cm diameter, 130 mL silica gel, 30/1 Hex/EtOAc), giving L7 as a white powder (0.4652 g, 1.179 mmol, 24% yield).

$^1$H NMR (500 MHz, CDCl$_3$) δ 6.78 (m, 3H), 6.65-6.62 (m, 6H), 3.79 (s, 9H), 2.36 (s, 3H). $^{13}$C NMR (126 MHz, CDCl$_3$) δ 160.13, 144.23 (d, J$_{C-P}$=27.6 Hz), 134.53, 126.37 (d, J$_{C-P}$=8.5 Hz), 116.02 (d, J=5.2 Hz), 111.60 55.20, 21.49 (d, J=21.4 Hz). $^{31}$P NMR (202 MHz, C$_6$D$_6$, referenced to H$_3$PO$_4$ in D$_2$O) δ −33.95. HRMS (EI$^+$) Calculated for C$_{24}$H$_{27}$O$_3$P: 394.16979; Found: 394.16897.

Tris(2,4-dimethylphenyl)phosphine L8

This ligand was purchased from Sigma-Aldrich (Product number 710547, Lot number MKBB9858V).

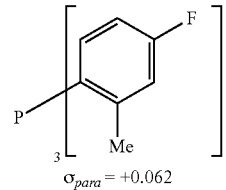

Tris(4-fluoro-2-methylphenyl)phosphine L9

A dry, stir bar-equipped 25 mL three neck round bottom flask was charged with magnesium turnings (0.1535 g, 6.314 mmol, 1.05 eq) in an inert atmosphere glovebox. The flask was sealed with septa, brought out into the hood, equipped with a reflux condenser, attached to a Schlenk line, and put under nitrogen. To a separate 10 mL pear flask under nitrogen was added 1-bromo-4-fluoro-2-methylbenzene (0.76 mL, 1.136 g, 6.011 mmol, 1.00 eq) and dry THF (6.0 mL). This solution was added in a dropwise fashion to the magnesium-containing flask, causing initiation of the Grignard reaction. After about 1.5 hours, the reaction had turned cloudy and a brownish/grey color and cooled to room temperature. The Grignard was added to a −78° C. solution of phosphorus trichloride (0.155 mL, 0.243 g, 1.77 mmol, 0.295 eq) in THF (5.0 mL) in a 50 mL pear flask. The reaction was allowed to gradually warm to room temperature and stir overnight.

The next day, the reaction was cooled to 0° C. and quenched with addition of saturated NH$_4$Cl (20 mL) and diluted with H$_2$O (10 mL) and toluene (30 mL). The aqueous layer was extracted with toluene (3×30 mL), and the combined organics were washed with brine, dried with MgSO$_4$, filtered, and concentrated. The crude product was purified by normal phase column chromatography (2.5 cm diameter, 40 mL silica gel, isocratic 3/1 Hex/DCM, then a second column of same dimensions with isocratic 100% hexanes), giving L9 as a white powder (0.2611 g, 0.7286 mmol, 41% yield).

$^1$H NMR (500 MHz, CDCl$_3$) δ 6.96 (dt, J=9.8, 3.3 Hz, 3H), 6.80 (td, J=8.5, 2.7 Hz, 3H), 6.64 (ddd, J=8.6, 6.3, 3.7 Hz, 3H), 2.36 (s, 9H). $^{13}$C NMR (126 MHz, CDCl$_3$) δ 163.58 (d, J$_{C-F}$=248.5 Hz), 145.35 (dd, J=28.4, 7.8 Hz), 134.83 (d, J=8.1 Hz), 129.66 (dd, J=10.6, 3.2 Hz), 117.45 (dd, J=20.7, 5.1 Hz), 113.45 (d, J=20.2 Hz), 21.31 (dd, J=21.8, 1.6 Hz). $^{31}$P NMR (202 MHz, C$_6$D$_6$, referenced to H$_3$PO$_4$ in D$_2$O) δ −33.00 (q, J=3.5 Hz). $^{19}$F NMR (470 MHz, CDCl$_3$, referenced to CFCl$_3$ in CDCl$_3$) δ −114.60 (q, J=8.3 Hz). HRMS (EI$^+$) Calculated for C$_{21}$H$_{18}$F$_3$P: 358.10982; Found: 358.10935.

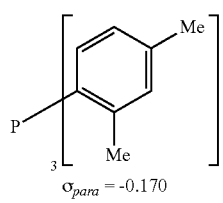

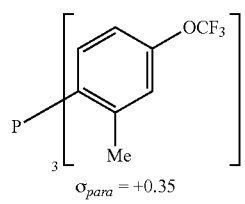

Tris(2-methyl-4-(trifluoromethoxy)phenyl)phosphine L10

Caution: the synthesis of these ligands through the arylmagnesium species is potentially hazardous. A solution of 1-bromo-2-methyl-4-(trifluoromethoxy)benzene (0.82 mL, 1.28 g, 5.00 mmol, 1.00 eq) in dry THF (8.0 mL) in a three-neck, 100 mL round bottom flask was cooled to −78° C. before adding nbutyllithium (1.6 Molar in hexanes, 2.97 mL, 4.75 mmol, 0.95 eq). The resulting homogeneous, clear, slightly orange solution was allowed to stir for 1.5 hours at −78° C. A solution of phosphorus trichloride (125 µL, 0.196 g, 1.43 mmol, 0.285 eq) in THF (3.0 mL) was added to the reaction dropwise over about three minutes. The resulting clear, homogeneous orange/red-colored reaction was stirred for five hours at −78° C. and then allowed to warm to room temperature.

The reaction was quenched with saturated $NH_4Cl$ (10 mL) and diluted with $H_2O$ (20 mL) and toluene (30 mL). The aqueous layer was extracted with toluene (3×30 mL). The combined organics were washed with brine (100 mL), dried ($MgSO_4$), filtered, and concentrated. The crude product was purified by normal phase column chromatography (4 cm diameter, 150 mL silica gel, isocratic 100% hexanes), giving L10 as a white powder (0.4389 g, 0.7889 mmol, 55% yield).

$^1$H NMR (500 MHz, $CDCl_3$) δ 7.11 (s, 3H), 6.97 (d, J=8.4 Hz, 3H), 6.69 (dd, J=8.4, 3.7 Hz, 3H), 2.39 (s, 9H). $^{13}$C NMR (126 MHz, $CDCl_3$) δ 150.22 (q, $J_{C-F}$=1.8 Hz), 145.10 (d, $J_{C-P}$=28.3 Hz), 134.52, 132.25 (d, $J_{C-P}$=11.5 Hz), 122.53 (d, $J_{C-P}$=5.0 Hz), 120.59 (q, $J_{C-F}$=258.0 Hz), 118.53, 21.39 (d, $J_{C-P}$=21.7 Hz). $^{31}$P NMR (202 MHz, $C_6D_6$ referenced to $H_3PO_4$ in $D_2O$) δ −32.12. $^{19}$F NMR (470 MHz, $C_6D_6$, referenced to $CFCl_3$ in $CDCl_3$) δ −57.79. Rf=0.29 on normal phase TLC in 100% hexanes. HRMS (ES$^+$) Calculated for $C_{24}H_{19}O_3F_9P$: 557.0928; Found: 557.0918.

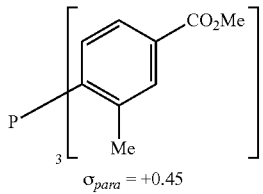

$\sigma_{para}$ = +0.45

Trimethyl 4,4',4''-phosphanetriyltris(3-methylbenzoate) L11

This synthesis was based on a procedure previously reported for the corresponding phosphine lacking the ortho-methyl groups (Gall et al., *Synlett* 2006, 6, 0954). To a dry, 100 mL 3-neck round bottom flask were added $CoBr_2$ (0.1094 g, 0.50 mmol, 0.10 eq), zinc (1.092 g, 16.7 mmol, 3.33 eq), and $ZnBr_2$ (0.1126 g, 0.50 mmol, 0.10 eq). The mixture was crushed to a fine powder and then heated at 160° C. for two hours on high vac while the stir bar agitated the powder. Upon cooling to room temperature, MeCN (5.0 mL) was added, resulting in a blue suspension. Trifluoroacetic acid (17 µL, 25 mg, 0.22 mmol, 4.4 mol %) was added, resulting in a grey suspension.

Separately, a solution of methyl 4-bromo-3-methylbenzoate (1.145 g, 5.00 mmol, 1.00 eq) in MeCN (3.0 mL) was prepared under nitrogen in a 10 mL recovery flask. A small amount of the aryl bromide solution (about 0.2 mL) was added to the zinc suspension and allowed to stir for 25 minutes at room temperature. The remainder of the aryl bromide solution was then added (dropwise over five minutes at room temperature, with rinsing 2×0.5 mL of MeCN for quantitative transfer).

After stirring at room temperature for 1 hour and 35 minutes, the reaction was monitored by NMR. A small aliquot (0.2 mL) was removed via needle and added to a solution of iodine in pentane. The vial was capped and shaken, and then 3 mL of saturated $Na_2S_2O_3$. The organic layer was removed, concentrated, and analyzed by $^1$H-NMR in $C_6D_6$. No aryl bromide remained (complete conversion). There was approximately 75% of the aryl iodide and 25% protodehalogenated side product.

The arylzinc solution was filtered by the following procedure. First, a dry, stir bar-equipped 100 mL Schlenk flask was put under nitrogen. The arylzinc was drawn into a 24 mL syringe through a needle. The needle was then quickly removed and replaced with a dry 0.2 micron HPLC filter with a needle on the end. The aryl was pushed through the filter and the needle into the receiving Schlenk flask.

To this room temperature stirring solution was added phosphorus trichloride (110 µL, 0.173 g, 1.25 mmol, 0.33 eq relative to the arylzinc as read out by NMR yield of the aryl iodide). During the addition, the reaction changed from an orange homogeneous solution to a yellow cloudy suspension. After the addition was complete, the reaction was heated to 45° C. with vigorous stirring.

After one hour, the reaction was monitored by NMR. A small aliquot was removed, quenched by 1 M HCl, extracted with DCM, and concentrated. Only traces of product had formed, with most material converted to the protodehalogenated side product. The reaction was then heated to 65° C. and allowed to stir overnight.

After 13 hours, the reaction was again monitored by NMR. Two aliquots were removed. One was quenched with 1 M HCl (to check for product formation), and the other was quenched with iodine (to check for consumption of the arylzinc reagent). By NMR analysis, there was a 5:5:1 ratio of arylzinc/protodehalogenated side product/triarylphosphine product. To accelerate the reaction by enhancing the nucleophilicity of the arylzinc reagent, anhydrous lithium bromide (0.436 g, 5.00 mmol, 1.00 eq relative to original ArBr) in THF was added in one portion. The reaction changed from a pale, cream-colored suspension to an opaque, green/blue suspension. After another hour, the reaction was monitored by NMR using the same dual aliquot procedure. It was approximately 3:3:1 arylzinc/protodehalogenated side product/triarylphosphine product. The reaction was allowed to continue stirring at 65° C. for another three hours and then cooled to room temperature. The reaction was quenched with 1 Molar HCl (30 mL) and extracted with DCM (3×30 mL). The combined organics were washed with $H_2O$ (100 mL) and brine (100 mL), dried with $Na_2SO_4$, decanted, and concentrated. The crude material was dried on high vac overnight.

The next day, the crude reaction was purified by normal phase column chromatography (6 cm diameter, 200 mL silica gel, isocratic 6/1 Hex/EtOAc), giving L11 as a white solid (64.6 mg, 0.135 mmol, 11% yield).

$^1$H NMR (500 MHz, $C_6D_6$) δ 8.00 (ddd, J=4.7, 1.1, 0.5 Hz, 3H), 7.81 (ddd, J=7.9, 1.2, 0.4 Hz, 3H), 6.86 (dd, J=7.9, 3.9 Hz, 3H), 3.50 (s, 9H), 2.24 (s, 9H). $^{13}$C NMR (126 MHz, $CDCl_3$) δ 167.10, 143.19 (D, $J_{C-P}$=26.5 Hz), 139.42 (d, $J_{C-P}$=12.8 Hz), 133.11, 131.18 (d, $J_{C-P}$=4.9 Hz), 131.00, 127.34, 52.37, 21.30 (d, $J_{C-P}$=21.1 Hz). $^{31}$P NMR (202 MHz, $C_6D_6$ referenced to $H_3PO_4$ in $D_2O$) δ −27.25. Rf=0.16 on normal phase TLC in 6/1 Hex/EtOAc. HRMS (ES+) Calculated for $C_{27}H_{28}O_6P$: 479.1624; Found: 479.1614.

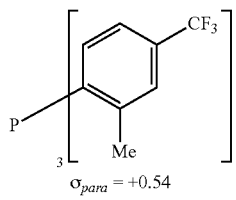

Tris(2-methyl-4-(trifluoromethyl)phenyl)phosphine L12

Caution: the synthesis of these ligands through the arylmagnesium species is potentially hazardous. A dry, stir bar-equipped, 50 mL 3-neck round bottom flask was put under nitrogen before adding 1-bromo-2-methyl-4-(trifluoromethyl)benzene (1.21 g, 5.00 mmol, 1.00 eq) and dry THF (8.3 mL). The stirring solution as cooled to −78° C. in a dry ice/acetone bath. n-Butyllithium (1.6 Molar in hexanes, 3.1 mL, 4.96 mmol, 0.99 eq) was added dropwise over 10 minutes, resulting in a green/grey solution. Over the next hour of stirring at −78° C., the reaction color changed from green to yellow, to orange, and finally to dark red. After one hour and 15 minutes, a solution of phosphorus trichloride (0.131 mL, 0.206 g, 1.50 mmol, 0.30 eq) in THF (2.5 mL) was added dropwise over five minutes. The resulting dark red-colored reaction was allowed to stir and gradually warm to room temperature over the next seven hours.

The reaction was cooled to 0° C. and quenched by addition of $H_2O$ (0.8 mL) while under nitrogen. The septum was then removed, and saturated $NH_4Cl$ (10 mL) was added. The reaction was diluted using $H_2O$ (20 mL) and toluene (20 mL). After extraction of the aqueous layer (3×30 mL toluene), the combined organics were washed with brine (100 mL), dried ($MgSO_4$), filtered, and concentrated to afford a mixture of a yellow oil and white crystalline product. The crude reaction was purified by normal phase column chromatography (150 mL silica gel, isocratic 100% hexanes). The ligand was further purified via recrystallization by dissolving in a minimal amount of boiling MeOH, cooling to 0° C., and filtering, giving L12 a white crystalline product (0.2615 g, 0.5144 mmol, 34% yield).

$^1$H NMR (500 MHz, $C_6D_6$) δ 7.27 (d, J=3.9 Hz, 3H), 7.01 (d, J=8.2 Hz, 3H), 6.54 (dd, J=8.0, 3.8 Hz, 3H), 2.05 (s, 9H). $^{13}$C NMR (126 MHz, CDCl$_3$) δ 143.80 (d, $J_{C-P}$=27.3 Hz), 137.83 (d, $J_{C-P}$=12.9 Hz), 133.39, 131.64 (q, $J_{C-F}$=32.3 Hz), 127.12 (p, J=3.9 Hz), 124.12 (q, $J_{C-F}$=272.8 Hz), 123.30 (q, $J_{C-F}$=3.8 Hz), 21.39 (d, J=21.3 Hz). $^{31}$P NMR (202 MHz, $C_6D_6$ referenced to $H_3PO_4$ in $D_2O$) δ −28.47. $^{19}$F NMR (470 MHz, $C_6D_6$ referenced to CFCl$_3$ in CDCl$_3$) δ −62.99. HRMS (EI+) Calculated for $C_{24}H_{18}F_9P$: 508.10021; Found: 508.09941.

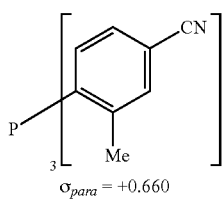

4,4',4''-phosphanetriyltris(3-methylbenzonitrile) L13

To a dry 50 mL, 3-neck, stir bar-equipped round bottom flask was added 4-bromo-3-methylbenzonitrile (0.9803 g, 5.00 mmol, 1.00 eq). The aryl bromide was put under nitrogen, dry THF (5.0 mL) was added, and the stirring solution was cooled to 0° C. in an ice/water bath. i-PrMgCl*LiCl (1.3 Molar in THF, 3.85 mL, 5.00 mmol, 1.00 eq) was added (dropwise over 20 minutes), causing the reaction appearance to change to a cloudy, dark yellow. The reaction was allowed to continue stirring at 0° C. The reaction was monitored by NMR by removing a small aliquot and reacting with a mixture of iodine in pentane. After quenching with saturated $Na_2S_2O_4$, the organic layer was separated and concentrated. $^1$H NMR was used to quantify the aryl iodide (as a readout for the reactive organometallic reagent), remaining aryl bromide, and protodehalogenated side product.

1 hour and 40 minutes: 10% ArI, 58% ArBr, 32% ArH.
3 hours and 55 minutes: 28% ArI, 40% ArBr, 32% ArH.
6 hours and 50 minutes: 48% ArI, 31% ArBr, 21% ArH.

After seven hours, the reaction was cooled to −78° C. in a dry ice/acetone bath. Phosphorus trichloride (50 µL, 0.0785 g, 0.572 mmol, 0.24 eq relative to aryl Grignard as readout by NMR yield of corresponding aryl iodide) was added (neat, dropwise over 2 minutes). The reaction changed from an orange cloudy appearance to a yellow cloudy appearance. The reaction was allowed to warm to room temperature and stir overnight. Nine hours later, the crude reaction was filtered through celite (20 mL), rinsing with DCM (100 mL). The filtrate was concentrated to give a viscous orange oil. The crude product was purified by normal phase column chromatography (5 cm diameter, 300 mL silica gel, isocratic 8/1 Hex), giving L13 as a white powder (40.4 mg, 0.106 mmol, 19% yield).

$^1$H NMR (500 MHz, $C_6D_6$) δ 6.80-6.76 (m, 6H), 6.27 (dd, J=8.0, 3.8 Hz, 3H), 1.86 (s, 9H). $^{13}$C NMR (126 MHz, CDCl$_3$) δ 144.23 (d, $J_{C-P}$=27.5 Hz), 138.77 (d, $J_{C-P}$=14.5 Hz), 133.71 (d, J=4.7 Hz), 133.43, 130.11, 118.40, 113.81, 21.20 (d, J=21.4 Hz). $^{31}$P NMR (202 MHz, $C_6D_6$ referenced to $H_3PO_4$ in $D_2O$) δ −26.84. HRMS (ES+) Calculated for $C_{24}H_{19}N_3P$: 380.1317; Found: 380.1301.

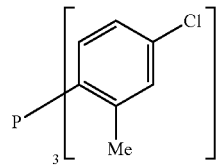

Tris(4-chloro-2-methylphenyl)phosphine SI-2

A dry, stir bar-equipped 50 mL Schlenk flask was sealed with a rubber septum and vac-filled with nitrogen three times. In a separate dry 40 mL vial, 2-bromo-5-chlorotoluene (2.055 g, 10.0 mmol, 1.00 eq) was massed out. The vial was likewise put under nitrogen, and dry THF (16.7 mL total, 0.60 Molar) was used to transfer the aryl bromide to the Schlenk flask. The solution was cooled with stirring to −78° C. in a dry ice/acetone bath. To this stirring solution was added n-butyllithium (1.6 Molar in hexanes, 5.6 mL, 9.0 mmol, 0.90 eq, dropwise over 10 minutes), causing a change in the reaction appearance from clear/colorless to opaque/cream-colored. After stirring at −78° C. for 1 hour and 50 minutes, PCl₃ (0.218 mL, 0.343 g, 2.50 mmol, 2.50 eq) was added (neat, dropwise over 3-4 minutes). The now opaque orange suspension was allowed to gradually warm to room temperature with stirring.

Two days later, the reaction was quenched by addition of saturated NH₄Cl. The mixture was diluted with H₂O and extracted with DCM three times. Combined organics were washed with brine, dried with Na₂SO₄, and concentrated by rotary evaporation. The crude black oil was filtered through a pad of silica gel rinsing with 5/1 Hex/DCM, giving a light yellow oil. This material was purified by column chromatography (4 cm diameter, 120 mL SiO2, isocratic 100% hexanes, giving SI-2 as a fluffy white solid (276.0 mg=0.6781 mmol=27% yield).

¹H NMR (500 MHz, CDCl₃) δ 7.24 (dd, J=4.1, 2.0, 3H), 7.07 (dd, J=8.2, 2.2 Hz, 3H), 6.59 (dd, J=8.2, 3.8 Hz, 3H), 2.34 (s, 9H). ¹³C NMR (126 MHz, CDCl₃) δ 144.58 (d, J=27.8 Hz), 135.34, 134.27, 132.17 (d, J=11.4 Hz), 130.42 (d, J=4.9 Hz), 126.68, 21.13 (d, J=21.5 Hz). ³¹P NMR (202 MHz, C₆D₆ referenced to H₃PO₄ in D₂O) δ −31.64. $R_f$=0.27 on normal phase TLC in 100% hexanes. HRMS (EI⁺) Calculated for $C_{21}H_{18}Cl_3P$: 406.02121; Found: 406.02040.

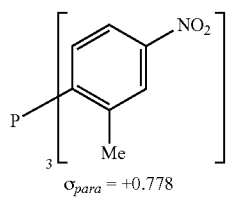

Tris(2-methyl-4-nitrophenyl)phosphine L14

Sodium nitrite was dried under high vacuum in 80° C. sand bath, and tert-amyl alcohol was degassed by bubbling nitrogen through for 20 min. A dry, stir bar-equipped, 15 mL pressure tube was brought into an inert atmosphere glovebox and charged with sodium nitrite (0.24877 g, 3.606 mmol, 6.00 eq), tris(4-chloro-2-methylphenyl)phosphine (0.2450 g, 0.6009 mmol, 1.00 eq), Pd₂dba₃ (41.1 mg, 0.0449 mmol, 7.5 mol %), and tBuBrettPhos (52.2 mg, 0.108 mmol, 18 mol %). tert-amyl alcohol (4.0 mL) and tris[2-(2-methoxyethoxy)ethyl]amine (28.8 μL, 29.1 mg, 0.0900 mmol, 0.15 eq) were added, and the pressure tube was tightly capped. The reaction was brought out of the glovebox and into a fume hood, where it was stirred for 72 hours at 140° C.

The catalyst was removed by silica gel filtration (diluting with 100 mL EtOAc). The crude product was then purified by normal phase column chromatography (70 g silica gel, 3.5×15 cm, dry loading on celite, 50:1 to 20:1 Hex/EtOAc), giving L14 as a yellow powder (74.1 mg, 0.169 mmol, 28% yield).

¹H NMR (500 MHz, C₆D₆) δ 8.16 (dd, J=4.4, 2.4 Hz, 3H), 7.97 (dd, J=8.4, 2.3 Hz, 3H), 6.84 (dd, J=8.4, 3.5 Hz, 3H), 2.50 (s, 9H). ¹³C NMR (126 MHz, CDCl₃) δ 149.12, 144.88 (d, $J_{C-P}$=28.2 Hz), 140.68 (d, $J_{C-P}$=14.5 Hz), 133.82, 125.23 (d, $J_{C-P}$=4.9 Hz), 121.51, 21.55 (d, $J_{C-P}$=21.2 Hz). ³¹P NMR (202 MHz, CDCl₃ referenced to H₃PO₄ in D₂O) δ −26.72. HRMS (ES⁺) Calculated for $C_{21}H_{18}N_3O_6P$: 439.0933; Found: 439.0932.

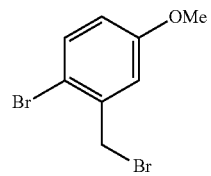 [SMILES: COc1ccc(Br)c(CBr)c1]

1-bromo-2-(bromomethyl)-4-methoxybenzene SI-3

A dry, stir bar-equipped, 3-neck 250 mL round bottom flask was fitted with a reflux condenser and put under nitrogen. 1-bromo-4-methoxy-2-methylbenzene (1.39 mL, 2.011 g, 10.0 mmol, 1.00 eq), CCl₄ (20.0 mL, 0.50 Molar, not degassed), N-bromosuccinimide (recrystallized, 2.67 g, 15.0 mmol, 1.50 eq), and benzoyl peroxide (0.121 g, 0.50 mmol, 5 mol %) were added by briefly removing a septum while under positive nitrogen pressure. The reaction was heated to reflux for 18 hours.

The next day, the reaction was filtered through a silica gel plug, rinsing with 10/1 Hex/Et₂O. The crude product was purified by normal phase column chromatography (5 cm diameter, 300 mL silica gel, isocratic 4/1 Hex/DCM), giving SI-3 as a fluffy, slightly off-white powder (1.404 g, 5.015 mmol, 50% yield).

¹H NMR (500 MHz, CDCl₃) δ 7.45 (d, J=8.8 Hz, 1H), 6.99 (d, J=3.0 Hz, 1H), 6.74 (dd, J=8.8, 3.0 Hz, 1H), 4.56 (s, 2H), 3.80 (s, 3H). ¹³C NMR (126 MHz, CDCl₃) δ 159.28, 137.90, 134.06, 116.67, 116.27, 114.85, 55.71, 33.61. HRMS (EI⁺) Calculated for $C_8H_8OBr_2$: 277.89422; Found: 277.89402.

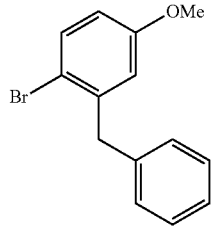 [SMILES: COc1ccc(Br)c(Cc2ccccc2)c1]

2-benzyl-1-bromo-4-methoxybenzene SI-4

This procedure was based on a previous report of the selective coupling of benzylic bromides. A stir bar-equipped, 3-neck 250 mL round bottom flask was sealed with two septa and equipped with a reflux condenser attached to a nitrogen inlet. After the system was put under nitrogen, reagents and solvents were added by briefly removing a septum while under a positive nitrogen pressure. In this manner, phenylboronic acid (0.5990 g, 4.913 mmol, 1.00 eq), ethanol (7.8 mL, 0.63 Molar), water (2.1 mL, 2.3 Molar), 1-bromo-2-(bromomethyl)-4-methoxybenzene (1.376 g, 4.913 mmol, 1.00 eq) as a solution in toluene (9.5 mL, 0.52 Molar), aqueous sodium carbonate (5.53 mL, 1.00 Molar, 5.53 mmol, 1.13 eq), and Pd(PPh₃)₄ (0.1135 g, 0.09826 mmol, 2 mol %) were added to the reaction.

The reaction was heated to 80° C. for 12 hours and then filtered through celite, rinsing with Et₂O. After concentration, the crude material was diluted with H₂O (30 mL) and extracted with Et₂O (3×30 mL). Combined organics were washed with brine (100 mL), dried with Na₂SO₄, decanted, and reconcentrated. The crude product was purified by normal phase column chromatography (5 cm diameter, 300 mL silica gel, isocratic 4/1 Hex/DCM), giving SI-4 as a clear colorless oil (0.7136 g, 2.575 mmol, 52% yield).

$^1$H NMR (500 MHz, CDCl$_3$) δ 7.45 (d, J=8.6 Hz, 1H), 7.30 (t, J=7.4 Hz, 2H), 7.24-7.18 (m, 3H), 6.68 (d, J=3.0 Hz, 1H), 6.66 (dd, J=8.6, 3.1 Hz, 1H), 4.07 (s, 2H), 3.73 (s, 3H). $^{13}$C NMR (126 MHz, CDCl$_3$) δ 159.06, 141.46, 139.43, 133.42, 129.09, 128.61, 126.42, 117.07, 115.44, 113.44, 55.49, 42.01. R$_f$=0.27 on normal phase TLC in 4/1 Hex/DCM. HRMS (EI$^+$) Calculated for C$_{14}$H$_{13}$OBr: 276.01498; Found: 276.01453.

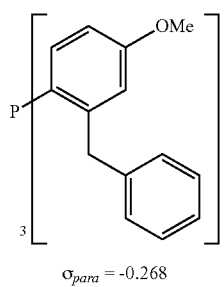

σ$_{para}$ = -0.268

Tris(2-benzyl-4-methoxyphenyl)phosphine L15

A flame dried, 25 mL recovery flask was equipped with a stir bar, sealed with a septum, and put under nitrogen. To a separate, flame-dried 40 mL vial was added 2-benzyl-1-bromo-4-methoxybenzene (0.6762 g, 2.44 mmol, 1.00 eq). The vial put under nitrogen, and THF (4.1 mL total) was used to transfer the aryl bromide to the reaction flask, with rinsing for quantitative transfer. The solution was cooled by submerging in a dry ice/acetone bath. To the -78° C. mixture was added n-butyllithium (1.6 Molar in hexanes, 1.37 mL, 2.20 mmol, 0.90 eq) dropwise over 5-10 minutes. The reaction was allowed to stir for 1.5 hours at -78° C. Phosphorus trichloride (53.2 μL, 83.8 mg, 0.610 mmol, 0.25 eq) was added neat in a dropwise manner over 2-3 minutes. The reaction was allowed to gradually warm to room temperature and stirred overnight.

The next day, the reaction was quenched with NH$_4$Cl (10 mL). Water (20 mL) and DCM (30 mL) were added, and the aqueous layer was extracted (3×30 mL DCM). The combined organics were washed with brine (100 mL), dried (Na$_2$SO$_4$), decanted, and concentrated. The crude product was purified by normal phase column chromatography (3 cm diameter, 120 mL SiO$_2$, isocratic 1/1 Hex/DCM), giving L15 as a white powder (0.2932 g, 0.471 mmol, 77% yield).

$^1$H NMR (500 MHz, CDCl$_3$) δ 7.14 (t, J=7.2 Hz, 6H), 7.08 (t, J=7.2 Hz, 3H), 7.02 (d, J=7.0 Hz, 6H), 6.74 (dd, J=8.8, 3.6 Hz, 3H), 6.65-6.61 (m, 6H), 4.05 (s, 6H), 3.72 (s, 9H). $^{13}$C NMR (126 MHz, CDCl$_3$) δ 160.26, 147.19 (d, J$_{C-P}$=27.8 Hz), 140.58, 135.56, 129.39, 128.26, 126.62 (d, J$_{C-P}$=9.3 Hz), 125.91, 116.13 (d, J$_{C-P}$=5.3 Hz), 111.82, 55.16, 40.21 (d, J$_{C-P}$=22.2 Hz). $^{31}$P NMR (202 MHz, CDCl$_3$, referenced to H$_3$PO$_4$ in D$_2$O) δ -35.94. HRMS (EI$^+$) Calculated for C$_{42}$H$_{39}$O$_3$P: 622.2637; Found: 622.2643.

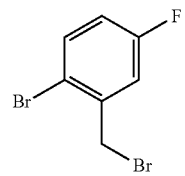

1-bromo-2-(bromomethyl)-4-fluorobenzene SI-5

A dry, stir bar-equipped, 3-neck 300 mL round bottom flask was fitted with a reflux condenser and put under nitrogen. 1-bromo-4-fluoro-2-methylbenzene (1.26 mL, 1.890 g, 10.0 mmol, 1.00 eq), CCl$_4$ (20.0 mL, 0.50 Molar, not degassed), N-bromosuccinimide (recrystallized, 2.67 g, 15.0 mmol, 1.50 eq), and benzoyl peroxide (0.121 g, 0.50 mmol, 5 mol %) were added by briefly removing a septum while under positive nitrogen pressure. The reaction was heated to reflux for 18 hours.

The next day, the reaction was filtered through a silica gel plug, rinsing with hexanes. The crude product was purified by normal phase column chromatography (5 cm diameter, 300 mL silica gel, isocratic 100% hexanes), giving SI-5 (1.219 g, 4.55 mmol, 45% yield).

$^1$H NMR (500 MHz, C$_6$D$_6$) δ 7.53 (dd, J=8.8, 5.2 Hz, 1H), 7.20 (dd, J=8.8, 3.0 Hz, 1H), 6.92 (ddd, J=8.8, 7.8, 3.0 Hz, 1H), 4.54 (s, 2H). $^{13}$C NMR (126 MHz, CDCl$_3$) δ 161.94 (d, J$_{C-F}$=248.1 Hz), 138.96 (d, J$_{C-F}$=7.6 Hz), 134.67 (d, J$_{C-F}$=7.8 Hz), 118.62 (d, J$_{C-F}$=3.4 Hz), 118.27 (d, J$_{C-F}$=23.6 Hz), 117.48 (d, J$_{C-F}$=22.3 Hz), 32.59 (d, J$_{C-F}$=1.6 Hz). $^{19}$F NMR (470 MHz, CDCl$_3$, referenced to CFCl$_3$ in CDCl$_3$) δ -114.28. HRMS (EI$^+$) Calculated for C$_7$H$_5$Br$_2$F: 265.87423; Found: 265.87446.

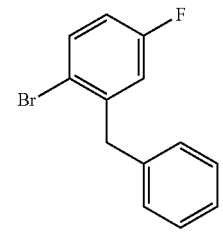 [SMILES: Fc1ccc(Br)c(Cc2ccccc2)c1]

2-benzyl-1-bromo-4-fluorobenzene SI-6

This procedure was based on a previous report of the selective coupling of benzylic bromides. A stir bar-equipped, 3-neck 300 mL round bottom flask was sealed with two septa and equipped with a reflux condenser attached to a nitrogen inlet. After the system was put under nitrogen, reagents and solvents were added by briefly removing a septum while under a positive nitrogen pressure. In this manner, phenylboronic acid (0.5548 g, 4.550 mmol, 1.00 eq), ethanol (7.1 mL, 0.63 Molar), water (2.0 mL, 2.3 Molar), 1-bromo-2-(bromomethyl)-4-fluorobenzene (1.219 g, 4.550 mmol, 1.00 eq) as a solution in toluene (8.75 mL, 0.52 Molar), aqueous sodium carbonate (5.12 mL, 1.00 Molar, 5.12 mmol, 1.13 eq), and Pd(PPh$_3$)$_4$ (0.1052 g, 0.0910 mmol, 2 mol %) were added to the reaction.

The reaction was heated to 80° C. for 12 hours and then filtered through celite, rinsing with Et$_2$O. After concentration, the crude material was diluted with H$_2$O (30 mL) and extracted with Et$_2$O (3×30 mL). Combined organics were washed with brine (100 mL), dried with Na$_2$SO$_4$, decanted, and reconcentrated. The crude product was purified by normal phase column chromatography (5 cm diameter, 300 mL silica gel, isocratic 100% hexanes) followed by reverse phase column chromatography (3 cm diameter, 50 mL C18 silica gel, isocratic 3/1 MeCN/H$_2$O, extracting with 4×100 mL pentane and drying with Na$_2$SO$_4$), giving SI-6 as a clear colorless oil (0.5966 g, 2.250 mmol, 49% yield).

$^1$H NMR (500 MHz, CDCl$_3$) δ 7.52 (m, 1H), 7.32 (m, 2H), 7.25 (m, 1H), 7.19 (d, J=7.4 Hz, 2H), 6.85-6.79 (m, 2H), 4.08 (s, 2H). $^{13}$C NMR (126 MHz, CDCl$_3$) δ 162.11 (d, J$_{C-F}$=246.5 Hz), 142.75 (d, J$_{C-F}$=7.1 Hz), 138.73, 133.97 (d, J$_{C-F}$=7.9 Hz), 129.18, 128.78, 126.72, 118.93 (d, J$_{C-F}$=3.3 Hz), 118.01 (d, J$_{C-F}$=23.0 Hz), 115.16 (d, J$_{C-F}$=22.5 Hz), 41.94 (d, J$_{C-F}$=1.4 Hz). $^{19}$F NMR (470 MHz, CDCl$_3$, referenced to CFCl$_3$ in CDCl$_3$) δ -115.30. R$_f$=0.25 on reverse phase TLC in 3/1 MeCN/H$_2$O. HRMS (EI$^+$) Calculated for C$_{13}$H$_{10}$BrF: 263.99498; Found: 263.99517.

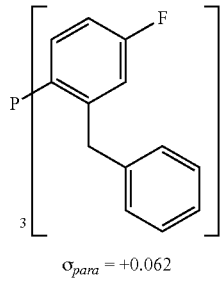

Tris(2-benzyl-4-fluorophenyl)phosphine L16

A flame dried, 25 mL recovery flask was equipped with a stir bar, sealed with a septum, and put under nitrogen. To a separate, flame-dried 40 mL vial was added 2-benzyl-1-bromo-4-fluorobenzene (0.5583 g, 2.106 mmol, 1.00 eq). The vial put under nitrogen, and THF (3.5 mL total) was used to transfer the aryl bromide to the reaction flask, with rinsing for quantitative transfer. The solution was cooled by submerging in a dry ice/acetone bath. To the −78° C. mixture was added nbutyllithium (1.6 Molar in hexanes, 1.18 mL, 1.895 mmol, 0.90 eq) dropwise over 5-10 minutes. The reaction was allowed to stir for 1.5 hours at −78° C. Phosphorus trichloride (45.9 µL, 72.3 mg, 0.527 mmol, 0.25 eq) was added neat in a dropwise manner over 2-3 minutes. The reaction was allowed to gradually warm to room temperature and stirred overnight.

The next day, the reaction was quenched with NH$_4$Cl (10 mL). Water (20 mL) and DCM (30 mL) were added, and the aqueous layer was extracted (3×30 mL DCM). The combined organics were washed with brine (100 mL), dried (Na$_2$SO$_4$), decanted, and concentrated. The crude product was purified by normal phase column chromatography (3 cm diameter, 120 mL SiO$_2$, isocratic 5/1 Hex/DCM), giving L16 as a white powder (0.1394 g, 0.2376 mmol, 45% yield).

$^1$H NMR (500 MHz, CDCl$_3$) δ 7.18-7.14 (m, 6H), 7.13-7.09 (m, 3H), 6.99 (d, J=7.0 Hz, 6H), 6.84-6.76 (m, 6H), 6.71 (ddd, J=8.4, 6.2, 3.5 Hz, 3H), 4.06 (s, 6H). $^{13}$C NMR (126 MHz, CDCl$_3$) δ 163.75 (d, J=249.6 Hz), 148.35 (dd, J=28.5, 7.3 Hz), 139.53 (d, J=1.5 Hz), 135.93 (d, J=7.9 Hz), 129.85 (dd, J=11.1, 3.3 Hz), 129.33, 128.48, 126.36, 117.35 (dd, J=21.3, 5.4 Hz), 113.88 (d, J=20.4 Hz), 40.23 (dd, J=22.6, 1.3 Hz). $^{31}$P NMR (202 MHz, CDCl$_3$, referenced to H$_3$PO$_4$ in D$_2$O) δ -39.71 (q, J=2.3 Hz). $^{19}$F NMR (470 MHz, CDCl$_3$, referenced to CFCl$_3$ in CDCl$_3$) δ -112.80 (q, J=10.2 Hz). Rf=0.20 on normal phase TLC in 5/1 Hex/DCM. HRMS (EI$^+$) Calculated for C$_{39}$H$_{30}$F$_3$P: 586.2037; Found: 586.2039.

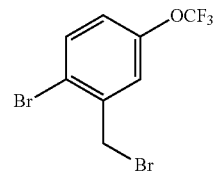 [SMILES: FC(F)(F)Oc1ccc(Br)c(CBr)c1]

1-bromo-2-(bromomethyl)-4-(trifluoromethoxy)benzene SI-7

A dry, stir bar-equipped, 3-neck 250 mL round bottom flask was fitted with a reflux condenser and put under nitrogen. 1-bromo-2-methyl-4-(trifluoromethoxy)benzene (2.550 g, 10.0 mmol, 1.00 eq), CCl$_4$ (20.0 mL, 0.50 Molar, not degassed), N-bromosuccinimide (recrystallized, 1.958 g, 11.0 mmol, 1.10 eq), and benzoyl peroxide (48.4 mg, 0.20 mmol, 2 mol %) were added by briefly removing a septum while under positive nitrogen pressure. After refluxing for 2.5 hours, monitoring of the reaction by NMR showed no conversion to product. Additional benzoyl peroxide (100 mg, 0.41 mmol, 4.1 mol %) was added, and the reaction was allowed to reflux for 24 hours.

The reaction was filtered through a silica gel plug (rinsing with 5:1 Hex/Et$_2$O), and concentrated in vacuo. The crude product was purified by normal phase column chromatography (5 cm diameter, 350 mL silica gel, isocratic 100% hexanes), giving SI-7 (1.548 g, 4.64 mmol, 46% yield).

$^1$H NMR (500 MHz, C$_6$D$_6$) δ 7.60 (d, J=8.8 Hz, 1H), 7.33 (d, J=2.7 Hz, 1H), 7.06 (ddq, J=8.8, 3.0, 1.0 Hz, 1H), 4.56 (s, 2H). $^{13}$C NMR (126 MHz, CDCl$_3$) δ 148.65 (q, J=1.9 Hz), 139.08, 134.69, 123.75, 122.61, 122.09, 120.39 (q, J=258.7 Hz), 32.29. $^{19}$F NMR (470 MHz, CDCl$_3$, referenced to CFCl$_3$ in CDCl$_3$) δ -58.51. HRMS (EI$^+$) Calculated for C$_8$H$_5$OF$_3$Br$_2$: 331.86596; Found: 331.86479.

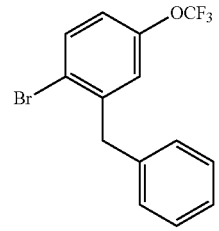 [SMILES: FC(F)(F)Oc1ccc(Br)c(Cc2ccccc2)c1]

2-benzyl-1-bromo-4-(trifluoromethoxy)benzene SI-8

This procedure was based on a previous report of the selective coupling of benzylic bromides. A stir bar-equipped, 3-neck 250 mL round bottom flask was sealed with two septa and equipped with a reflux condenser attached to a nitrogen inlet. After the system was put under nitrogen, reagents and solvents were added by briefly removing a septum while under a positive nitrogen pressure. In this manner, phenylboronic acid (0.4016 g, 3.294 mmol, 1.00 eq), ethanol (5.2 mL, 0.63 Molar), water (1.43 mL, 2.3

Molar), 1-bromo-2-(bromomethyl)-4-(trifluoromethoxy)benzene (1.10 g, 3.294 mmol, 1.00 eq) as a solution in toluene (6.3 mL, 0.52 Molar), aqueous sodium carbonate (3.7 mL, 1.00 Molar, 3.7 mmol, 1.13 eq), and Pd(PPh$_3$)$_4$ (0.1142 g, 0.0988 mmol, 3 mol %) were added to the reaction.

The reaction was heated to 80° C. for 15 hours and then filtered through celite, rinsing with Et$_2$O. After concentration, the crude material was diluted with H$_2$O and extracted with Et$_2$O. Combined organics were washed with brine, dried with Na$_2$SO$_4$, decanted, and reconcentrated. The crude product was purified by normal phase column chromatography (isocratic 100% hexanes), giving SI-8 as a clear colorless oil (0.3895 g, 1.176 mmol, 36% yield).

$^1$H NMR (500 MHz, CDCl$_3$) δ 7.52 (m, 1H), 7.32 (m, 2H), 7.25 (m, 1H), 7.19 (d, J=7.4 Hz, 2H), 6.85-6.79 (m, 2H), 4.08 (s, 2H). $^{13}$C NMR (126 MHz, CDCl$_3$) δ 162.11 (d, $J_{C-F}$=246.5 Hz), 142.75 (d, $J_{C-F}$=7.1 Hz), 138.73, 133.97 (d, $J_{C-F}$=7.9 Hz), 129.18, 128.78, 126.72, 118.93 (d, $J_{C-F}$=3.3 Hz), 118.01 (d, $J_{C-F}$=23.0 Hz), 115.16 (d, $J_{C-F}$=22.5 Hz), 41.94 (d, $J_{C-F}$=1.4 Hz). $^{19}$F NMR (470 MHz, CDCl$_3$, referenced to CFCl$_3$ in CDCl$_3$) δ −115.30. R$_f$=0.25 on reverse phase TLC in 3/1 MeCN/H$_2$O. HRMS (EI$^+$) Calculated for C$_{13}$H$_{10}$BrF: 263.99498; Found: 263.99517.

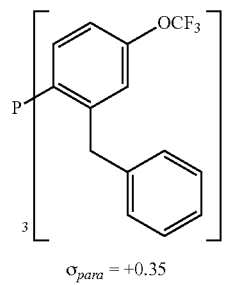

σ$_{para}$ = +0.35

Tris(2-benzyl-4-(trifluoromethoxy)phenyl)phosphine
L17

A flame dried, 25 mL recovery flask was equipped with a stir bar, sealed with a septum, and put under nitrogen. To a separate, flame-dried 40 mL vial was added 2-benzyl-1-bromo-4-(trifluoromethoxy)benzene (0.4368 g, 1.319 mmol, 1.00 eq). The vial put under nitrogen, and THF (2.2 mL total) was used to transfer the aryl bromide to the reaction flask, with rinsing for quantitative transfer. The solution was cooled by submerging in a dry ice/acetone bath. To the −78° C. mixture was added nbutyllithium (1.6 Molar in hexanes, 0.74 mL, 1.19 mmol, 0.90 eq) dropwise over 5-10 minutes. The reaction was allowed to stir for 1.5 hours at −78° C. Phosphorus trichloride (28.8 µL, 45.3 mg, 0.330 mmol, 0.25 eq) was added neat in a dropwise manner over 2-3 minutes. The reaction was allowed to gradually warm to room temperature and stirred overnight.

The next day, the reaction was quenched with NH$_4$Cl (5 mL). Water (10 mL) and DCM (15 mL) were added, and the aqueous layer was extracted (3×15 mL DCM). The combined organics were washed with brine (50 mL), dried (Na$_2$SO$_4$), decanted, and concentrated. The crude product was purified by normal phase column chromatography (isocratic 100% hexanes), giving L17 as a white powder (0.1394 g, 0.2376 mmol, 45% yield).

$^1$H NMR (500 MHz, CDCl$_3$) δ 7.13-7.04 (m, 9H), 6.97-6.88 (m, 12H), 6.68 (dd, J=8.4, 3.6 Hz, 3H), 4.06 (s, 9H). $^{13}$C NMR (126 MHz, CDCl$_3$) δ 150.29 (d, J=1.6 Hz), 147.87 (d, J=28.3 Hz), 139.05 (d, J=1.1 Hz), 135.82, 132.55 (d, J=12.1 Hz), 129.19, 128.45, 126.44, 122.59 (d, J=5.4 Hz), 120.53 (q, J=258 Hz), 118.65, 40.48 (d, J=21.8 Hz). $^{31}$P NMR (202 MHz, CDCl$_3$, referenced to H$_3$PO$_4$ in D$_2$O) δ −35.83. $^{19}$F NMR (470 MHz, CDCl$_3$, referenced to CFCl$_3$ in CDCl$_3$) δ −58.04. HRMS (ES$^+$) Calculated for C$_{42}$H$_{31}$O$_3$F$_9$P: 785.1867; Found: 785.1862.

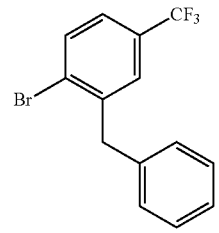 [SMILES: FC(F)(F)c1ccc(Br)c(Cc2ccccc2)c1]

2-benzyl-1-bromo-4-(trifluoromethyl)benzene SI-9

In an inert atmosphere glovebox, combined (2-bromo-5-(trifluoromethyl)phenyl)methanol (25.0 g, 98.0 mmol, 1.00 eq), FeCl$_3$ (3.24 g, 20.0 mmol, 0.20 eq), and dry benzene (100 mL) in a stir bar-equipped 200 mL high pressure round bottom flask. The reaction was sealed, brought into a fume hood, and stirred at 100° C. for two hours. Monitoring the reaction by TLC (10% EtOAc in hexanes) showed low conversion. Additional FeCl$_3$ (4.00 g, 24.7 mmol, 0.25 eq) was added, and the reaction was stirred at 100° C. for 15 more hours.

At this point, TLC indicated that the reaction had gone to full conversion. The mixture was then filtered through celite (rinsing with hexanes) and concentrated in vacuo. The crude product was purified by normal phase column chromatography (isocratic 100% hexanes), giving SI-9 as a white solid (24.32 g, 77.2 mmol, 79% yield).

$^1$H NMR (500 MHz, CDCl$_3$) δ 7.70 (d, J=8.3 Hz, 1H), 7.39 (s, 1H), 7.36-7.29 (m, 3H), 7.25 (m, 1H), 7.18 (d, J=7.3 Hz, 2H), 4.16 (s, 2H). $^{13}$C NMR (126 MHz, CDCl$_3$) δ 141.62, 138.44, 133.59, 130.14 (q, J=32.7 Hz), 129.05, 128.84, 127.78 (q, J=3.8 Hz), 126.82, 124.75 (q, J=3.8 Hz), 123.93 (q, J=272.6 Hz), 41.87. $^{19}$F NMR (470 MHz, CDCl$_3$, referenced to CFCl$_3$ in CDCl$_3$) δ −65.23. HRMS (EI$^+$) Calculated for C$_{42}$H$_{31}$O$_3$F$_9$P: 313.99179; Found: 313.99135.

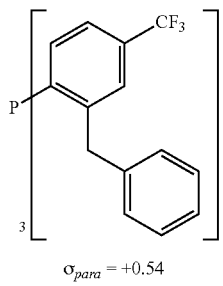

σ$_{para}$ = +0.54

Tris(2-benzyl-4-(trifluoromethyl)phenyl)phosphine
L18

To a suspension of magnesium powder (0.170 g, 7.00 mmol, 1.02 eq) in THF (14 mL) in a dry 40 mL vial was added 2-benzyl-1-bromo-4-(trifluoromethyl)benzene (2.16 g, 6.85 mmol, 1.00 eq; see *J. Am. Chem. Soc.* 2017, 139, 245-254). After addition of catalytic iodine and brief heating, the Grignard reaction initiated. The reaction was allowed to stir overnight at room temperature. The next day, a small aliquot was quenched with $H_2O$ and analyzed by TLC (100% hexanes), showing complete consumption of the aryl bromide. The reaction was submerged in a dry ice/acetone bath, and upon cooling to −78° C., phosphorus trichloride (0.198 mL, 0.3109 g, 2.20 mmol, 0.32 eq) was added dropwise. The reaction was stirred for one hour at −78° C. and then at room temperature overnight.

The next day, an orange solid was visible in the reaction. TLC of a quenched aliquot (5% EtOAc in hexanes) showed complete consumption of the dehalogenated intermediate. Saturated $NH_4Cl$ and $H_2O$ were added, and the crude mixture was extracted with EtOAc twice. The combined organic layers were dried with $Na_2SO_4$ and concentrated to afford a red oil. This material was filtered through a plug of silica gel, rinsing with 5% EtOAc in hexanes to remove the red baseline side products. After concentration to an oil and application of high vac to remove solvent residue, the crude product was recrystallized from hot methanol (7 mL). After cooling for 30 minutes in an ice bath, the mixture was filtered through a medium porosity glass frit to give L18 as a white solid (0.530 grams, 0.720 mmol, 33% yield).

$^1$H NMR (500 MHz, $CDCl_3$) δ 7.39 (dd, J=4.5, 1.9 Hz, 3H), 7.26 (dd, J=7.8, 1.1 Hz, 3H), 7.11-7.03 (m, 9H), 6.93-6.88 (m, 6H), 6.73 (dd, J=8.0, 3.7 Hz, 3H), 4.09 (s, 6H). $^{13}$C NMR (126 MHz, $CDCl_3$) δ 146.40 (d, J=27.5 Hz), 138.78 (d, J=0.8 Hz), 138.25 (d, J=13.6 Hz), 134.80, 131.65 (d, J=32.4 Hz), 129.11, 128.50, 127.05 (dq, J=3.7, 1.1 Hz), 126.56, 124.01 (q, J=272.9 Hz), 123.50 (q, J=3.7 Hz), 40.61 (d, J=21.1 Hz). $^{31}$P NMR (202 MHz, $CDCl_3$, referenced to $H_3PO_4$ in $D_2O$) δ −31.72. $^{19}$F NMR (470 MHz, $CDCl_3$, referenced to $CFCl_3$ in $CDCl_3$) δ −63.23. HRMS ($ES^+$) Calculated for $C_{42}H_{31}F_9P$: 737.2020; Found: 737.2012.

Ligand Testing Data

Determination of Retention Times.

Conditions: OD-H chiral column, 2.0 mL/min, isocratic 100% hexanes.

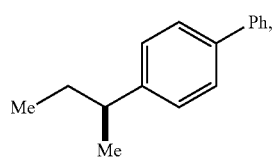

(+)-3a

Branched Product, Major enantiomer: 5.9 minutes

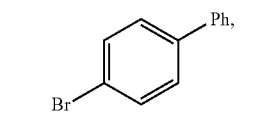

2a

Starting Aryl Bromide: 6.9 minutes

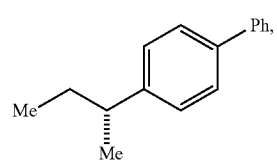

(−)-3a

Branched Product, Minor enantiomer: 9.9 minutes

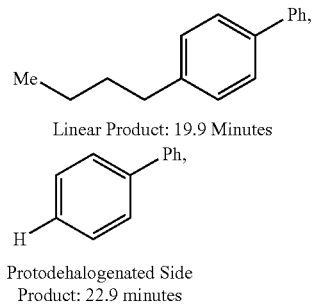

4a

Linear Product: 19.9 Minutes

Protodehalogenated Side Product: 22.9 minutes

Determination of Response Factors.

All standard solutions were prepared by dissolving the compounds in HPLC hexanes in 25 mL volumetric flasks.

| Compound | Amount (μmol) | Injection Volume (μL) | Absorbance Area (mAU at 214 nm) | μmol/mAU (Normalizing to 5 μL injection) |
|---|---|---|---|---|
| (±)-3a | 83.2 | 10 | 14338.73 | 0.01160 |
| (±)-3a | 79.9 | 5 | 6909.31 | 0.01156 |
| (±)-3a | 79.9 | 2.5 | 3463.31 | 0.01153 |
| Average | | | | 0.01156 |
| 2a | 78.9 | 5 | 7193.07 | 0.01097 |
| 2a | 78.9 | 2.5 | 3559.17 | 0.01108 |
| Average | | | | 0.01103 |
| Biphenyl | 90.1 | 5 | 5986 | 0.01505 |

General Procedure for Testing Ligands:

Cross-coupling reactions were assembled per the General Procedure described above, using boronic acid (S)-1a in ≥99:1 e.r. After 24 hours, the reactions were cooled to room temperature and filtered through a plug of silica gel in a glass pipet, rinsing with HPLC grade hexanes. The filtrate was collected in 25 mL volumetric flasks and further diluted with hexanes to the 25 mL mark. After thorough mixing, an aliquot of this solution was transferred to an HPLC vial and immediately subjected to HPLC analysis using the same conditions as above (OD-H chiral column, 2.0 mL/min, isocratic 100% hexanes, 214.4 nm absorbance). On each new day of HPLC analysis, a standard solution of the branched product standard was analyzed in duplicate to confirm the bulb brightness and to adjust response factors if necessary. If peak retention times drifted, standards were repeated as necessary to confirm the identity of the peaks.

Example 3. Synthesis and Characterization of Boron-Containing Compounds

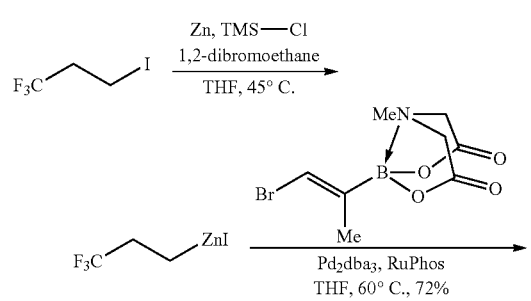

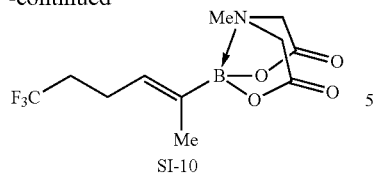

SI-10

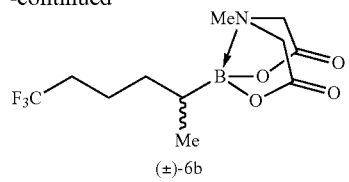

(±)-6b

SI-10.

To zinc dust (3.24 g, 49.5 mmol, 3.41 eq) in a nitrogen-purged 40 mL vial with stir bar were added trimethylsilyl chloride (100 μL, 120 mg, 1.1 mmol, 8 mol %) and 1,2-dibromoethane (100 μL, 220 mg, 1.2 mmol, 8 mol %) by syringe. Anhydrous THF (16 mL) was added, followed by 1-iodo-3,3,3-trifluoropropane (3.8 g, 17.0 mmol, 1.17 eq) portionwise at RT with stirring over 20 min, keeping the exotherm below 50° C. The suspension was then stirred for 1 h at 50° C. To a separate 100 mL round bottom flask purged with nitrogen containing a stir bar were added RuPhos (655 mg, 1.40 mmol, 10 mol %), Pd$_2$dba$_3$ (629 mg, 0.687 mmol, 5 mol %), and DMF (20 mL). This was stirred for 30 min at 23° C. Trans-2-bromo-1-methylvinyl MIDA boronate (Aldrich cat. no. 763853, 3.79 g, 14.5 mmol, 1.00 eq) was then added to this solution in 13 mL DMF. The alkyl zinc suspension was filtered through a syringe filter and the filtrate was added to the DMF solution. The remaining alkylzinc solution was washed over with additional THF (2 mL). The reaction was then stirred for 24 h at 50° C., after which time nearly complete conversion of the vinyl bromide was observed by TLC (Cis plate, 2:1 H$_2$O:MeCN, KMnO$_4$ stain). In a separatory funnel, the reaction was diluted with EtOAc and saturated aqueous NH$_4$Cl was added. The aqueous phase was extracted twice with EtOAc. The combined organic phase was washed three times with H$_2$O, each time adding a few mL of brine to break the emulsion. The organic phase was dried with Na$_2$SO$_4$, concentrated to a dark orange foam, then dissolved in DCM and adsorbed onto celite. The celite pad was loaded onto a Cis silica column of 100 mL volume, eluting with a gradient of 30% to 60% MeCN in H$_2$O. The product-containing fractions were combined and solid NaCl was added to induce phase separation. The organic phase was separated and the aqueous layer extracted with EtOAc (×2). The combined organic phases were dried and concentrated to give SI-10 as a yellow solid (2.91 g, 9.93 mmol 68% yield).

$^1$H NMR (500 MHz, CDCl$_3$) δ 5.87 (t, J=7.2 Hz, 1H), 3.81 (d, J=16.3 Hz, 2H), 3.69 (d, J=16.3 Hz, 2H), 2.79 (s, 3H), 2.41 (q, J=7.3 Hz, 2H), 2.27-2.14 (m, 2H), 1.68 (dt, J=1.6, 0.9 Hz, 3H). $^{13}$C NMR (126 MHz, CDCl$_3$) δ166.90, 136.96, 61.77, 46.25, 33.06 (q, J$_{C-F}$=27.7 Hz), 21.23 (q, J$_{C-F}$=2.5 Hz), 14.39. $^{19}$F NMR (470 MHz, CDCl$_3$) −66.33 (t, J=11.0 Hz). $^{11}$B NMR (128 MHz, CDCl$_3$) δ 11.02. HRMS (ES$^+$) Calculated for C$_{11}$H$_{16}$NO$_4$BF$_3$: 294.1124; Found: 294.1121.

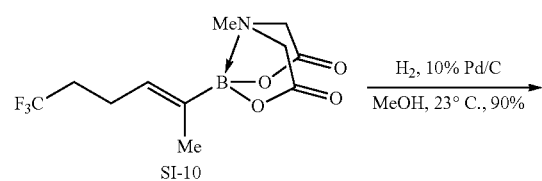

(±)-6b.

A 200 mL round bottom flask was charged with a stir bar, SI-10 (2.59 g, 8.84 mmol), and 10% Pd/C (1.3 g). The flask was sealed with a rubber septum and purged with nitrogen. Methanol (30 mL) was added via syringe. A balloon of hydrogen was affixed by needle and the headspace was purged with hydrogen. The balloon was refilled with hydrogen and affixed to the reaction again. The black suspension was stirred for two hours at 23° C. Monitoring the reaction by TLC (100% EtOAc, KMnO$_4$) showed complete conversion. The headspace was purged with nitrogen and the reaction was filtered through a silica plug twice, washing with EtOAc. The flow-through was concentrated to give 6b as a white solid (2.34 g, 7.93 mmol, 90% yield).

$^1$H NMR (500 MHz, acetone-d$_6$) δ 4.20 (dd, J=17.0, 4.5 Hz, 2H), 4.03 (dd, J=17.0, 4.1 Hz, 2H), 3.16 (s, 3H), 2.28-2.07 (m, 2H), 1.81-1.45 (m, 3H), 1.27 (ddt, J=12.1, 8.7, 4.9 Hz, 1H), 0.93 (m, 4H). $^{13}$C NMR (126 MHz, acetone-d$_6$) δ 168.51, 129.47, 127.27, 63.12, 62.94, 45.85, 33.89 (q, J$_{C-F}$=27.7 Hz), 31.81, 20.83 (q, J$_{C-F}$=2.5 Hz), 14.19. $^{19}$F NMR (470 MHz, acetone-d$_6$) δ −66.32 (t, J=11.1 Hz). $^{11}$B NMR (128 MHz, acetone-d$_6$) δ 13.81. HRMS (ES$^+$) Calculated for C$_{11}$H$_{18}$NO$_4$BF$_3$: 296.1281; Found: 296.1277.

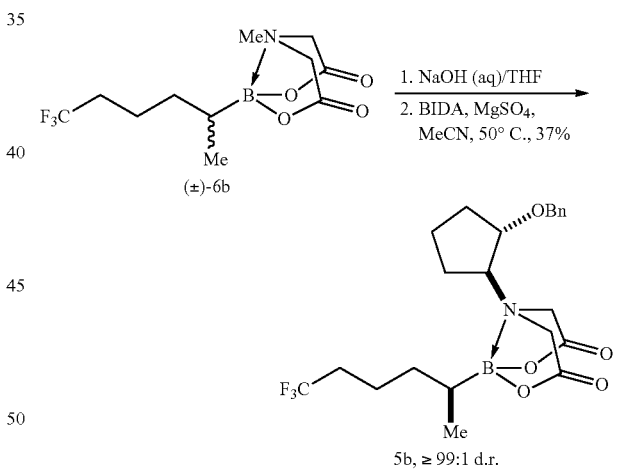

BIDA Boronate 5b.

To a 100-mL round-bottom flask with a stir bar was added MIDA boronate (±)-6b (2.07 g, 7.01 mmol), THF (35 mL, 0.20 Molar) and freshly prepared 1M NaOH (35 mL, 5.0 eq). The mixture was stirred at 23° C. until complete conversion was confirmed by TLC (100% EtOAc, KMnO$_4$). THF was removed under rotary evaporation (bath temperature 40° C.). When most of the THF was removed, the receiving flask was emptied and dried and rotary evaporation was then continued until water condensation began to collect in the receiving flask. Saturated NH$_4$Cl (35 mL) was added to the resulting aqueous solution and this was extracted with MTBE (4×35 mL) in a separatory funnel. The organic phase was dried over Na$_2$SO$_4$, filtered, and concentrated to an oil.

The oil was combined with BIDA (2.15 g, 7.04 mmol, 1.0 eq), MgSO$_4$ (2.0 g, 16.6 mmol, 2.4 eq), and anhydrous MeCN (14 mL, 0.50 Molar) in a 40 mL vial and stirred at 50° C. overnight. The reaction was filtered through fluorosil in a glass frit, rinsing with EtOAc. The filtrate was concentrate to a white foam. The two diastereomers were resolved by silica gel column (125 g silica, 1:1 Hex/EtOAc). The diastereomer with the higher R$_f$ was isolated as 5b (1.19 g, 2.61 mmol, 37%). The stereochemistry of the C2 center of 5b was assigned by analogy to the other BIDA boronates resolved by silica gel column.

$^1$H-NMR in CDCl$_3$ showed a diastereomeric ratio of ≥99:1 by integrating the methyl doublets of 5b and epi-5b at 0.87 and 0.98 ppm, respectively. The absolute stereochemistry at the boron-bearing carbon was tentatively assigned based on analogy to other BIDA boronates.

$^1$H NMR (500 MHz, acetone-d$_6$) δ 7.44-7.29 (m, 5H), 4.65 (d, J=10 Hz, 1H), 4.58 (d, J=10 Hz, 1H), 4.41 (q, J=6.5 Hz, 1H), 4.13 (d, J=17.6 Hz, 1H), 4.10, (s, 2H), 3.97 (d, J=17.6 Hz, 1H), 3.77 (td, J=8.7, 6.2 Hz, 1H), 2.34-2.08 (m, 4H), 1.89-1.76 (m, 3H), 1.76-1.47 (m, 4H), 1.28 (qd, J=9.1, 4.4 Hz, 1H), 1.11-0.90 (m, 1H), 0.87 (d, J=7.0 Hz, 3H). $^{13}$C NMR (126 MHz, acetone-d$_6$) δ169.62, 167.80, 138.60, 128.85, 128.49, 128.22, 80.77, 73.02, 71.98, 60.69, 56.73, 33.84 (q, J$_{C-F}$=27.7 Hz), 32.14, 26.96, 21.72, 20.63 (q, J$_{C-F}$=2.5 Hz), 14.63. $^{19}$F NMR (470 MHz, acetone-d$_6$) δ −66.27 (t, J=11.6 Hz). $^{11}$B NMR (128 MHz, acetone-d$_6$) δ 14.13. [α]$^{20}_D$=−6.4 (c 1.46, CHCl$_3$). HRMS (ES$^+$) Calculated for C$_{22}$H$_{30}$NO$_5$BF$_3$: 456.2169; Found: 456.2170.

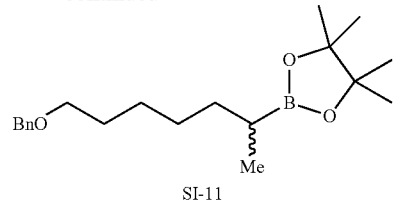

SI-11.

The pinacol boronic ester was synthesized according to a modified literature procedure (Hong et al., *J. Amer. Chem. Soc.* 2014, 136 (30), 10581). In an inert atmosphere glovebox, sodium tert-butoxide (9.652 g, 100.4 mmol, 3.15 eq) was added to a dry, stir bar-equipped 500 mL round bottom flask. In a separate dry 300 mL round bottom flask, a mixture was prepared containing Et(Bpin)$_2$ (12.23 g, 43.37 mmol, 1.36 eq) and 5-benzyloxypentyl bromide[12] (8.20 g, 31.9 mmol, 1.00 eq) (see Chowdhury et al., *Organic Letters* 2009, 11 (15), 3270). Both flasks were sealed with rubber septa, brought out into a fume hood, and connected to nitrogen lines. To the flask containing NaOt-Bu was added anhydrous THF (97 mL), and the suspension was cooled to 0° C. in an ice/water bath. Additional THF (25 mL) was added to the Et(Bpin)$_2$/alkyl bromide mixture, and the resulting solution was transferred (gradually over six minutes, using an additional 25 mL THF for quantitative trans-

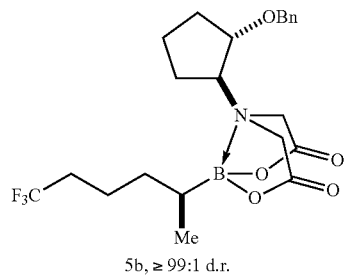 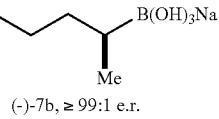

Sodium alkyltrihydroxyborate (−)-7b was made from BIDA boronate 5b according to general procedure B. The product was isolated by concentration in vacuo (0.268 g, 1.20 mmol, quantitative yield, white solid).

$^1$H NMR (500 MHz, CD3OD) 2.12 (dtd, J=14.6, 11.4, 5.1 Hz, 1H), 2.06-1.91 (m, 1H), 1.66 (ddt, J=16.0, 10.7, 5.2 Hz, 1H), 1.60-1.47 (m, 1H), 1.39 (ddq, J=17.2, 11.5, 5.7 Hz, 1H), 1.15-1.04 (m, 1H), 0.82 (d, J=7.1 Hz, 3H), 0.46 (s, 1H). $^{13}$C NMR (126 MHz, CD3OD) δ 35.26 (q, J$_{C-F}$=27.7 Hz), 34.20, 22.87 (q, J$_{C-F}$=2.5 Hz), 16.18. $^{11}$B NMR (128 MHz, CD3OD) δ 6.66. $^{19}$F NMR (470 MHz, CD3OD) δ −67.49 (t, J=11.0 Hz). [α]$^{20}_D$=−15.9 (c=1.53, CD3OD).

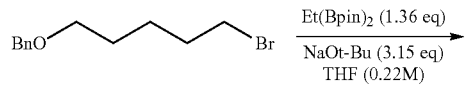

fer) into the flask containing NaOt-Bu. During this time, a precipitate began to form. The reaction was allowed to stir overnight, gradually warming to room temperature.

The next day, the reaction was diluted with Et$_2$O (250 mL) and filtered through a pad of celite to remove salts. The filtrate was concentrated thoroughly in vacuo, giving a viscous orange oil. This crude product was purified by column chromatography (1 Liter silica gel, 10 cm diameter, isocratic 30:10:2 Hex/DCM/Et$_2$O), affording SI-11 as a clear colorless oil (7.68 g, 23.1 mmol, 72% yield).

$^1$H NMR (500 MHz, CDCl$_3$) δ 7.36-7.31 (m, 4H), 7.27 (m, 1H), 4.49 (s, 2H), 3.46 (t, J=6.7 Hz, 2H), 1.65-1.58 (m, 2H), 1.45 (m, 1H), 1.39-1.25 (m, 5H), 1.23 (s, 12H), 1.03-0.96 (m, 1H), 0.95 (d, J=5.7 Hz, 3H). $^{13}$C NMR (126 MHz, CDCl$_3$) δ 138.88, 128.47, 127.75, 127.57, 82.91, 73.00, 70.72, 33.30, 29.91, 28.96, 26.54, 24.90, 24.87, 15.65. $^{11}$B NMR (128 Hz, CDCl$_3$) δ 34.37. R$_f$=0.25 on normal phase TLC in 30:10:2 Hex/DCM/Et$_2$O. HRMS (EI$^+$) Calculated for C$_{20}$H$_{33}$O$_3$B: 332.25229; Found: 332.25227.

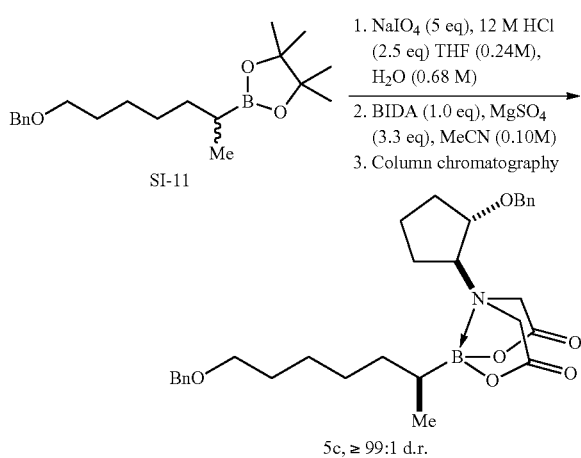

BIDA Boronate 5c.

The pinacol boronic ester SI-11 (6.68 g, 20.1 mmol, 1.00 eq) was added to a stir bar-equipped 1 Liter round bottom flask. THF (84 mL, 0.24 M), H$_2$O (30 mL, 0.68 M), and sodium periodate (21.5 g, 100.5 mmol, 5.00 eq) were added. To the resulting stirring mixture was added concentrated HCl (12 Molar, 4.2 mL, 50.4 mmol, 2.5 eq). The reaction was allowed to stir at room temperature for two hours. Monitoring the reaction by TLC showed the formation of boronic acid (with 1:1 Hex/EtOAc) and consumption of starting material (with 5/1 Hex/EtOAc).

Solvent was removed by rotary evaporation. The aqueous mixture was diluted with addition water and extracted with methyl tert-butyl ether three times. Combined organic layers were washed with water six times to remove any traces of the oxidant before finally drying with Na$_2$SO$_4$ and performing a solvent switch to dry acetonitrile (200 mL, 0.10 Molar). To this solution was added a stir bar, magnesium sulfate (8.04 g, 66.8 mmol, 3.3 eq), and BIDA (6.18 g, 20.2 mmol, 1.00 eq). The reaction was sealed with a rubber septum and vac-filled with nitrogen (using brief cycles to avoid solvent evaporation). The reaction was stirred overnight at 60° C.

The next day, the reaction was filtered through a pad of silica gel, rinsing with EtOAc. The crude product was resolved by normal phase column chromatography (1/1.3 Hex/EtOAc), giving a fraction of mostly the first diastereomer and another fraction of mostly the second diastereomer. The first diastereomer was repurified with two more columns (1/1.2 Hex/EtOAc and 1/1.1 Hex/EtOAc), giving the pure product as a sticky foam (3.29 g, 6.31 mmol, 31.4% yield). $^1$H-NMR in CDCl$_3$ showed a diastereomeric ratio of ≥99:1 by integrating the methyl signals of 5c and epi-5c at 0.86 and 0.98 ppm, respectively. The absolute stereochemistry at the boron-bearing carbon was tentatively assigned based on analogy to other BIDA boronates.

$^1$H NMR (500 MHz, CDCl$_3$) δ 7.43-7.25 (m, 10H), 4.65 (d, J=11.5 Hz, 1H), 4.49 (s, 2H), 4.38 (d, J=11.5 Hz, 1H), 4.00 (d, J=16.7 Hz, 1H), 3.90 (q, J=6.7 Hz, 1H), 3.62 (m, 1H), 3.61 (d, J=16.8 Hz, 1H), 3.46 (t, J=6.6 Hz, 2H), 3.43 (d, J=16.4 Hz, 1H), 3.32 (d, J=16.9 Hz, 1H), 2.21 (m, 1H), 2.06 (m, 1H), 1.88-1.68 (m, 3H), 1.65-1.57 (m, 3H), 1.53-1.43 (m, 2H), 1.40-1.19 (m, 6H), 0.86 (d, J=6.1 Hz, 3H), 0.83 (m, 1H). $^{13}$C NMR (126 MHz, CDCl$_3$) δ 168.93, 167.39, 138.84, 136.38, 128.97, 128.74, 128.45, 128.43, 127.74, 127.54, 79.12, 72.90, 72.05, 70.65, 61.03, 56.14, 32.23, 29.85, 29.58, 27.86, 26.57, 26.52, 21.41, 14.72. $^{11}$B NMR (128 MHz, CDCl$_3$) δ 13.67. R$_f$=0.30 on normal phase TLC in 1/1.5 Hex/EtOAc. [α]$^{20}_D$=+31.9 (c=1.0, acetone). HRMS (ES$^+$) Calculated for C$_{30}$H$_{41}$BNO$_6$: 522.3027; Found: 522.3028.

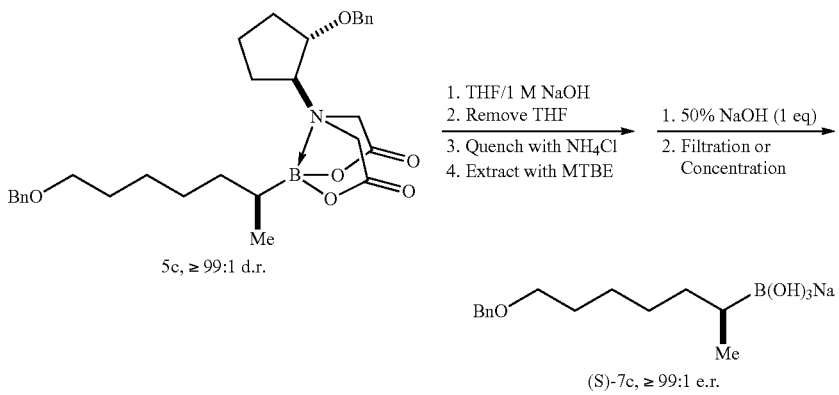

Sodium alkyltrihydroxyborate (S)-7c was made from BIDA boronate 5c according to general procedure B. The product was isolated by concentration in vacuo (1.64 g, 5.65 mmol, 90% yield).

$^1$H NMR (500 MHz, CD$_3$OD) δ 7.32 (d, J=4.3 Hz, 4H), 7.26 (ddd, J=8.8, 4.9, 3.8 Hz, 1H), 4.48 (s, 2H), 3.48 (t, J=6.7 Hz, 2H), 1.65-1.57 (m, 2H), 1.55-1.26 (m, 4H), 1.17 (m, 1H), 1.04 (m, 1H), 0.83 (d, J=7.1 Hz, 3H), 0.58 (br. s, 1H). $^{13}$C NMR (126 MHz, CD$_3$OD) δ 139.86, 129.33, 128.84, 128.59, 73.80, 71.74, 34.87, 31.02, 30.82, 27.97, 16.41. $^{11}$B NMR (128 MHz, CD$_3$OD) δ 6.83.

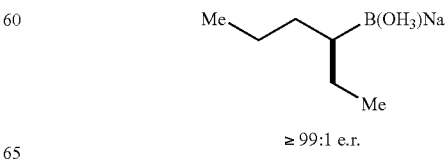

≥ 99:1 e.r.

(S)-7d.

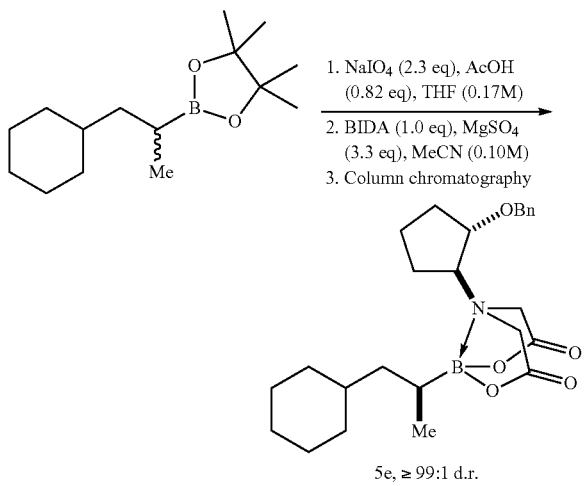

then filtered to give the BIDA boronate. After a second crop was recrystallized, the product was isolated as a white powder (8.66 g, 20.1 mmol, 12% yield). ¹H-NMR in DMSO-d6 showed a diastereomeric ratio of ≥99:1 by integrating the methyl signals of 5e and epi-5e at 0.72 and 0.80 ppm, respectively.

¹H NMR (500 MHz, DMSO-d$_6$, 40° C.) δ 7.40-7.26 (m, 5H), 4.53 (d, J=11.3 Hz, 1H), 4.46 (d, J=11.3 Hz, 1H), 4.18-4.09 (m, 3H), 4.06 (d, J=17.7 Hz, 1H), 3.93 (d, J=17.0 Hz, 1H), 3.56 (td, J=8.7, 6.1 Hz, 1H), 2.13-1.95 (m, 2H), 1.76-1.52 (m, 8H), 1.50-1.39 (m, 1H), 1.36-0.84 (m, 8H), 0.74 (d, J=6.7 Hz, 3H), 0.65 (q, J=12.5, 11.8 Hz, 1H). ¹³C NMR (126 MHz, CDCl$_3$) δ 169.24, 167.66, 136.67, 128.85, 128.52, 128.32, 79.50, 72.21, 72.07, 60.85, 56.29, 39.55, 34.94, 34.52, 31.97, 29.76, 26.91, 26.68, 26.66, 26.42, 21.52, 14.59. ¹¹B NMR (128 MHz, CDCl$_3$) δ 14.48. $[\alpha]^{20}_D$=+2.25 (c 1.0, acetone). HRMS (ES+) Calculated for $C_{25}H_{37}BNO_5$: 442.2765; Found: 442.2760.

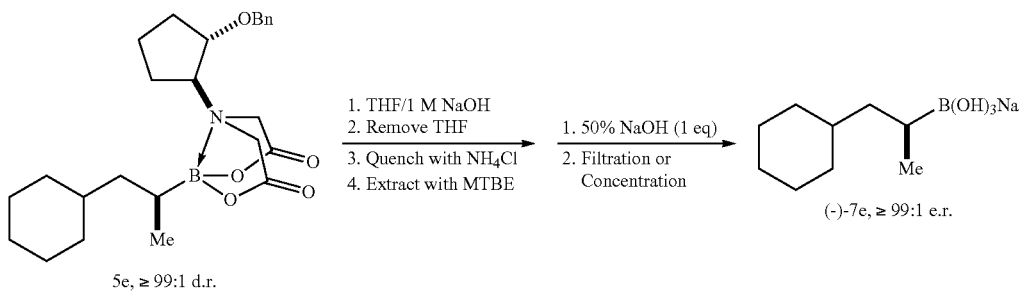

BIDA Boronate 5e.

AcOH (11.7 mL, 12.3 g, 204 mmol, 0.82 eq.) was added as a single portion to a slurry of NaIO$_4$ (125 g, 584 mmol, 2.3 eq.) and pinacol boronic ester 2-(1-cyclohexylpropan-2-yl)-4,4,5,5-tetramethyl-1,3,2-dioxaborolane (62.8 g, 249 mmol, 1.00 eq.) in THF (1.5 L, 0.17 Molar). The reaction mixture was stirred at room temperature, filtered to remove salts and the filter cake washed with Et$_2$O (200 mL). The filtrate was concentrated in vacuo and then partitioned between H$_2$O (500 mL) and methyl tert-butyl ether (1 L). The organic layer was separated, and then the aqueous phase was extracted with a MTBE (1 L). The combined organics were washed with water (5×300 mL) until free of peroxide (as determined by peroxide test strips). The organics were diluted with DMSO (196 mL, 1.3 Molar) and concentrated in vacuo to afford a DMSO solution of boronic acid. The DMSO solution was diluted with toluene (2.1 L, 0.12 Molar) and BIDA (50 g, 163 mmol, 0.65 eq.) was added. The reaction mixture was then heated at reflux with a Dean-Stark Trap for 3 hours. The reaction mixture was concentrated in vacuo to afford 90 g of crude material which was purified with the following gradient elution of hexanes/EtOAc (80:20 3 L, 70:30 2 L, 60:40 1 L, 55:45 1 L, 50:50 1 L, 45:55 1 L, 30:70 1 L), affording the mostly resolved BIDA boronate (12.5 g, 28.3 mmol 17% yield, ~97:3 dr) after 5 columns. This material was then suspended in boiling hexanes (3 L), and a minimal amount of EtOAc (~90 mL) was added to effect dissolution. The mixture was cooled to room temperature, cooled in an ice bath for one hour, and Sodium alkyltrihydroxyborate (−)-7e was made from BIDA boronate 5e according to general procedure B. The product was isolated by concentration in vacuo (1.64 g, 5.65 mmol, 90% yield, white solid).

¹H NMR (400 MHz, D$_2$O) δ 1.71 (d, J=13.4 Hz, 1H), 1.65-1.45 (m, 3H), 1.29-0.99 (m, 4H), 0.92-0.75 (m, 2H), 0.64 (d, J=7.2 Hz, 3H), 0.48-0.27 (m, 1H). ¹³C NMR (101 MHz, D$_2$O) δ 42.20, 36.28, 36.01, 32.93, 27.58, 27.26, 27.06, 16.22. ¹¹B NMR (128 MHz, D$_2$O) δ 8.71. $[\alpha]^{20}_D$=−16.9 (c 0.7, H$_2$O).

Example 4. Synthesis and Characterization of Cross-Coupled Products

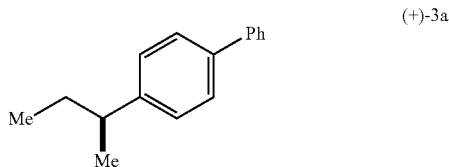 [SMILES: CC[C@H](C)c1ccc(-c2ccccc2)cc1]

Boronic acid (S)-1a (≥99:1 e.r.) was prepared in 77% yield by general procedure C and coupled to organohalide 2a to give product (+)-3a by general procedure D. The branched/linear product ratio of the crude reaction was determined to be 268/1 by HPLC (OD-H chiral column, isocratic 100% hexanes, 2.0 mL/min, 214.4 nm absorbance).

Branched=6.0 and 10.3 minutes; linear=19.9 minutes. The product was isolated in 81% yield (17.0 mg) by purification with reverse phase flash chromatography (6/1 MeCN/H$_2$O). The e.r. of the purified product was determined to be 98.02:1.98. (98% es) using chiral HPLC (OD-H chiral column, isocratic 100% hexanes, 2.0 mL/min, 254.4 nm absorbance). Major=6.0 minutes; minor=10.3 minutes.

A duplicate run of the reaction gave a branched/linear product ratio of 301/1, isolated yield of 83%, and enantiospecificity of 98%.

$^1$H NMR (500 MHz, CDCl$_3$) δ 7.60 (d, J=7.3 Hz, 2H), 7.53 (d, J=8.2 Hz, 2H), 7.43 (t, J=7.6 Hz, 2H), 7.33 (t, J=7.3 Hz, 1H), 7.26 (d, J=8.1 Hz, 2H), 2.65 (h, J=7.0 Hz, 2H), 1.64 (m, 2H), 1.28 (d, J=6.9 Hz, 3H), 0.87 (t, J=7.4 Hz, 3H). $^{13}$C NMR (126 MHz, CDCl$_3$) δ 146.95, 141.30, 138.81, 128.81, 127.60, 127.12, 127.11, 127.06, 41.48, 31.32, 21.98, 12.46. [α]$^{20}_D$=+23.2 (c 1.0, CHCl$_3$). HRMS (EI$^+$) Calculated for C$_{16}$H$_{18}$: 210.14085; Found: 210.14096.

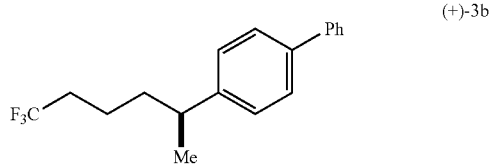 [SMILES: C[C@@H](CCCC(F)(F)F)c1ccc(-c2ccccc2)cc1]

(+)-3b

Boronic acid (S)-1b (≥99:1 e.r.) was prepared in 66% yield by general procedure C and coupled to organohalide 2a to give product (+)-3b by general procedure D. The branched/linear product ratio of the crude reaction was determined to be 243/1 by HPLC (Eclipse XDB-C8 column, isocratic 68/32 MeCN/H$_2$O, 1.2 mL/min, 254.4 nm absorbance). Branched=11.2 minutes; linear=12.0 minutes. The product was isolated in 59% yield (17.2 mg) by purification with reverse phase flash chromatography (5/1 MeCN/H$_2$O). The e.r. of the purified product was determined to be 99.12:0.88. (≥99% es) using chiral HPLC (AD-RH chiral column, isocratic 75/25 MeCN/H$_2$O, 0.5 mL/min, 254.4 nm absorbance). Major=8.9 minutes; minor=14.6 minutes.

A duplicate run of the reaction gave a branched/linear product ratio of 283/1, isolated yield of 61%, and enantiospecificity of ≥99%.

$^1$H NMR (500 MHz, CDCl$_3$) δ 7.59 (dd, J=8.2, 1.4 Hz, 2H), 7.54 (d, J=8.1 Hz, 2H), 7.43 (t, J=7.7 Hz, 2H), 7.33 (t, J=7.5 Hz, 1H), 7.25 (d, J=8.3 Hz, 2H), 2.75 (h, J=7.1 Hz, 1H), 2.06 (dddd, J=19.0, 17.3, 9.3, 5.4 Hz, 2H), 1.67 (ddd, J=9.7, 7.4, 3.6 Hz, 2H), 1.61-1.39 (m, 4H), 1.30 (d, J=7.0 Hz, 3H). $^{13}$C NMR (126 MHz, CDCl$_3$) δ 145.98, 141.15, 139.24, 128.86, 127.43, 127.35, 127.30 (q, J=277 Hz), 127.14, 39.54, 37.47, 33.92 (q, J=29 Hz), 22.34, 20.32 (q, J=2.9 Hz). $^{19}$F NMR (470 MHz, CDCl$_3$) δ −66.88 (t, J=11.0 Hz). Rf=0.29 on reverse phase TLC in 5/1 MeCN/H$_2$O. [α]$^{20}_D$=+15.0 (c 1.0, CHCl$_3$). HRMS (EI$^+$) Calculated for C$_{18}$H$_{19}$F$_3$: 292.14389; Found: 292.14326.

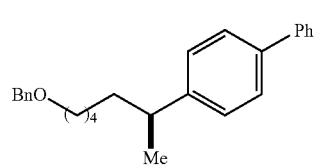

(+)-3c

Boronic acid (S)-1c (≥99:1 e.r.) was prepared in 71% yield by general procedure C and coupled to organohalide 2a to give product (+)-3c by general procedure D. The branched/linear product ratio of the crude reaction was determined to be 702/1 by HPLC (Eclipse XDB-C8 column, isocratic 70/30 MeCN/H$_2$O, 1.2 mL/min, 254.4 nm absorbance). Branched=24.8 minutes; linear=26.8 minutes. The product was isolated in 69% yield (24.7 mg) by purification with normal phase flash chromatography (20/1 Hex/Et$_2$O). The e.r. of the purified product was determined to be 99.05:0.95 (>99% es) using chiral HPLC (AD-RH chiral column, isocratic 94/6 MeCN/H$_2$O, 0.5 mL/min, 254.4 nm absorbance). Major=10.8 minutes; minor=19.0 minutes.

A duplicate run of the reaction gave a branched/linear product ratio of 550/1, isolated yield of 72%, and enantiospecificity of >99%.

$^1$H NMR (500 MHz, CDCl$_3$) δ 7.61 (d, J=7.7 Hz, 2H), 7.54 (d, J=8.1 Hz, 2H), 7.45 (t, J=7.7 Hz, 2H), 7.38-7.27 (m, 8H), 4.51 (s, 2H), 3.46 (t, J=6.6 Hz, 2H), 2.74 (h, J=7.0 Hz, 1H), 1.69-1.58 (m, 4H), 1.43-1.19 (m, 4H), 1.28 (d, J=6.9 Hz, 3H). $^{13}$C NMR (126 MHz, CDCl$_3$) δ 147.12, 141.30, 138.84, 138.83, 128.81, 128.47, 127.73, 127.59, 127.52, 127.15, 127.13, 127.07, 72.98, 70.56, 39.69, 38.48, 29.82, 27.69, 26.42, 22.47. Rf=0.27 on normal phase TLC in 20/1 Hex/Et$_2$O. [α]$^{20}_D$=+30.8 (c 1.0, CHCl$_3$). HRMS (EI$^+$) Calculated for C$_{26}$H$_{30}$O: 358.2297; Found: 358.2299.

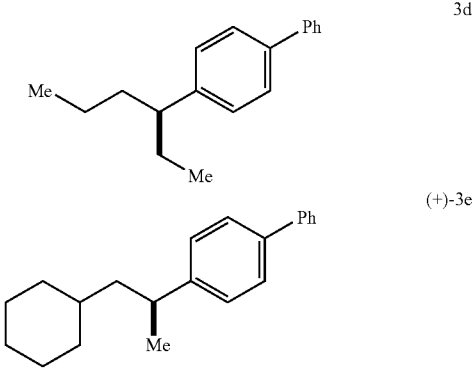

3d (+)-3e

Boronic acid (S)-1e (≥99:1 e.r.) was prepared in 67% yield by general procedure C and coupled to organohalide 2a to give product (+)-3e by general procedure D. The branched/linear product ratio of the crude reaction was determined to be 276/1 by HPLC (Eclipse XDB-C8 column, isocratic 85/15 MeCN/H$_2$O, 1.2 mL/min, 254 nm absorbance). Branched=9.3 minutes; linear=10.2 minutes. The product was isolated in 74% yield (20.3 mg) by purification with reverse phase flash chromatography (20/1 MeCN/H$_2$O). The e.r. of the purified product was determined to be 98.89:1.11 (>99% es) using chiral HPLC (OD-H chiral column, isocratic 100% hexanes, 2.0 mL/min, 254 nm absorbance). Major=6.2 minutes; minor=10.2 minutes.

A duplicate run of the reaction gave a branched/linear product ratio of 279/1, isolated yield of 72%, and enantiospecificity of >99%.

$^1$H NMR (500 MHz, CDCl$_3$) δ 7.63-7.56 (m, 2H), 7.52 (d, J=8.1 Hz, 2H), 7.42 (t, J=7.7 Hz, 2H), 7.32 (t, J=7.4 Hz, 1H), 7.28-7.23 (m, 2H), 2.87 (h, J=7.0 Hz, 1H), 1.78 (d, J=12.9 Hz, 1H), 1.72-1.58 (m, 4H), 1.58-1.49 (m, 2H), 1.42 (td, J=13.8, 7.2 Hz, 1H), 1.24 (d, J=6.9 Hz, 3H), 1.22-1.09 (m, 4H), 0.89 (q, J=11.1 Hz, 2H). $^{13}$C NMR (126 MHz, CDCl$_3$) δ 147.50, 141.31, 138.73, 128.82, 127.51, 127.16, 127.12, 127.06, 46.51, 36.44, 35.22, 33.79, 33.55, 26.86, 26.42, 22.90. $R_f$=0.26 on reverse phase TLC in 20/1 MeCN/H$_2$O. $[\alpha]^{20}_D$=+37.6 (c 1.0, CHCl$_3$). HRMS (EI$^+$) Calculated for C$_{21}$H$_{26}$: 278.20345; Found: 278.20395.

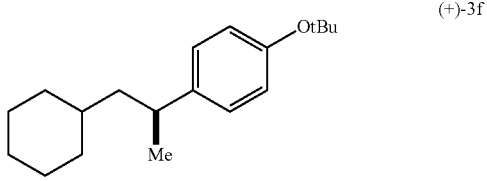 [SMILES: C[C@@H](CC1CCCCC1)c1ccc(OC(C)(C)C)cc1]

(+)-3f

Boronic acid (S)-1e (≥99:1 e.r.) was prepared in 67% yield by general procedure C and coupled to organohalide 2b to give product (+)-3f by general procedure D. The branched/linear product ratio of the crude reaction was determined to be 187/1 by HPLC (Eclipse XDB-C8 column, isocratic 85/15 MeCN/H$_2$O, 1.2 mL/min, 215.4 nm absorbance). Branched=9.4 minutes; linear=10.2 minutes. The product was isolated in 76% yield (20.4 mg) by purification with reverse phase flash chromatography (15/1 MeCN/H$_2$O). The e.r. of the purified product was determined to be 99.32:0.68 (>99% es) using chiral HPLC (OD-H chiral column, isocratic 100% hexanes, 2.0 mL/min, 214.4 nm absorbance). Major=3.07 minutes; minor=3.82 minutes.

A duplicate run of the reaction gave a branched/linear product ratio of 160/1, isolated yield of 70%, and enantiospecificity of >99%.

$^1$H NMR (500 MHz, CDCl$_3$) δ 7.04 (d, J=8.4 Hz, 2H), 6.89 (d, J=8.4 Hz, 2H), 2.77 (h, J=7.3 Hz, 1H), 1.73 (d, J=13.0 Hz, 1H), 1.70-1.55 (m, 4H), 1.44 (ddd, J=14.3, 8.2, 6.6 Hz, 1H), 1.39-1.34 (m, 1H), 1.33 (s, 9H), 1.18 (d, J=6.9 Hz, 3H), 1.16-1.08 (m, 4H), 0.90-0.80 (m, 2H). $^{13}$C NMR (126 MHz, CDCl$_3$) δ 153.18, 143.17, 127.25, 124.09, 78.11, 46.68, 36.11, 35.26, 33.69, 33.62, 29.02, 26.87, 26.46, 22.84. $R_f$=0.26 on reverse phase TLC in 15/1 MeCN/H$_2$O. $[\alpha]^{20}_D$=+19.3 (c 1.9, CHCl$_3$). HRMS (EI$^+$) Calculated for C$_{19}$H$_{30}$O: 274.22967; Found: 274.22963.

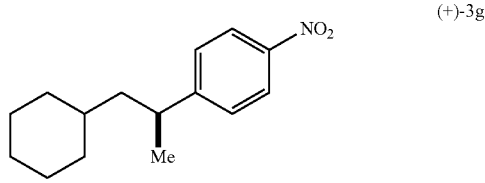 [SMILES: C[C@@H](CC1CCCCC1)c1ccc([N+](=O)[O-])cc1]

(+)-3g

Boronic acid (S)-1e (≥99:1 e.r.) was prepared in 66% yield by general procedure C and coupled to organohalide 2c to give product (+)-3g by general procedure D. The branched/linear product ratio of the crude reaction was determined to be 108/1 by HPLC (Eclipse XDB-C8 column, isocratic 70/30 MeCN/H$_2$O, 1.2 mL/min, 215.4 nm absorbance). Branched=12.7 minutes; linear=14.2 minutes. The product was isolated in 59% yield (14.3 mg) by purification with reverse phase flash chromatography (8/1 MeCN/H$_2$O) followed by normal phase flash chromatography (4/1 Hex/DCM). The e.r. of the purified product was determined to be 98.65:1.35 (>99% es) using chiral HPLC (AD-RH chiral column, isocratic 75/25 MeCN/H$_2$O, 0.5 mL/min, 214 nm absorbance). Major=22.1 minutes; minor=27.1 minutes.

A duplicate run of the reaction gave a branched/linear product ratio of 106/1, isolated yield of 62%, and enantiospecificity of >99% es.

$^1$H NMR (500 MHz, CDCl$_3$) δ 8.15 (d, J=8.7 Hz, 2H), 7.33 (d, J=8.7 Hz, 2H), 2.95 (h, J=8.2 Hz, 1H), 1.73 (d, J=13.1 Hz, 1H), 1.70-1.58 (m, 4H), 1.51 (ddd, J=14.4 Hz, 8.5 Hz, 6.2 Hz, 1H) 1.43 (dt, J=13.9 Hz, 7.1 Hz, 1H), 1.23 Hz (d, J=6.9 Hz, 2H), 1.18-1.03 (m, 4H), 0.93-0.82 (m, 2H). $^{13}$C NMR (126 MHz, CDCl$_3$) δ 156.19, 146.40, 127.91, 123.85, 46.07, 37.04, 35.23, 33.75, 33.33, 26.69, 26.31, 22.63. $R_f$=0.30 on reverse phase TLC in 8/1 MeCN/H$_2$O. $R_f$=0.27 on normal phase TLC in 4.1 Hex/DCM. $[\alpha]^{20}_D$=+56.5 (c 1.0, CDCl$_3$). HRMS (EI$^+$) Calculated for C$_{15}$H$_{22}$NO$_2$: 248.1651; Found: 248.1660.

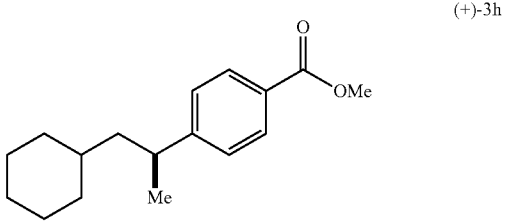 [SMILES: COC(=O)c1ccc([C@@H](C)CC2CCCCC2)cc1]

(+)-3h

Boronic acid (S)-1e (≥99:1 e.r.) was prepared in 67% yield by general procedure C and coupled to organohalide 2d to give product (+)-3h by general procedure D. The branched/linear product ratio of the crude reaction was determined to be 220/1 by HPLC (Eclipse XDB-C8 column, isocratic 70/30 MeCN/H$_2$O, 1.2 mL/min, 254.4 nm absorbance). Branched=13.7 minutes; linear=15.5 minutes. The product was isolated in 84% yield (21.7 mg) by purification with reverse phase flash chromatography (10/1 MeCN/H$_2$O). The e.r. of the purified product was determined to be 99.53:0.47 (>99% es) using chiral HPLC (OD-H chiral column, isocratic 100% hexanes, 2.0 mL/min, 214.4 nm absorbance). Major=6.4 minutes; minor=8.3 minutes.

A duplicate run of the reaction gave a branched/linear product ratio of 207/1, isolated yield of 88%, and enantiospecificity of >99%.

$^1$H NMR (500 MHz, CDCl$_3$) δ 7.96 (d, J=8.3 Hz, 2H), 7.24 (d, J=8.3 Hz, 2H), 3.90 (s, 3H), 2.88 (h, J=8.6 Hz, 1H), 1.74 (d, J=11.3 Hz, 1H), 1.68-1.54 (m, 4H), 1.50 (ddd, J=14.3, 8.6, 6.1 Hz, 1H), 1.40 (dt, J=13.9, 7.1 Hz, 1H), 1.21 (d, J=6.9 Hz, 3H), 1.17-1.04 (m, 4H), 0.91-0.80 (m, 2H). $^{13}$C NMR (126 MHz, CDCl$_3$) δ 167.34, 153.85, 129.86, 127.89, 127.17, 52.06, 46.19, 36.98, 35.22, 33.81, 33.38, 26.77, 26.37, 22.73. $R_f$=0.27 on reverse phase TLC in 10/1 MeCN/H$_2$O. $[\alpha]^{20}_D$=+39.1 (c 1.7, CDCl$_3$). HRMS (AP$^+$) Calculated for C$_{17}$H$_{25}$O$_2$: 261.1855; Found: 261.1851.

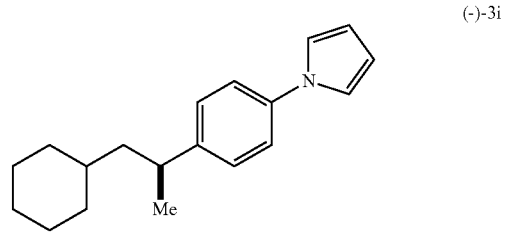 [SMILES: C[C@@H](CC1CCCCC1)c1ccc(-n2cccc2)cc1]

(-)-3i

Boronic acid (S)-1e (≥99:1 e.r.) was prepared in 65% yield by general procedure C and coupled to organohalide 2e to give product (-)-3i by general procedure D. The branched/linear product ratio of the crude reaction was determined to be 266/1 by HPLC (Eclipse XDB-C8 column, isocratic 75/25 MeCN/H$_2$O, 1.2 mL/min, 250 nm absorbance). Branched=14.6 minutes; linear=16.4 minutes. The product was isolated in 68% yield (18.3 mg) by purification with reverse phase flash chromatography (9/1 MeCN/H$_2$O) as an off-white solid. The e.r. of the purified product was determined to be 99.70:0.30 (>99% es) using chiral HPLC (AD-RH chiral column, isocratic 85/15 MeCN/H$_2$O, 0.5 mL/min, 214 nm absorbance). Major=14.7 minutes; minor=24.7 minutes.

A duplicate run of the reaction gave a branched/linear product ratio of 246/1, isolated yield of 62%, and enantiospecificity of >99%.

$^1$H NMR (500 MHz, CDCl$_3$) δ 7.31 (d, J=8.4 Hz, 2H), 7.22 (d, J=8.5 Hz, 2H), 7.07 (t, J=2.1 Hz, 2H), 6.33 (t, J=2.1 Hz, 2H), 2.85 (h, J=7.9 Hz, 1H), 1.77 (d, J=13.1 Hz, 1H), 1.70-1.59 (m, 4H), 1.50 (m, 1H), 1.41 (dt, J=13.9, 7.1 Hz, 1H), 1.22 (d, J=6.8 Hz, 3H), 1.19-1.10 (m, 4H), 0.93-0.83 (m, 2H). $^{13}$C NMR (126 MHz, CDCl$_3$) δ 145.84, 138.79, 128.07, 120.73, 119.52, 110.14, 46.48, 36.28, 35.22, 33.80, 33.46, 26.82, 26.41, 26.41, 22.96. R$_f$=0.26 on reverse phase TLC in 9/1 MeCN/H$_2$O. [α]$^{20}_D$=−112.8 (c 1.0, CHCl$_3$). HRMS (EI$^+$) Calculated for C$_{19}$H$_{25}$N: 267.19870; Found: 267.19823.

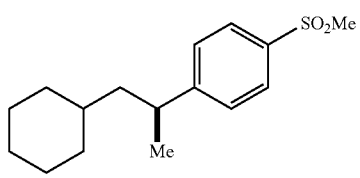

(−)-3j

Boronic acid (S)-1e (≥99:1 e.r.) was prepared in 65% yield by general procedure C and coupled to organohalide 2f to give product (−)-3j by general procedure D. The branched/linear product ratio of the crude reaction was determined to be 118/1 by HPLC (Eclipse XDB-C8 column, isocratic 68/32 MeCN/H$_2$O, 1.2 mL/min, 230 nm absorbance). Branched=6.3 minutes; linear=7.0 minutes. The product was isolated in 78% yield (21.8 mg) by purification with reverse phase flash chromatography (4/1 MeCN/H$_2$O) as a clear oil. The e.r. of the purified product was determined to be 99.74:0.26 (>99% es) using chiral HPLC (AD-RH chiral column, isocratic 75/25 MeCN/H$_2$O, 0.5 mL/min, 214 nm absorbance). Major=11.9 minutes; minor=17.2 minutes.

A duplicate run of the reaction gave a branched/linear product ratio of 119/1, isolated yield of 82%, and enantiospecificity of >99%.

$^1$H NMR (500 MHz, CDCl$_3$) δ 7.85 (d, J=8.3 Hz, 2H), 7.37 (d, J=8.3 Hz, 2H), 3.06 (s, 3H), 2.93 (h, J=8.0 Hz, 1H), 1.73 (d, 12.8 Hz, 1H), 1.69-1.58 (m, 4H), 1.51 (ddd, J=14.3, 8.5, 6.2 Hz, 1H), 1.43 (dt, J=13.9, 7.1 Hz, 1H), 1.22 (d, J=6.9 Hz, 3H), 1.19-1.04 (m, 4H), 0.92-0.82 (m, 2H). $^{13}$C NMR (126 MHz, CDCl$_3$) δ 154.92, 138.02, 128.09, 127.62, 46.08, 44.70, 36.99, 35.13, 33.72, 33.31, 26.69, 26.30, 26.28, 22.65. R$_f$=0.33 on reverse phase TLC in 4/1 MeCN/H$_2$O. [α]$^{20}_D$=−79.6 (c 1.0, CHCl$_3$). HRMS (EI$^+$) Calculated for C$_{16}$H$_{24}$O$_2$S: 280.14970; Found: 280.14856.

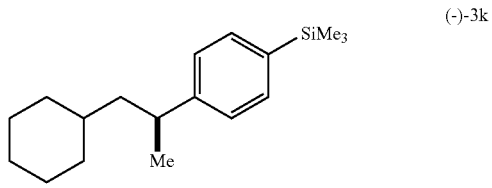

(−)-3k

Boronic acid (S)-1e (≥99:1 e.r.) was prepared in 65% yield by general procedure C and coupled to organohalide 2g to give product (−)-3k by general procedure D. The branched/linear product ratio of the crude reaction was determined to be 596/1 by HPLC (Eclipse XDB-C8 column, isocratic 85/15 MeCN/H$_2$O, 1.2 mL/min, 214.4 nm absorbance). Branched=14.6 minutes; linear=16.5 minutes. The product was isolated in 67% yield (19.8 mg) by purification with reverse phase flash chromatography (20/1 MeCN/H$_2$O) as clear oil. The e.r. of the purified product was determined to be 99.67:0.33 (>99% es) using chiral HPLC (AD-RH chiral column, isocratic 80/20 MeCN/H$_2$O, 0.5 mL/min, 214.4 nm absorbance). Major=19.3 minutes; minor=21.6 minutes.

A duplicate run of the reaction gave a branched/linear product ratio of 624/1, isolated yield of 78%, and enantiospecificity of >99%.

$^1$H NMR (500 MHz, CDCl$_3$) δ 7.44 (d, J=7.9 Hz, 2H), 7.17 (d, J=7.9 Hz, 2H), 2.81 (h, J=7.1 Hz, 1H), 1.75 (d, J=13.0 Hz, 1H), 1.69-1.58 (m, 4H), 1.50 (ddd, J=14.1, 7.9, 6.5 Hz, 1H), 1.38 (dt, J=13.8, 7.2 Hz, 1H), 1.20 (d, J=6.9 Hz, 3H), 1.19-1.06 (m, 4H), 0.91-0.81 (m, 2H), 0.26 (s, 9H). $^{13}$C NMR (126 MHz, CDCl$_3$) δ 149.03, 137.30, 133.53, 126.58, 46.45, 36.64, 35.14, 33.68, 33.63, 26.87, 26.40, 22.66, −0.85. R$_f$=0.21 on reverse phase TLC in 20/1 MeCN/H$_2$O. [α]$^{20}_D$=−110.0 (c 1.0, CDCl$_3$). HRMS (EI$^+$) Calculated for C$_{18}$H$_{30}$Si: 274.21168; Found: 274.21214.

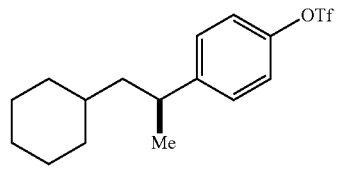

(−)-3l

Boronic acid (S)-1e (≥99:1 e.r.) was prepared in 65% yield by general procedure C and coupled to organohalide 2h to give product (−)-3l by general procedure D. The branched/linear product ratio of the crude reaction was determined to be 74/1 by HPLC (Eclipse XDB-C8 column, isocratic 80/20 MeCN/H$_2$O, 1.2 mL/min, 220.4 nm absorbance). Branched=9.8 minutes; linear=10.9 minutes. The product was isolated in 81% yield (29.5 mg) by purification with reverse phase flash chromatography (8/1 MeCN/H$_2$O) as clear oil. The e.r. of the purified product was determined to be 99.41:0.59 (>99% es) using chiral HPLC (AD-RH chiral column, isocratic 75/25 MeCN/H$_2$O, 0.5 mL/min, 214.4 nm absorbance). Major=9.1 minutes; minor=10.6 minutes.

A duplicate run of the reaction gave a branched/linear product ratio of 76/1, isolated yield of 76%, and enantiospecificity of >99%.

$^1$H NMR (500 MHz, CDCl$_3$) δ 7.24 (d, J=8.7 Hz, 2H), 7.17 (d, J=8.7 Hz, 2H), 2.86 (h, J=7.1 Hz, 1H), 1.72 (d, J=12.4 Hz, 1H), 1.69-1.58 (m, 4H), 1.46 (ddd, J=14.3, 8.1, 6.4 Hz, 1H), 1.39 (dt, J=13.9, 7.2 Hz, 1H), 1.19 (d, J=6.9 Hz, 3H), 1.18-1.06 (m, 4H), 0.91-0.82 (m, 2H). $^{13}$C NMR (126 MHz, CDCl$_3$) δ 148.86, 147.72, 128.76, 121.20, 118.9 (q, J=319 Hz), 46.35, 36.37, 35.16, 33.67, 33.47, 26.76, 26.35, 22.75. $^{19}$F NMR (470 Hz, CDCl$_3$) δ −75.06. R$_f$=0.30 on reverse phase TLC in 8/1 MeCN/H$_2$O. [α]$^{20}{}_D$=−62.6 (c 1.0, CHCl$_3$). HRMS (EI$^+$) Calculated for C$_{16}$H$_{21}$O$_3$F$_3$S: 350.11636; Found: 350.11738.

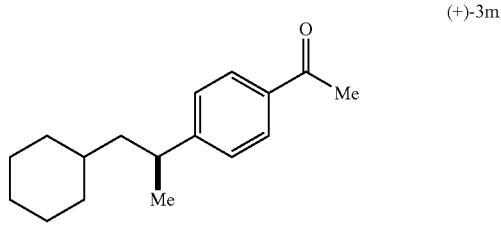 [SMILES: CC(=O)c1ccc([C@@H](C)CC2CCCCC2)cc1]

(+)-3m

Boronic acid (S)-1e (≥99:1 e.r.) was prepared in 66% yield by general procedure C and coupled to organohalide 2i to give product (+)-3m by general procedure D. The branched/linear product ratio of the crude reaction was determined to be 274/1 by HPLC (Eclipse XDB-C8 column, isocratic 70/30 MeCN/H$_2$O, 1.2 mL/min, 254.4 nm absorbance). Branched=9.8 minutes; linear=11.1 minutes. The product was isolated in 54% yield (13.6 mg) by purification with reverse phase flash chromatography (6/1 MeCN/H$_2$O) followed by normal phase flash chromatography (1/2 Hex/DCM). The e.r. of the purified product was determined to be 99.64:0.36 (>99% ES) using chiral HPLC (AD-RH chiral column, isocratic 72/28 MeCN/H$_2$O, 0.5 mL/min, 214 nm absorbance). Major=27.4 minutes; minor=33.5 minutes.

A duplicate run of the reaction gave a branched/linear product ratio of 285/1, isolated yield of 61%, and enantiospecificity of >99%.

$^1$H NMR (500 MHz, CDCl$_3$) δ 7.89 (d, J=8.3 Hz, 2H), 7.27 (d, J=8.3 Hz, 2H), 2.89 (h, J=8.3 Hz, 1H), 2.59 (s, 3H), 1.74 (d, J=12.6 Hz, 1H), 1.68-1.58 (m, 4H), 1.51 (ddd, J=14.3, 8.6, 6.1 Hz, 1H), 1.41 (m, 1H), 1.21 (d, J=6.9 Hz, 3H), 1.18-1.05 (m, 4H), 0.91-0.82 (m, 2H). $^{13}$C NMR (126 MHz, CDCl$_3$) δ 198.04, 154.17, 135.21, 128.71, 127.33, 46.14, 37.00, 35.22, 33.80, 33.36, 26.76, 26.69, 26.36, 26.34, 22.71 R$_f$=0.23 on reverse phase TLC in 6/1 MeCN/H$_2$O. R$_f$=0.29 on normal phase TLC in 1/2 Hex/DCM. [α]$^{20}{}_D$=+24.2 (c 1.0, CHCl$_3$). HRMS (EI$^+$) Calculated for C$_{17}$H$_{24}$O: 244.18272; Found: 244.18204.

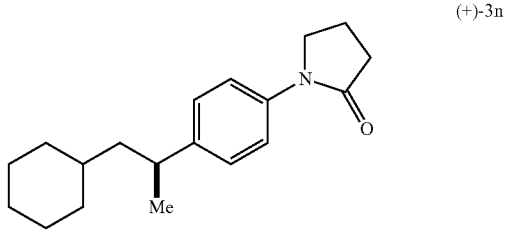 [SMILES: C[C@@H](CC1CCCCC1)c1ccc(N2CCCC2=O)cc1]

(+)-3n

Boronic acid (S)-1e (≥99:1 e.r.) was prepared in 65% yield by general procedure C and coupled to organohalide 2j to give product (+)-3n by general procedure D. The branched/linear product ratio of the crude reaction was determined to be 307/1 by HPLC (Eclipse XDB-C8 column, isocratic 65/35 MeCN/H$_2$O, 1.2 mL/min, 250 nm absorbance). Branched=9.6 minutes; linear=10.9 minutes. The product was isolated in 74% yield (21.4 mg) by purification with reverse phase flash chromatography (7/1 MeCN/H$_2$O) followed by normal phase flash chromatography (2/1 Hex/EtOAc). The e.r. of the purified product was determined to be 99.56:0.44 (>99% ES) using chiral HPLC (AD-RH chiral column, isocratic 45/45/10 MeCN/MeOH/H$_2$O, 0.5 mL/min, 214 nm absorbance). Major=24.2 minutes; minor=21.3 minutes.

A duplicate run of the reaction gave a branched/linear product ratio of 254/1, isolated yield of 61%, and enantiospecificity of >99%.

$^1$H NMR (500 MHz, CDCl$_3$) δ 7.50 (d, J=8.6 Hz, 2H), 7.17 (d, J=8.5 Hz, 2H), 3.86 (t, J=7.0 Hz, 2H), 2.80 (h, J=8.3 Hz, 1H), 2.60 (t, J=8.1 Hz, 2H), 2.15 (p, J=7.5 Hz, 2H), 1.75 (d, J=13.0 Hz, 1H), 1.67-1.55 (m, 4H), 1.48 (ddd, J=14.2, 8.7, 5.9 Hz, 1H), 1.36 (ddd, J=13.8, 7.9, 6.5 Hz, 1H), 1.17 (d, J=6.9 Hz, 3H), 1.16-1.06 (m, 4H), 0.91-0.79 (m, 2H). $^{13}$C NMR (126 MHz, CDCl$_3$) δ 174.17, 144.56, 137.19, 127.41, 120.19, 49.05, 46.40, 36.26, 35.10, 33.88, 33.32, 32.84, 26.82, 26.38, 26.35, 23.12, 18.25. R$_f$=0.22 on reverse phase TLC in 7/1 MeCN/H$_2$O. R$_f$=0.24 on normal phase TLC in 2/1 Hex/EtOAc. [α]$^{20}{}_D$=+38.2 (c 1.0, CHCl$_3$). HRMS (EI$^+$) Calculated for C$_{19}$H$_{27}$ON: 285.20927; Found: 285.20903.

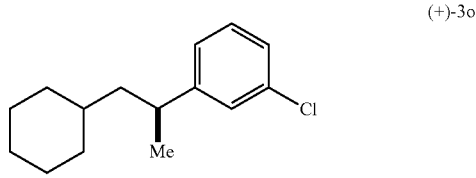 [SMILES: C[C@@H](CC1CCCCC1)c1cccc(Cl)c1]

(+)-3o

Boronic acid (S)-1e (≥99:1 e.r.) was prepared in 66% yield by general procedure C and coupled to organohalide 2k to give product (+)-3o by general procedure D. The branched/linear product ratio of the crude reaction was determined to be 94/1 by HPLC (Eclipse XDB-C8 column, isocratic 83/17 MeCN/H$_2$O, 1.2 mL/min, 215.4 nm absorbance). Branched=8.5 minutes; linear=9.6 minutes. The product was isolated in 78% yield (20.6 mg) by purification with reverse phase flash chromatography (15/1 MeCN/H$_2$O). The e.r. of the purified product was determined to be 99.18:0.82 (100% ES) using chiral HPLC (AD-RH chiral column, isocratic 75/25 MeCN/H$_2$O, 0.5 mL/min, 214 nm absorbance). Major=13.2 minutes; minor=11.6 minutes.

A duplicate run of the reaction gave a branched/linear product ratio of 86/1, isolated yield of 81%, and enantiospecificity of 100%.

$^1$H NMR (500 MHz, CDCl$_3$) δ 7.20 (td, J=7.6, 0.9 Hz, 1H), 7.17-7.13 (m, 2H), 7.05 (dt, J=7.6, 1.4 Hz, 1H), 2.80 (h, J=7.7 Hz, 1H), 1.73 (d, J=12.9 Hz, 1H), 1.69-1.58 (m, 4H), 1.47 (m, 1H), 1.37 (dt, J=13.9, 7.2 Hz, 1H), 1.18 (d, J=6.9 Hz, 3H), 1.18-1.07 (m, 4H), 0.92-0.81 (m, 2H). $^{13}$C NMR (126 MHz, CDCl$_3$) δ 150.45, 134.18, 129.68, 127.24, 126.02, 125.40, 46.25, 36.70, 35.15, 33.73, 33.45, 26.80, 26.37, 22.78. R$_f$=0.25 on reverse phase TLC in 15/1 MeCN/H$_2$O. [α]$^{20}{}_D$=+6.7 (c 1.0, CHCl$_3$). HRMS (EI$^+$) Calculated for C$_{15}$H$_{21}$Cl: 236.13318; Found: 236.13205.

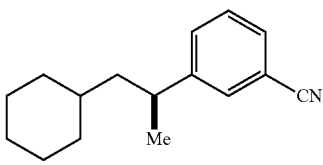

(−)-3p

Boronic acid (S)-1e (≥99:1 e.r.) was prepared in 66% yield by general procedure C and coupled to organohalide 21 to give product (−)-3p by general procedure D. The branched/linear product ratio of the crude reaction was determined to be 44/1 by HPLC (Eclipse XDB-C8 column, isocratic 70/30 MeCN/H$_2$O, 1.2 mL/min, 215.4 nm absorbance). Branched=10.8 minutes; linear=12.3 minutes. The product was isolated in 56% yield (12.9 mg) by purification with reverse phase flash chromatography (6/1 MeCN/H$_2$O) followed by normal phase flash chromatography (2/1 Hex/DCM). The e.r. of the purified product was determined to be 99.15:0.85 (>99% es) using chiral HPLC (AD-RH chiral column, isocratic 75/25 MeCN/H$_2$O, 0.5 mL/min, 214.4 nm absorbance). Major=10.0 minutes; minor=7.4 minutes.

A duplicate run of the reaction gave a branched/linear product ratio of 42/1, isolated yield of 55%, and enantiospecificity of >99%.

$^1$H NMR (500 MHz, CDCl$_3$) δ 7.49-7.45 (m, 2H), 7.43-7.36 (m, 2H), 2.86 (h, J=8.1 Hz, 1H), 1.75-1.58 (m, 5H), 1.47 (ddd, J=14.4, 8.4, 6.3 Hz, 1H), 1.40 (dt, J=13.9, 7.2 Hz, 1H), 1.20 (d, J=6.9 Hz, 3H), 1.17-1.03 (m, 4H), 0.92-0.82 (m, 2H). $^{13}$C NMR (126 MHz, CDCl$_3$) δ 149.63, 131.83, 130.81, 129.72, 129.24, 119.39, 112.43, 46.10, 36.65, 35.15, 33.70, 33.35, 26.71, 26.32, 22.68. R$_f$=0.26 on reverse phase TLC in 6/1 MeCN/H$_2$O. R$_f$=0.26 on normal phase TLC in 2/1 Hex/DCM. [α]$^{20}_D$=−74.4 (c 1.0, CHCl$_3$). HRMS (EI$^+$) Calculated for C$_{16}$H$_{21}$N: 227.16740; Found: 227.16723.

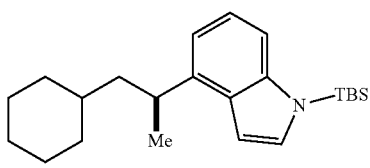

(+)-3q

Boronic acid (S)-1e (≥99:1 e.r.) was prepared in 67% yield by general procedure C and coupled to organohalide 2m to give product (+)-3q by general procedure D. The branched/linear product ratio of the crude reaction was determined to be 250/1 by HPLC (Eclipse XDB-C8 column, isocratic 90/10 MeCN/H$_2$O, 1.2 mL/min, 215.4 nm absorbance). Branched=12.0 minutes; linear=13.4 minutes. The product was isolated in 68% yield (24.7 mg) by purification with reverse phase flash chromatography (20/1 MeCN/H$_2$O). The e.r. of the purified product was determined to be 99.43:0.57 (>99% es) using chiral HPLC (AD-RH chiral column, isocratic 72/28 MeCN/H$_2$O, 0.4 mL/min, 214 nm absorbance). Major=22.7 minutes; minor=21.2 minutes.

A duplicate run of the reaction gave a branched/linear product ratio of 226/1, isolated yield of 75%, and enantiospecificity of >99%.

$^1$H NMR (500 MHz, CDCl$_3$) δ 7.35 (d, J=8.4 Hz, 1H), 7.16 (d, J=3.3 Hz, 1H), 7.10 (dd, J=8.3, 7.3 Hz, 1H), 6.95 (d, J=7.2 Hz, 1H), 6.68 (d, J=3.0 Hz, 1H), 3.29 (h, J=7.0 Hz, 1H), 1.81 (d, J=12.8 Hz, 1H), 1.77-1.58 (m, 5H), 1.48 (ddd, J=13.8, 8.1, 6.2 Hz, 1H), 1.32 (d, J=6.9 Hz, 3H), 1.35-1.27 (m, 1H), 1.23-1.09 (m, 3H), 0.94 (s, 9H), 0.97-0.86 (m, 2H), 0.60 (s, 3H), 0.59 (s, 3H). $^{13}$C NMR (126 MHz, CDCl$_3$) δ 141.17, 140.64, 130.29, 121.59, 116.24, 111.56, 103.20, 45.82, 35.46, 34.19, 33.69, 33.37, 26.92, 26.53, 26.50, 26.47, 21.49, 19.65, −3.75. R$_f$=0.19 on reverse phase TLC in 20/1 MeCN/H$_2$O. [α]$^{20}_D$=+26.3 (c 1.0, CHCl$_3$). HRMS (EI$^+$) Calculated for C$_{23}$H$_{38}$NSi: 356.2774; Found: 356.2769.

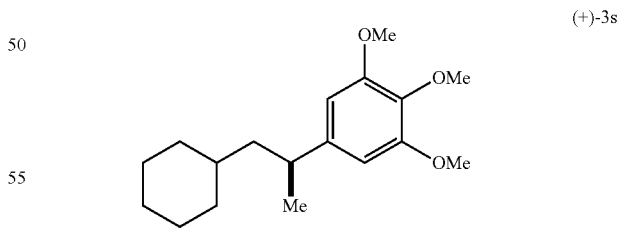

(+)-3r

Boronic acid (S)-1e (≥99:1 e.r.) was prepared in 67% yield by general procedure C and coupled to organohalide 2n to give product (+)-3r by general procedure D. The branched/linear product ratio of the crude reaction was determined to be 266/1 by HPLC (Eclipse XDB-C8 column, isocratic 70/30 MeCN/H$_2$O, 1.2 mL/min, 215.4 nm absorbance). Branched=9.8 minutes; linear=11.1 minutes. The product was isolated in 62% yield (15.0 mg) by purification with reverse phase flash chromatography (6/1 MeCN/H$_2$O). The e.r. of the purified product was determined to be 99.52:0.48 (>99% ES) using chiral HPLC (OD-H chiral column, isocratic 99.8/0.2 Hex/IPA, 2.0 mL/min, 210 nm absorbance). Major=7.3 minutes; minor=8.8 minutes.

A duplicate run of the reaction gave a branched/linear product ratio of 256/1, isolated yield of 55%, and enantiospecificity of >99%.

$^1$H NMR (500 MHz, CDCl$_3$) δ 6.80 (d, J=8.1 Hz, 1H), 6.74-6.69 (m, 2H), 3.88 (s, 3H), 3.86 (s, 3H), 2.76 (h, J=7.8H, 1H), 1.75 (d, J=12.7 Hz, 1H), 1.68-1.56 (m, 4H), 1.45 (ddd, J=14.3, 8.3, 6.3 Hz, 1H), 1.36 (dt, J=13.8, 7.1 Hz, 1H), 1.18 (d, J=6.9 Hz, 3H), 1.18-1.09 (m, 4H), 0.91-0.81 (m, 2H). $^{13}$C NMR (126 MHz, CDCl$_3$) δ 148.88, 147.12, 141.07, 118.81, 111.25, 110.42, 56.01, 55.98, 46.65, 36.43, 35.24, 33.80, 33.54, 26.85, 26.43, 23.09. [α]$^{20}_D$=+19.8 (c 1.2, CHCl$_3$). HRMS (EI$^+$) Calculated for C$_{17}$H$_{26}$O$_2$: 262.19328; Found: 262.19324.

(+)-3s

Boronic acid (S)-1e (≥99:1 e.r.) was prepared in 67% yield by general procedure C and coupled to organohalide 2o to give product (+)-3s by general procedure D. The branched/linear product ratio of the crude reaction was determined to be 100/1 by HPLC (Eclipse XDB-C8 column, isocratic 65/35 MeCN/H$_2$O, 1.2 mL/min, 215.4 nm absorbance). Branched=13.0 minutes; linear=15.1 minutes. The product was isolated in 71% yield (20.3 mg) by purification with reverse phase flash chromatography (5/1 MeCN/H$_2$O).

The e.r. of the purified product was determined to be 99.57:0.43 (>99% ES) using chiral HPLC (OD-H chiral column, isocratic 99.5/0.5 Hex/IPA, 2.0 mL/min, 214.4 nm absorbance). Major=4.69 minutes; minor=5.43 minutes.

A duplicate run of the reaction gave a branched/linear product ratio of 128/1, isolated yield of 74%, and enantiospecificity of >99%.

$^1$H NMR (500 MHz, CDCl$_3$) δ 6.39 (s, 2H), 3.86 (s, 6H), 3.83 (s, 3H), 2.75 (h, J=7.1 Hz, 1H), 1.76 (d, J=13.1 Hz, 1H), 1.70-1.58 (m, 4H), 1.45 (dt, J=14.2, 7.2 Hz, 1H), 1.37 (dt, J=13.8, 7.1 Hz, 1H), 1.19 (d, J=6.8 Hz, 3H), 1.22-1.11 (m, 4H), 0.92-0.82 (m, 2H). $^{13}$C NMR (126 MHz, CDCl$_3$) δ 153.15, 144.26, 136.07, 103.91, 60.97, 56.21, 46.56, 37.23, 35.23, 33.68, 26.83, 26.42, 22.80. $R_f$=0.24 on reverse phase TLC in 5/1 MeCN/H$_2$O. $[α]^{20}_D$=+17.1 (c 1.8, CHCl$_3$). HRMS (EI$^+$) Calculated for C$_{18}$H$_{28}$O$_3$: 292.20385; Found: 292.20380.

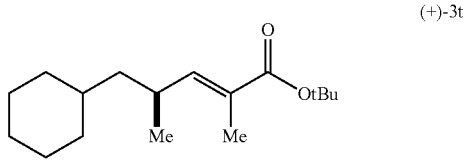 [SMILES: C/C(=C\[C@@H](C)CC1CCCCC1)C(=O)OC(C)(C)C]

(+)-3t

Boronic acid (S)-1e (≥99:1 e.r.) was prepared in 65% yield by general procedure C and coupled to organohalide 2p to give product (+)-3t by general procedure D. The branched/linear product ratio of the crude reaction was determined to be 888/1 by HPLC (Eclipse XDB-C8 column, isocratic 85/15 MeCN/H$_2$O, 1.2 mL/min, 214.4 nm absorbance). Branched=8.2 minutes; linear=8.9 minutes. The product was isolated in 64% yield (17.9 mg) by purification with normal phase flash chromatography (3/1 Hex/DCM). The e.r. of the purified product 50/50 MeCN/H$_2$O, 0.5 mL/min, 214.4 nm absorbance). Major=24.3 minutes; minor=26.5 minutes.

A duplicate run of the reaction gave a branched/linear product ratio of 1303/1, isolated yield of 68%, and enantiospecificity of 100%.

$^1$H NMR (500 MHz, CDCl$_3$) δ 6.41 (dd, J=10.0, 1.5 Hz, 1H), 2.57 (dq, J=10.3, 6.7 Hz, 1H), 1.78 (d, J=1.4 Hz, 4H), 1.71-1.60 (m, 5H), 1.49 (s, 9H), 1.26-1.07 (m, 6H), 0.95 (d, J=6.6 Hz, 3H), 0.90-0.78 (m, 2H). $^{13}$C NMR (126 MHz, CDCl$_3$) δ 168.07, 147.62, 127.37, 107.71, 80.01, 44.93, 35.34, 33.85, 33.59, 30.34, 28.31, 26.81, 26.43, 26.42, 20.38, 12.63. $R_f$=0.25 on normal phase TLC in 3/1 Hex/DCM. $[α]^{20}_D$=+28.7 (c 1.0, CHCl$_3$). HRMS (ES$^+$) Calculated for C$_{18}$H$_{28}$O$_3$: 289.2144; Found: 289.2136.

Example 5. Synthesis and Characterization of Xylarinic Acid B

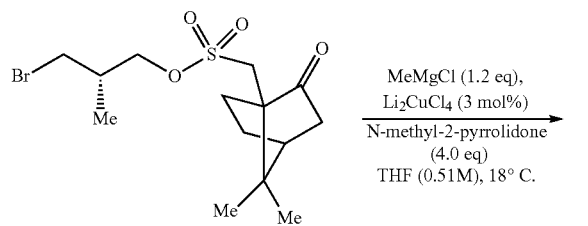

SI-12

MeMgCl (1.2 eq), Li$_2$CuCl$_4$ (3 mol%)
N-methyl-2-pyrrolidone (4.0 eq)
THF (0.51M), 18° C.

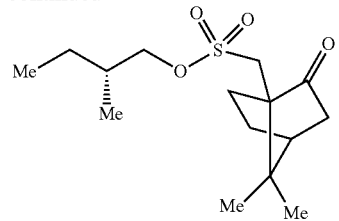

SI-13

Compound SI-13.

A flame-dried Schlenk flask was charged with alkyl bromide SI-12 (Mekala et al., *J. Org. Chem.* 2015, 80 (3), 1610) (5.47 g, 14.89 mmol, 1.0 eq). The flask was sealed, evacuated, and vac-filled with nitrogen three times. Anhydrous THF (14 mL), Li$_2$CuCl$_4$ (0.1M in THF, 4.5 mL, 0.45 mmol, 3 mol %), and N-methyl-2-pyrrolidone (5.7 mL, 59.23 mmol, 4.0 eq) was added via syringe under N$_2$. The reaction was cooled in an 18° C. water bath, and MeMgCl solution (1.7M in THF, 10.5 mL, 17.85 mmol, 1.2 eq) was added dropwise over 10 minutes. The reaction was stirred for 1 hour and 45 minutes. The reaction was then cooled to 0° C., then 1N HCl (50 mL) was added in one portion. The mixture was stirred until the solids dissolved and transferred to a separatory funnel with Et$_2$O (10 mL). After phase separation, the aqueous layer was extracted with Et$_2$O (2×30 mL). The organics were washed with H$_2$O (30 mL), brine, dried over MgSO$_4$, filtered, and concentrated in vacuo. The crude product was purified on a silica gel column (isocratic 15% EtOAc in hexanes). Mixed fractions were combined for a second silica gel column purification, affording the product SI-13 as a colorless oil (2.92 g, 9.65 mmol, 65% yield).

$^1$H NMR (500 MHz, CDCl$_3$) δ 4.17 (dd, J=9.4, 5.8 Hz, 1H), 4.05 (dd, J=9.4, 6.6 Hz, 1H), 3.60 (d, J=15.1 Hz, 1H), 2.98 (d, J=15.1 Hz, 1H), 2.50 (ddd, J=14.7, 11.8, 3.9 Hz, 1H), 2.39 (m, 1H), 2.12, (t, J=4.5 Hz, 1H), 2.06 (m, 1H), 1.95 (d, J=18.5 Hz, 1H), 1.79 (m, 1H), 1.65 (ddd, J=14.1, 9.4, 4.7 Hz, 1H), 1.52-1.41 (m, 2H), 1.22 (dp, J=13.5, 7.6 Hz, 1H), 1.12 (s, 3H), 0.97 (d, J=6.8 Hz, 3H), 0.92 (t, J=7.5 Hz, 3H), 0.88 (s, 3H). $^{13}$C NMR (126 MHz, CDCl$_3$) δ 214.71, 74.90, 58.08, 48.09, 46.64, 42.88, 42.66, 34.75, 27.02, 25.67, 25.01, 19.98, 19.84, 16.19, 11.23. HRMS (ES$^+$) Calculated for C$_{15}$H$_{26}$O$_4$NaS: 325.1449; Found: 325.1450.

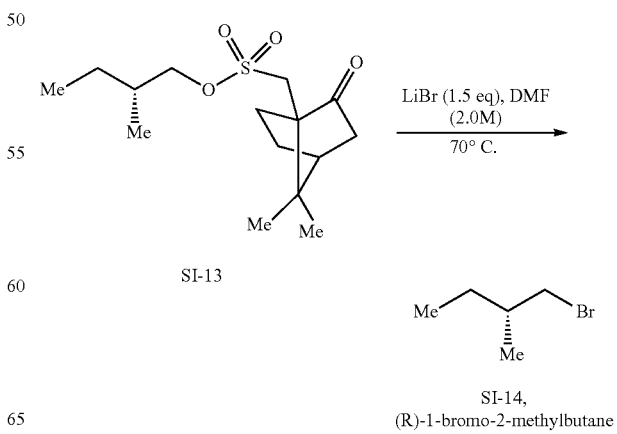

SI-13

LiBr (1.5 eq), DMF (2.0M)
70° C.

SI-14, (R)-1-bromo-2-methylbutane

(R)-1-bromo-2-methylbutane, (R)-SI-14

A solution of SI-13 (4.60 g, 15.2 mmol) in anhydrous DMF (6.5 mL) was prepared in a dry, stir bar-equipped 40 mL vial. This solution was then added to LiBr (1.98 g, 22.8 mmol, 1.5 eq) in another dry, stir bar-equipped 40 mL vial via syringe under nitrogen, rinsing with DMF (2×0.5 mL, total DMF=7.5 mL=2.0 Molar) for quantitative transfer. The reaction was stirred at 70° C. for one hour, then cooled to room temperature and transferred to two 50 mL centrifuge tubes, rinsing with DMF (3×0.5 mL). To each centrifuge tube was added H$_2$O (40 mL). After shaking, the phases were separated by centrifugation (3000 rpm for three minutes, then 4000 rpm for three minutes). In both centrifuge tubes, the aqueous layer on top was removed by pipet and fresh H$_2$O was added to the 40 mL mark. After mixing, the phases were again separated by centrifugation by the same procedure. The oil at the bottom of each centrifuge tube was removed and passed through a short pad of a mixture consisting of celite and Na$_2$SO$_4$ in a Pasteur pipette into a tared 7 mL vial, giving the (R)-SI-14 as a clear colorless oil (1.76 g, 11.6 mmol, 76%). NMR matches that reported in the literature (Reiss et al., *Organic Letters* 2009, 11 (15), 3286).

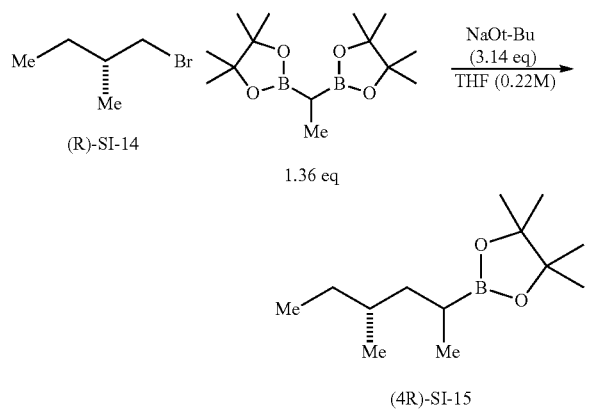

SI Compound (4R)-SI-15.

The pinacol boronic ester was synthesized by a modified literature procedure. In an inert atmosphere glovebox, a stir bar-equipped 250 mL Schlenk flask was charged with NaOt-Bu (2.87 g, 29.8 mmol, 3.15 eq). A separate 40 mL vial was charged with (R)-1-bromo-2-methylbutane (R)-SI-14 (1.43 g, 9.47 mmol, 1.00 eq) and Et(Bpin)$_2$ (3.63 g, 12.9 mmol, 1.36 eq). The Schlenk flask was sealed with a rubber septum, and the 40 mL was sealed with a septa cap. Both vessels were brought out of the glovebox and into a fume hood and connected to nitrogen lines. Anhydrous THF (29 mL) was added to the Schlenk flask, resulting in a cloudy, light yellow suspension. The mixture of alkyl bromide and Et(Bpin)$_2$ was then added (at room temperature, dropwise over five minutes) to the Schlenk flask, using additional THF (2×7 mL, total THF=43 mL=0.22 Molar) for quantitative transfer. The reaction was stirred efficiently at room temperature overnight.

The next day, the reaction was diluted with Et$_2$O (75 mL) and filtered through a pad of silica gel in a coarse glass frit. The filtrate was concentrated by rotary evaporation, giving a colorless oil of low viscosity. The crude product was purified by normal phase column chromatography (6 cm diameter, 250 mL silica gel, isocratic 4/1 Hex/DCM), giving the product as a colorless oil (1.34 g, 5.94 mmol, 63% yield).

1H NMR (500 MHz, CDCl$_3$) δ 1.47 (ddd, J=12.9, 8.9, 5.4 Hz, 1H), 1.40-1.27 (m, 4H), 1.22 (d, J=2.2 Hz, 26H), 1.15-1.00 (m, 5H), 0.93 (dd, J=8.9, 7.3 Hz, 6H), 0.89-0.78 (m, 12H). $^{13}$C NMR (126 MHz, CDCl$_3$) δ 82.72, 82.70, 40.53, 39.87, 33.62, 32.96, 29.68, 29.51, 24.74, 24.70, 24.69, 24.65, 19.45, 18.88, 16.08, 15.35, 11.43.

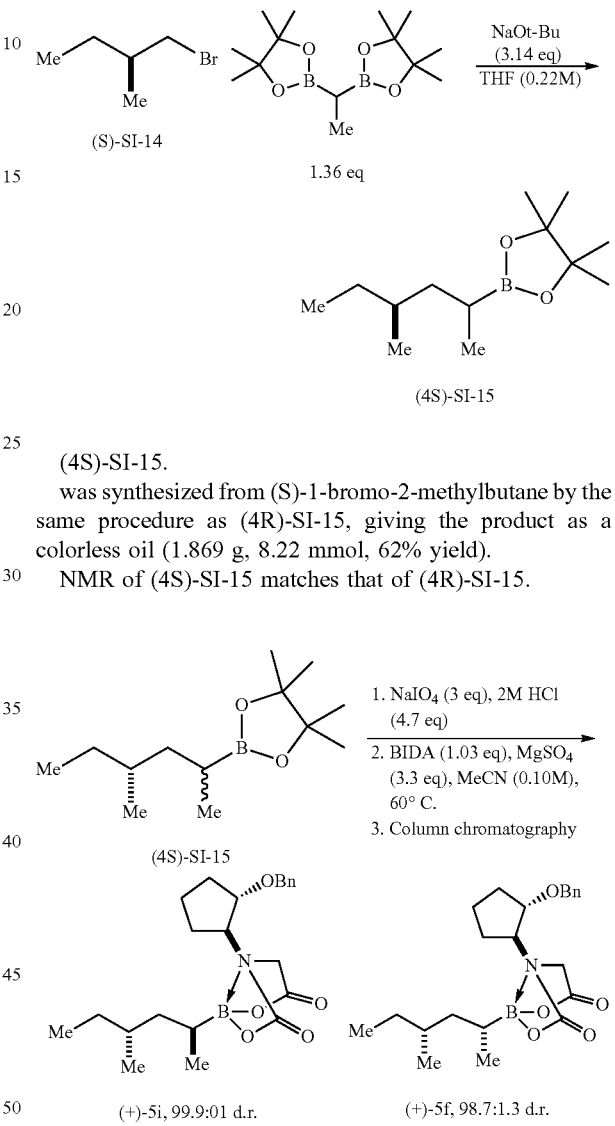

(4S)-SI-15.

was synthesized from (S)-1-bromo-2-methylbutane by the same procedure as (4R)-SI-15, giving the product as a colorless oil (1.869 g, 8.22 mmol, 62% yield).

NMR of (4S)-SI-15 matches that of (4R)-SI-15.

BIDA Boronates 5i and 5f.

To a stir bar-equipped 300 mL round bottom flask was added the pinacol boronic ester (4S)-SI-15 (1.442 g, 6.37 mmol, 1.00 eq) followed by THF (43 mL, 0.15 M), H$_2$O (6.1 mL), and 1 Molar HCl (4.3 mL, 4.3 mmol, 0.68 eq). After five hours, monitoring of the reaction by TLC (3/1 Hex/EtOAc) still showed a substantial amount of the starting boronic ester. Additional 5.5 Molar HCl (4.6 mL, 25.3 mmol, 4.0 eq) was added to increase the total amount of HCl (2 Molar, 4.7 eq). The reaction was stirred for another hour and 15 minutes, at which point TLC indicated full consumption of the pinacol boronic ester. The stir bar was removed, additional H$_2$O (15 mL) was added, and THF was removed by rotary evaporation. The reaction was diluted with additional H₂O (15 mL) and extracted with methyl tert-butyl ether (2×40 mL). Combined organics were washed repeatedly with H₂O (10×35 mL) to remove any remaining oxidant and then once with brine (35 mL). After drying with MgSO₄ and filtering through a glass frit into a 500 mL round bottom flask, the solution was partially concentrated (remaining volume of 5-10 mL) and then the solvent was switched to anhydrous MeCN (64 mL, 0.10 Molar). BIDA (2.01 g, 6.54 mmol, 1.03 eq) and MgSO₄ (2.55 g, 21.2 mmol, 3.3 eq) were added, along with a stir bar. The reaction was sealed with a rubber septum and connected to a nitrogen line before stirring overnight at 60° C.

The next day, the reaction mixture was filtered through a plug of silica gel, rinsing with EtOAc. The filtrate was concentrated by rotary evaporation, giving a red foam (2.06 g, 4.97 mmol, 78% crude yield). This material was subjected to normal phase column chromatography (15/1 MTBE/EtOAc or 1/1 Hex/EtOAc). Mixed fractions were repurified until the d.r. of both diastereomers was ≥99:1 as determined by a sequence of stereospecific oxidation to the alcohol and derivatization to the para-nitrobenzoate ester (described below). The absolute configuration of the stereocenters was determined as described below. The higher R$_f$ diastereomer (5i, R,S; 0.549 g, 1.32 mmol, 21% yield) was isolated as a white powder, and so was the lower R$_f$ diastereomer (5f, R,R; 0.498 g, 1.20 mmol, 19% yield).

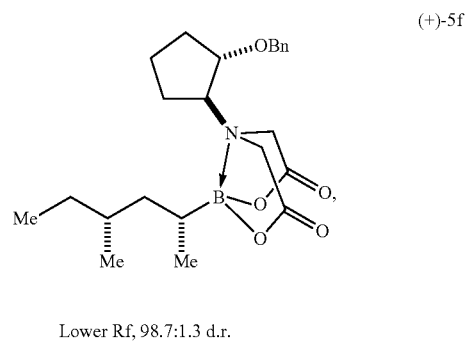

(+)-5f

Lower Rf, 98.7:1.3 d.r.

¹H NMR (500 MHz, acetone-d₆) δ 7.41-7.34 (m, 4H), 7.30 (m, 1H), 4.65 (d, J=11.5 Hz, 1H), 4.58 (d, J=11.5 Hz, 1H), 4.37 (dt, J=7.5, 5.0 Hz, 1H), 4.13 (dd, J=17.2, 2.8 Hz, 2H), 4.05 (d, J=16.9 Hz, 1H), 3.97 (d, J=17.4 Hz, 1H), 3.77 (td, J=8.7, 6.0 Hz, 1H), 2.28 (m, 1H), 2.14 (m, 1H), 1.88-1.74 (m, 3H), 1.68 (ddt, J=13.3, 9.2, 7.9 Hz, 1H), 1.52 (dddtd, J=18.2, 14.7, 7.0, 3.6 Hz, 2H), 1.22 (m, 1H), 1.12-1.02 (m, 2H), 1.01-0.93 (m, 1H), 0.93 (d, J=6.4 Hz, 3H), 0.86-0.81 (m, 6H). ¹³C NMR (126 MHz, acetone-d₆) δ 169.30, 168.02, 138.68, 128.82, 128.17, 128.13, 80.63, 73.12, 71.79, 60.28, 57.54, 39.87, 31.80, 30.34, 27.56, 27.24, 21.90, 20.54, 14.82, 11.02. ¹¹B NMR (128 MHz, acetone-d₆) δ 13.67. $[α]^{20}_D$=+55.6 (c 1.0 acetone). HRMS (ES⁺) Calculated for $C_{23}H_{35}BNO_5$: 416.2608; Found: 416.2608.

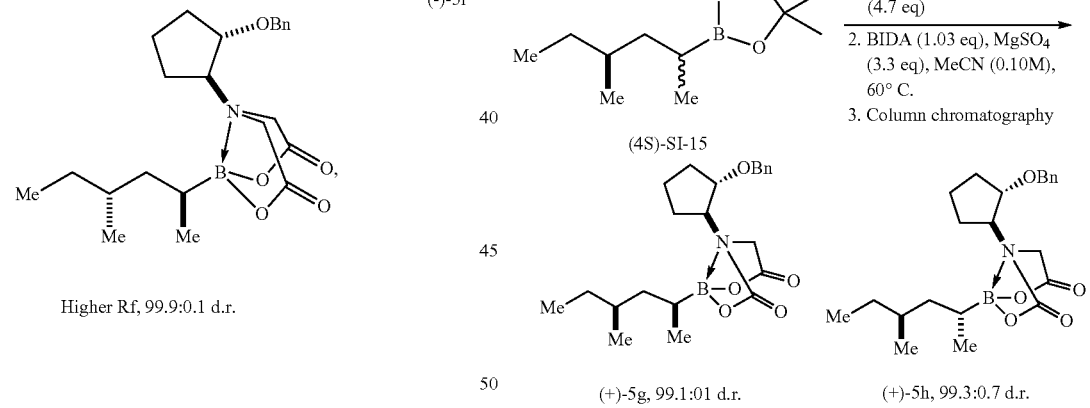

(-)-5i

Higher Rf, 99.9:0.1 d.r.

(4S)-SI-15

1. NaIO₄ (3 eq), 2M HCl (4.7 eq)
2. BIDA (1.03 eq), MgSO₄ (3.3 eq), MeCN (0.10M), 60° C.
3. Column chromatography (+)-5g, 99.1:01 d.r.

(+)-5h, 99.3:0.7 d.r.

¹H NMR (500 MHz, acetone-d6) δ 7.43-7.39 (m, 2H), 7.38-7.34 (m, 2H), 7.33-7.27 (m, 1H), 4.65 (d, J=11.3 Hz, 1H), 4.59 (d, J=11.2 Hz, 1H), 4.41 (m, 1H), 4.16-4.04 (m, 3H), 3.95 (d, J=17.5 Hz, 1H), 3.79 (td, J=8.7, 6.4 Hz, 1H), 2.28 (m, 1H), 2.19 (m, 1H), 1.88-1.77 (m 3H), 1.62 (m, 1H), 1.45 (dtd, J=13.5, 6.6, 3.4 Hz, 1H), 1.33-1.13 (m, 4H), 1.08 (dqd, J=10.1, 6.6, 3.3 Hz, 1H), 0.87 (t, J=7.4 Hz, 3H), 0.81 (dd, J=6.7, 1.4 Hz, 6H). ¹³C NMR (126 MHz, acetone-d6) δ 169.70, 167.90, 138.63, 128.85, 128.49, 128.20, 80.79, 72.88, 71.98, 60.70, 56.80, 39.57, 31.94, 31.30, 30.17, 27.01, 21.74, 18.32, 14.44, 11.65. ¹¹B NMR (128 MHz, acetone-d6) δ 14.48. $[α]^{20}_D$=-0.5 (c=1.0, acetone). HRMS (ES+) Calculated for $C_{23}H_{35}BNO_5$: 416.2608; Found: 416.2608.

BIDA Boronates 5g and 5h.

To a stir bar-equipped 300 mL round bottom flask was added the pinacol boronic ester (4S)-SI-15 (1.859 g, 8.22 mmol, 1.00 eq) followed by THF (55 mL, 0.15 M) and 2 Molar HCl (19 mL, 38 mmol, 6.0 eq). Once the reaction was complete by TLC (3/1 Hex/EtOAc), the stir bar was removed, additional H₂O (20 mL) was added, and THF was removed by rotary evaporation. The reaction was diluted with more H₂O (20 mL) and extracted with methyl tert-butyl ether (2×50 mL). Combined organics were washed repeatedly with H₂O (10×45 mL) to remove any remaining oxidant and then once with brine (50 mL). After drying with MgSO₄ and filtering through a glass frit into a 500 mL round bottom flask, the solution was partially concentrated (remaining volume of 5-10 mL) and then the solvent was switched to anhydrous MeCN (84 mL, 0.10 Molar). BIDA (2.53 g, 8.22 mmol, 1.00 eq) and MgSO$_4$ (3.28 g, 27.3 mmol, 3.3 eq) were added, along with a stir bar. The reaction was sealed with a rubber septum and connected to a nitrogen line before stirring overnight at 60° C.

The next day, the reaction mixture was filtered through a plug of silica gel, rinsing with EtOAc. The filtrate was concentrated by rotary evaporation, giving a red foam. This material was subjected to normal phase column chromatography (gradient 1.2/1 Hex/EtOAc to 1/1.2 Hex/EtOAc). Mixed fractions were repurified until the d.r. of both diastereomers was ≥99:1 as determined by a sequence of stereospecific oxidation to the alcohol and derivatization to the para-nitrobenzoate ester (described below). The absolute configuration of the stereocenters was determined as described below. The higher R$_f$ diastereomer (5g, S,S; 0.8222 g, 1.98 mmol, 24% yield) was isolated as white powder, and so was the lower R$_f$ diastereomer (5h, S,R; 1.2124 g, 2.92 mmol, 36% yield).

(+)-5g

Higher Rf, 99.9:0.1 d.r.

$^1$H NMR (500 MHz, CDCl$_3$) δ 7.43-7.35 (m, 3H), 7.31-7.28 (2H), 4.65 (d, J=11.5 Hz, 1H), 4.38 (d, J=11.5 Hz, 1H), 4.02 (d, J=16.7 Hz, 1H), 3.91 (q, J=6.8 Hz, 1H), 3.65 (m, 1H), 3.61 (d, J=17.0 Hz, 1H), 3.44 (d, J=16.6 Hz, 1H), 3.32 (d, J=16.9 Hz, 1H), 2.21 (m, 1H), 2.08 (m, 1H), 1.88 (m, 1H), 1.82-1.69 (m, 2H), 1.50 (m, 1H), 1.40 (dqd, J=14.8, 7.5, 3.2 Hz, 1H), 1.09 (p, J=9.1 Hz, 1H), 1.02-0.89 (m, 2H), 0.88-0.82 (m, 9H). $^{13}$C NMR (126 MHz, CDCl$_3$) δ 169.02, 167.43, 136.44, 128.73, 128.43, 128.19, 79.27, 71.98, 71.92, 60.79, 56.05, 39.35, 31.16, 29.56, 27.55, 26.45, 21.36, 20.16, 14.86, 10.99. $^{11}$B NMR (128 MHz, CDCl$_3$) δ 14.14. [α]$^{20}_D$=+6.5 (c 1.09, CDCl$_3$). HRMS (ES$^+$) Calculated for C$_{23}$H$_{33}$BNO$_5$: 414.2452; Found: 414.2448.

(+)-5h

Lower Rf, 99.3:0.7 d.r.

$^1$H NMR (500 MHz, CDCl$_3$) δ 7.43-7.35 (m, 3H), 7.31-7.28 (m, 2H), 4.66 (d, J=11.7 Hz, 1H), 4.39 (d, J=11.6 Hz, 1H), 4.04 (d, J=16.7 Hz, 1H), 3.89 (q, J=6.6 Hz, 1H), 3.65 (q, J=8.1 Hz, 1H), 3.63 (dd, J=17.0 Hz, 1H), 3.41 (d, J=16.7 Hz, 1H), 3.33 (d, J=16.9 Hz, 1H), 2.23 (m, 1H), 2.05 (m, 1H), 1.88-1.69 (m, 3H), 1.53-1.44 (m, 2H), 1.33-1.13 (m, 4H), 0.99-0.92 (m, 4H), 0.87 (t, J=7.4 Hz, 3H), 0.83 (d, J=6.5 Hz, 3H), 0.79 (m, 1H). $^{13}$C NMR (126 MHz, CDCl$_3$) δ 168.96, 167.56, 136.62, 128.89, 128.58, 128.23, 79.17, 71.92, 61.00, 56.66, 38.96, 31.61, 31.19, 29.66, 26.75, 21.48, 18.54, 14.35, 11.83. [α]$^{20}_D$=+32.4 (c 1.09, CDCl$_3$). HRMS (ES+) Calculated for C$_{23}$H$_{34}$BNO$_5$Na: 438.2428; Found: 438.2423.

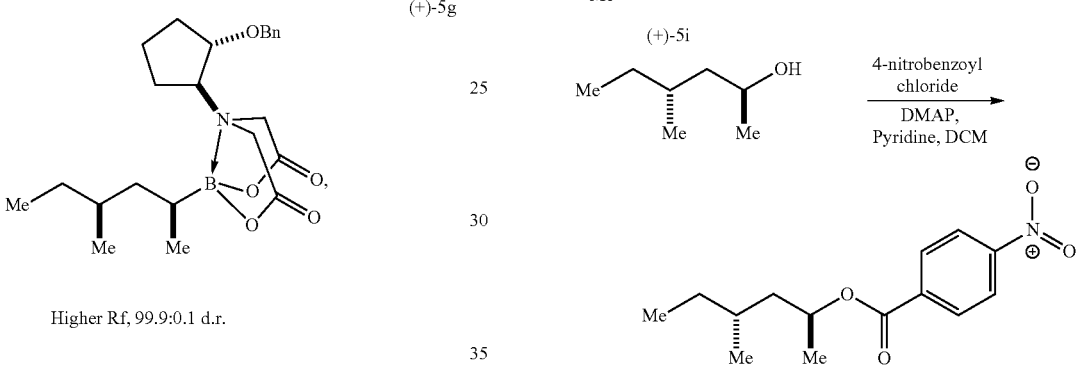

SI-16

SI-16.

BIDA boronate (−)-5i (10.4 mg, 0.025 mmol, 1.0 eq) was added to a stir bar-equipped 7 mL vial. THF (0.25 mL) and 1 M NaOH (0.25 mL, 10 eq) were added. The reaction was stirred at room temperature until full conversion to the boronic acid was observed by TLC (1:1 Hex/EtOAc, KMnO$_4$ stain). To the reaction was added 30% aqueous H$_2$O$_2$ (0.05 mL, 0.5 mmol, 20 eq), and the reaction was allowed to stir at room temperature until full conversion of the alcohol was observed by TLC (1:1 Hex/EtOAc, KMnO$_4$ stain). The reaction was diluted with Et$_2$O (15 mL) and quenched with saturated aqueous Na$_2$S$_2$O$_3$ (15 mL). After the organic layer was mixed and separated, it was washed with brine (15 mL), dried with Na$_2$SO$_4$, and concentrated under mild vacuum to afford (2S,4R)-4-methylhexan-2-ol.

To a solution of the crude alcohol in anhydrous DCM (0.5 mL, 0.05 Molar) in a stir bar-equipped 7 mL vial was added anhydrous pyridine (7 μL, 7 mg, 0.09 mmol, 1.8 eq), 4-nitrobenzoyl chloride (13 mg, 0.07 mmol, 1.4 eq) and 4-(dimethylamino)pyridine (0.6 mg, 0.005 mmol, 10 mol %). The vial was capped and stirred at room temperature overnight. The next day, the reaction mixture was passed through a pad of MgSO$_4$ in a cotton-plugged glass pipet, and filtrate was concentrated in vacuo. The crude product was purified by normal phase column chromatography (1:1 Hex/DCM), giving the pure 4-nitrobenzoate ester SI-16.

The product was analyzed by reverse phase HPLC (AD-RH column, isocratic 62:38 MeCN/H$_2$O, 0.5 mL/min, 214.4 nm), giving a d.r. of 99.9:0.1.

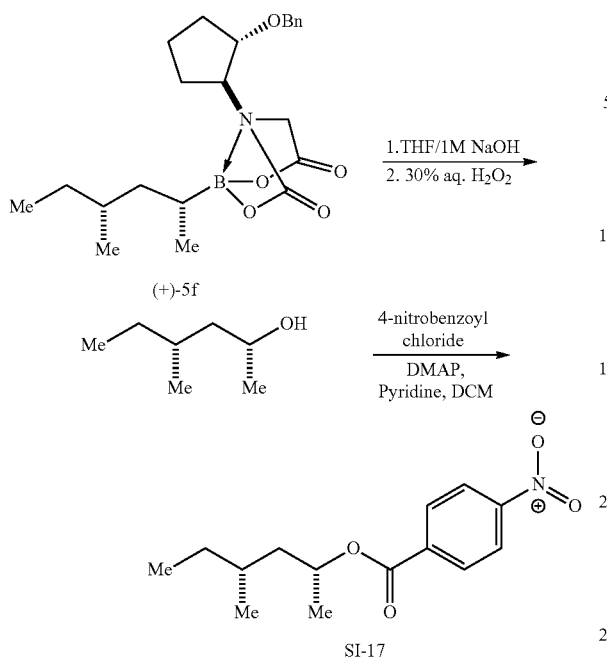

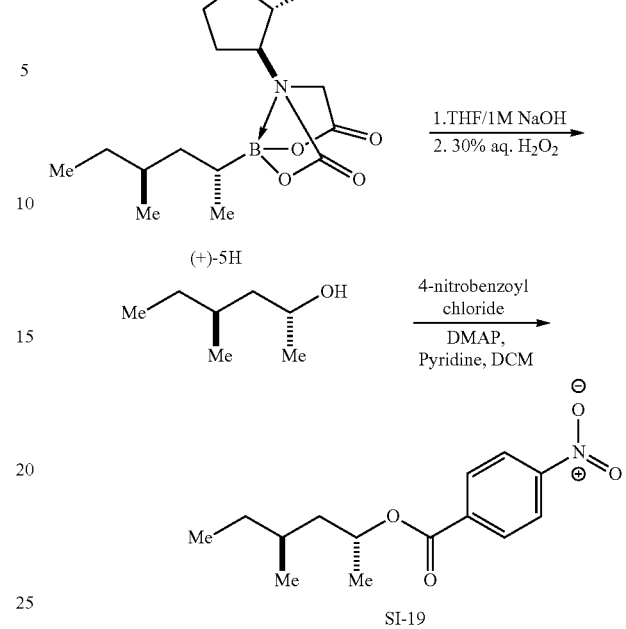

SI-17 was prepared following the same procedure as for SI-16. Using the same HPLC conditions as for SI-16, the d.r. was determined to be 98.7:0.3.

SI-19 was prepared following the same procedure as for SI-16. Using the same HPLC conditions as for SI-16, the d.r. was determined to be 99.3:0.7.

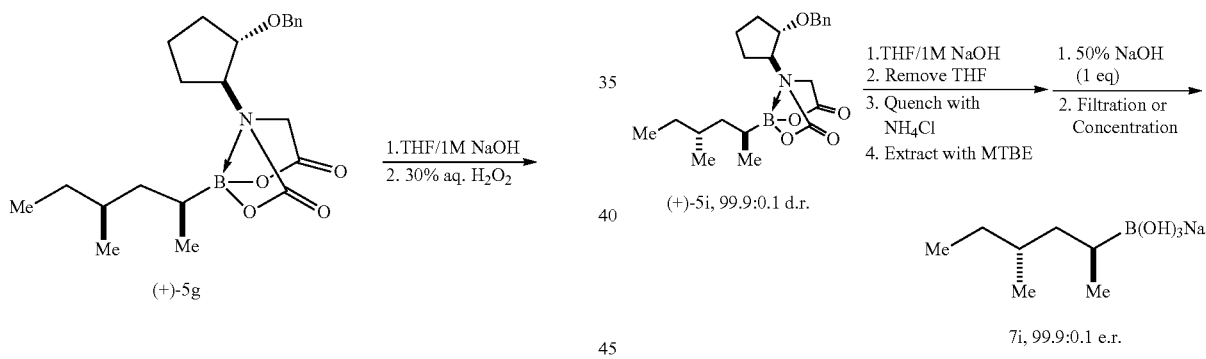

7i was made from BIDA boronate (−)-5i in quantitative yield as a white solid using general procedure B by directly concentrating the suspension without filtration.

$^1$H NMR (500 MHz, CD$_3$OD) 1.38 (dq, J=12.8, 6.2 Hz, 1H), 1.26 (ddd, J=13.5, 7.6, 5.9 Hz, 1H), 1.21-1.10 (m, 3H), 0.88 (t, J=7.4 Hz, 3H), 0.81 (d, J=6.5 Hz, 3H), 0.78 (d, J=7.1 Hz, 3H), 0.66 (d, J=10.7 Hz, 1H). $^{13}$C NMR (126 MHz, CD$_3$OD) δ 41.78, 33.89, 32.73, 19.00, 16.08, 12.26. $^{11}$B NMR (128 MHz, CD$_3$OD) δ 7.47. [α]$^{20}_D$=−32.8 (c 1.03, CD$_3$OD).

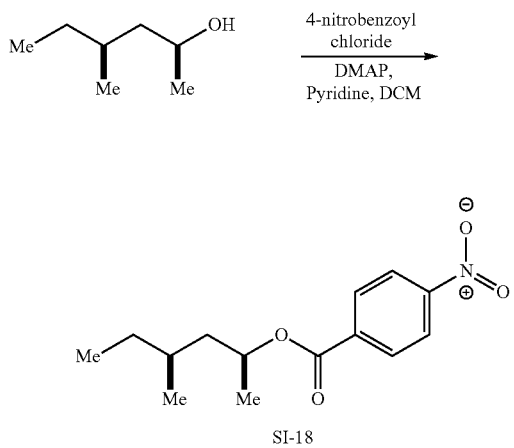

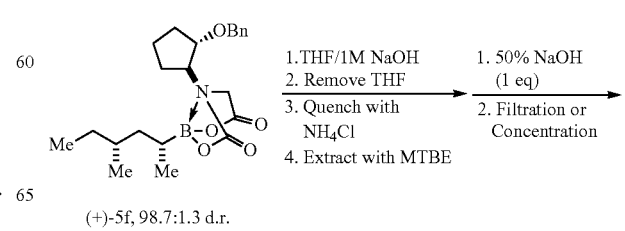

SI-18 was prepared following the same procedure as for SI-16. Using the same HPLC conditions as for SI-16, the d.r. was determined to be 99.9:0.1.

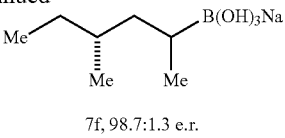

7f, 98.7:1.3 e.r.

7f was made from BIDA boronate (+)-5f in quantitative yield as a white solid using general procedure B by directly concentrating the suspension without filtration.

$^1$H NMR (500 MHz, CD$_3$OD) 1.54 (m, 1H), 1.45-1.32 (m, 2H), 1.02-0.88 (m, 2H), 0.88-0.83 (m, 6H), 0.80 (d, J=7.1 Hz, 3H), 0.68 (br s, 1H). $^{13}$C NMR (126 MHz, CD$_3$OD) δ 42.60, 34.06, 28.99, 21.36, 16.59, 11.91. $^{11}$B NMR (128 MHz, CD$_3$OD) δ 7.74.

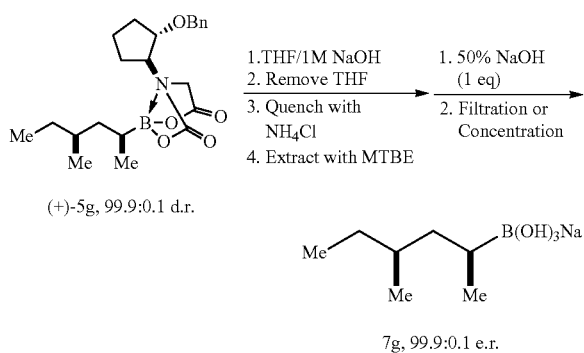

(+)-5g, 99.9:0.1 d.r.

7g, 99.9:0.1 e.r.

7g was made from BIDA boronate (+)-5g in quantitative yield as a white solid using general procedure B by directly concentrating the suspension without filtration. $^1$H NMR matches that of 7f.

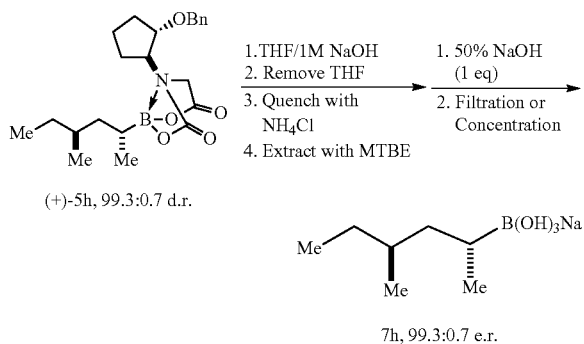

(+)-5h, 99.3:0.7 d.r.

7h, 99.3:0.7 e.r.

7h was made from BIDA boronate (+)-5h in quantitative yield as a white solid using general procedure B by directly concentrating the suspension without filtration. NMR matches that of 7i.

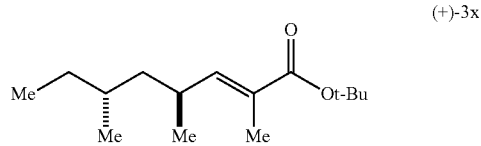 [SMILES: CC[C@@H](C)C[C@H](C)/C=C(\C)C(=O)OC(C)(C)C]

(+)-3x

Boronic acid 1f (99.9:0.1 e.r.) was prepared in 73% yield by general procedure C and coupled to organohalide 2p to give product (+)-3x by general procedure D. The branched/linear product ratio of the crude reaction was determined to be 396/1 by HPLC (Eclipse XDB-C8 column, isocratic 75/25 MeCN/H$_2$O, 1.2 mL/min, 214.4 nm absorbance). Branched=10.8 minutes; linear=11.7 minutes. The product was isolated in 69% yield (16.6 mg) by purification with normal phase flash chromatography (2/1 Hex/DCM). The d.r. of the purified product was determined by a sequence of deprotection and derivatization to the corresponding phenyl amide (SI-16) to be 99.6:0.4 (99.4% DS).

A duplicate run of the reaction gave a branched/linear product ratio of 516/1, isolated yield of 65%, and diastereospecificity of 99.4%.

$^1$H NMR (500 MHz, CDCl$_3$) δ 6.43 (dq, J=9.8, 1.4 Hz, 1H), 2.55 (dp, J=10.0, 6.7 Hz, 1H), 1.78 (d, J=1.5 Hz, 3H), 1.48 (s, 9H), 1.38-1.24 (m, 3H), 1.16-1.04 (m, 2H), 0.95 (d, J=6.6 Hz, 3H), 0.88-0.80 (m, 6H). $^{13}$C NMR (126 MHz, CDCl$_3$) δ 168.07, 147.64, 127.21, 80.01, 43.96, 32.05, 30.85, 29.50, 28.30, 19.94, 19.51, 12.60, 11.35. $[\alpha]^{22}_D$=+13.3 (c. 0.43, CDCl$_3$). HRMS (ES$^+$) Calculated for C$_{15}$H$_{28}$O$_2$Na: 263.1987; Found: 263.1980.

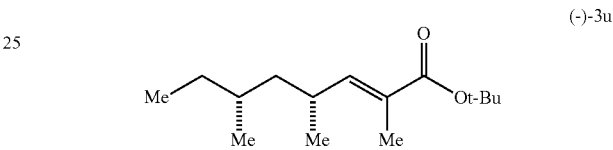

(−)-3u

Boronic acid 1g (98.7:1.3 e.r.) was prepared in 56% yield by general procedure C and coupled to organohalide 2p to give product (−)-3u by general procedure D. The branched/linear product ratio of the crude reaction was determined to be 402/1 by HPLC (Eclipse XDB-C8 column, isocratic 75/25 MeCN/H$_2$O, 1.2 mL/min, 214.4 nm absorbance). Branched=11.0 minutes; linear=11.9 minutes. The product was isolated in 57% yield (14.0 mg) by purification with normal phase flash chromatography (2/1 Hex/DCM). The d.r. of the purified product was determined by a sequence of deprotection and derivatization to the corresponding phenyl amide (SI-17) to be 98.0:2.0 (98.6% DS).

A duplicate run of the reaction gave a branched/linear product ratio of 381/1, isolated yield of 57%, and diastereospecificity of 98.5%.

$^1$H NMR (500 MHz, CDCl$_3$) δ 6.39 (dq, J=10.2, 1.5 Hz, 1H), 2.57 (dddd, J=16.2, 11.8, 8.2, 5.6 Hz, 1H), 1.79 (d, J=1.5 Hz, 3H), 1.48 (s, 9H), 1.37-1.20 (m, 3H), 1.17-1.06 (m, 2H), 0.97 (d, J=6.6 Hz, 3H), 0.85 (t, J=7.4 Hz, 3H), 0.82 (d, J=6.4 Hz, 3H). $^{13}$C NMR (126 MHz, CDCl$_3$) δ 168.02, 147.41, 127.59, 109.91, 80.00, 44.34, 32.33, 30.95, 30.09, 28.30, 20.72, 19.26, 12.67, 11.35. $[\alpha]^{22}_D$=−39.1 (c. 0.99, CDCl$_3$). HRMS (ES$^+$) Calculated for C$_{15}$H$_{28}$O$_2$Na: 263.1987; Found: 263.1978.

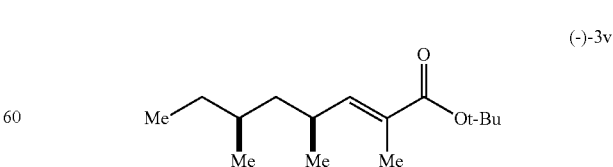

(−)-3v

Boronic acid 1h (99.9:0.1 e.r.) was prepared in 65% yield by general procedure C and coupled to organohalide 2p to give product (−)-3v by general procedure D. The branched/linear product ratio of the crude reaction was determined to be 181/1 by HPLC (Eclipse XDB-C8 column, isocratic 75/25 MeCN/H$_2$O, 1.2 mL/min, 214.4 nm absorbance). Branched=10.7 minutes; linear=11.7 minutes. The product was isolated in 46% yield (11.9 mg) by purification with normal phase flash chromatography (2/1 Hex/DCM). The d.r. of the purified product was determined by a sequence of deprotection and derivatization to the corresponding phenyl amide (SI-18) to be 99.2:0.4 (98.6% DS).

A duplicate run of the reaction gave a branched/linear product ratio of 600/1, isolated yield of 54%, and diastereospecificity of 99.0%.

$^1$H NMR matches that of (−)-3u. $^{13}$C NMR matches that of (−)-3u. $[\alpha]^{22}_D$=−39.1 (c. 0.99, CDCl$_3$).

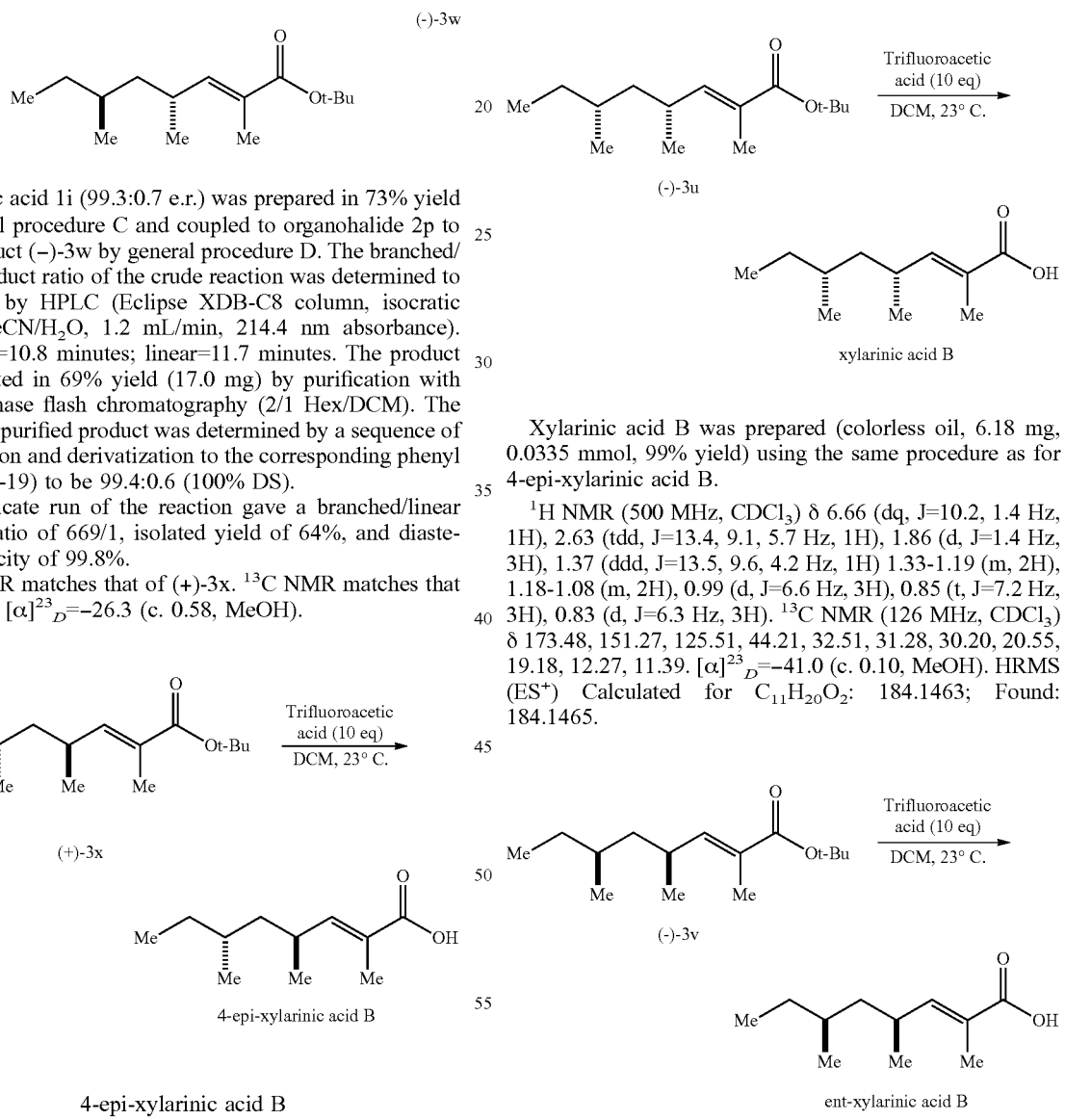

(-)-3w

Boronic acid 1i (99.3:0.7 e.r.) was prepared in 73% yield by general procedure C and coupled to organohalide 2p to give product (−)-3w by general procedure D. The branched/linear product ratio of the crude reaction was determined to be 618/1 by HPLC (Eclipse XDB-C8 column, isocratic 75/25 MeCN/H$_2$O, 1.2 mL/min, 214.4 nm absorbance). Branched=10.8 minutes; linear=11.7 minutes. The product was isolated in 69% yield (17.0 mg) by purification with normal phase flash chromatography (2/1 Hex/DCM). The d.r. of the purified product was determined by a sequence of deprotection and derivatization to the corresponding phenyl amide (SI-19) to be 99.4:0.6 (100% DS).

A duplicate run of the reaction gave a branched/linear product ratio of 669/1, isolated yield of 64%, and diastereospecificity of 99.8%.

$^1$H NMR matches that of (+)-3x. $^{13}$C NMR matches that of (+)-3x. $[\alpha]^{23}_D$=−26.3 (c. 0.58, MeOH).

4-epi-xylarinic acid B

A stir bar-equipped, 2 mL screw-cap vial was charged with the tert-butyl ester (+)-3x (12.1 mg, 0.0503 mmol). DCM (0.50 mL, 0.10 Molar) was added, followed by trifluoroacetic acid (dropwise over 1 minute at room temperature, 39 μL, 58 mg, 0.51 mmol, 10 eq). The vial was capped and stirred at room temperature for four hours. At this time, TLC (10% EtOAc in hexanes, KMnO$_4$ stain) showed complete conversion to a more polar spot. The solvent and trifluoroacetic acid were removed by rotary evaporation. Toluene was added and evaporated three times to remove residual trifluoroacetic acid. The carboxylic acid was obtained as a colorless oil (9.55 mg, 0.518 mmol, quantitative yield) without purification.

$^1$H NMR (500 MHz, CDCl$_3$) δ 6.70 (dq, J=10.2, 1.4 Hz, 1H), 2.61 (dh, J=9.4, 6.7 Hz, 1H), 1.84 (d, J=1.4 Hz, 3H), 1.40-1.28 (m, 3H), 1.20-1.04 (m, 2H), 0.98 (d, J=6.6 Hz, 3H), 0.89-0.81 (m, 6H). $^{13}$C NMR (126 MHz, CDCl$_3$) δ 173.71, 151.55, 125.13, 43.86, 32.20, 31.21, 29.38, 19.83, 19.57, 12.18, 11.34. $[\alpha]^{23}_D$=+30.6 (c. 0.55, MeOH). HRMS (ES+) Calculated for C$_{11}$H$_{20}$O$_2$: 184.1463; Found: 184.1465.

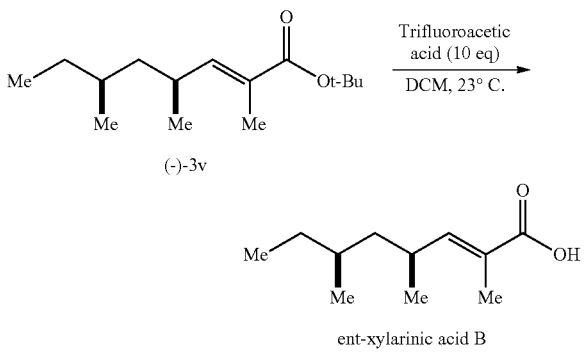

xylarinic acid B

Xylarinic acid B was prepared (colorless oil, 6.18 mg, 0.0335 mmol, 99% yield) using the same procedure as for 4-epi-xylarinic acid B.

$^1$H NMR (500 MHz, CDCl$_3$) δ 6.66 (dq, J=10.2, 1.4 Hz, 1H), 2.63 (tdd, J=13.4, 9.1, 5.7 Hz, 1H), 1.86 (d, J=1.4 Hz, 3H), 1.37 (ddd, J=13.5, 9.6, 4.2 Hz, 1H) 1.33-1.19 (m, 2H), 1.18-1.08 (m, 2H), 0.99 (d, J=6.6 Hz, 3H), 0.85 (t, J=7.2 Hz, 3H), 0.83 (d, J=6.3 Hz, 3H). $^{13}$C NMR (126 MHz, CDCl$_3$) δ 173.48, 151.27, 125.51, 44.21, 32.51, 31.28, 30.20, 20.55, 19.18, 12.27, 11.39. $[\alpha]^{23}_D$=−41.0 (c. 0.10, MeOH). HRMS (ES$^+$) Calculated for C$_{11}$H$_{20}$O$_2$: 184.1463; Found: 184.1465.

ent-xylarinic acid B ent-xylarinic acid B was prepared (colorless oil, 5.08 mg, 0.0276 mmol, quantitative yield) using the same procedure as for 4-epi-xylarinic acid B.

$^1$H NMR matches that of xylarinic acid B. $^{13}$C NMR matches that of xylarinic acid B. $[\alpha]^{23}_D$=+52.5 (c. 0.40, MeOH).

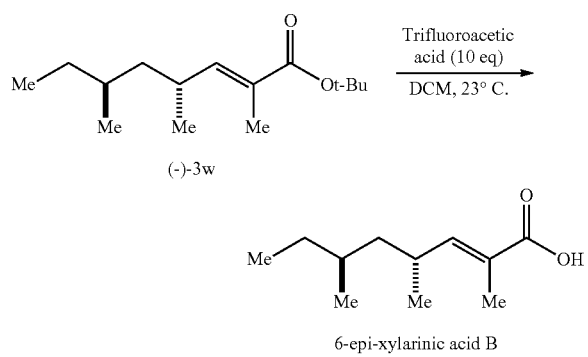

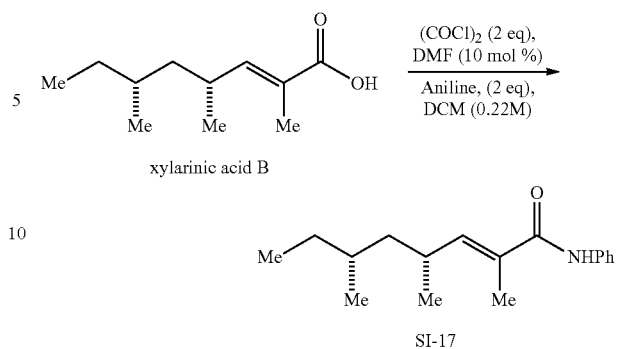

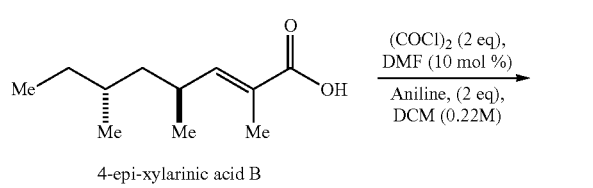

6-epi-xylarinic acid B was prepared (colorless oil, 5.04 mg, 0.0273 mmol, 92% yield) using the same procedure as for 4-epi-xylarinic acid B.

$^1$H NMR matches that of 4-epi-xylarinic acid B. $^{13}$C NMR matches that of 4-epi-xylarinic acid B. $[\alpha]^{23}_D = -26.3$ (c. 0.58, MeOH).

Phenyl Amide SI-17 was prepared from xylarinic acid B using the same procedure for phenyl amide SI-16. The d.r. of the crude phenyl amide was determined to be 98.0:2.0 (98.6% DS) by HPLC (OD-H chiral column, 1% IPA in hexanes, 2.0 mL/min, 254.4 nm absorbance). Major=15.2 minutes; minor=17.8 minutes. The second of the run reaction gave 98.5% DS.

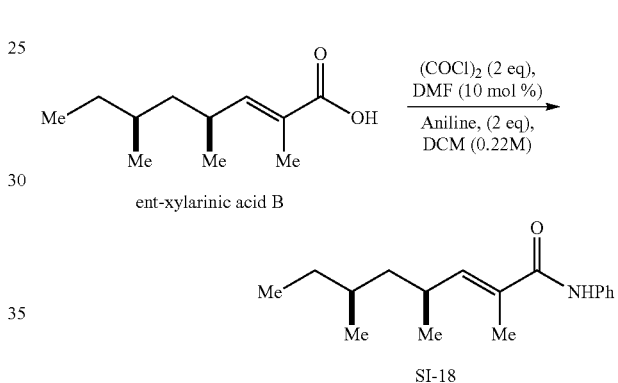

Phenyl Amide SI-18 was prepared from ent-xylarinic acid B using the same procedure for phenyl amide SI-16. The d.r. of the crude phenyl amide was determined to be 99.2:0.8 (98.6% DS) by HPLC (OD-H chiral column, 1% IPA in hexanes, 2.0 mL/min, 254.4 nm absorbance). Major=21.7 minutes; minor=17.8 minutes. The second of the run reaction gave 99.0% DS.

Phenyl Amide SI-16.

4-epi-xylarinic acid B (6.49 mg, 0.0352 mmol, 1.00 eq) was massed out in a stir bar-equipped 2 mL screw cap vial. Under nitrogen, anhydrous DCM (0.100 mL) was added, followed by a solution of oxalyl chloride in DCM (1.17 Molar, 60 µL, 0.0070 mmol, 2.0 eq) and a solution of DMF in DCM (1.3 Molar, 2.7 µL, 3.5 µmol, 10 mol %). The mixture was stirred under nitrogen for 20 minutes at room temperature, and then the volatiles (DCM and excess oxalyl chloride) were removed by a stream of nitrogen. Additional DCM (100 µL) was added, followed by a solution of aniline in DCM (0.548 Molar, 129 µL, 0.71 mmol, 2.0 eq). The reaction was stirred for 10 more minutes and then quenched by addition of 1M HCl (0.50 mL). The aqueous layer was extracted twice with DCM, and the extracts were passed through silica gel in a cotton-plugged glass pipet, rinsing with 10% EtOAc/hexanes. The filtrate was concentrated in vacuo. The d.r. of the crude phenyl amide was determined to be 99.6:0.4 (99.4% DS) by HPLC (OD-H chiral column, 1% IPA in hexanes, 2.0 mL/min, 254.4 nm absorbance). Major=17.7 minutes; minor=15.5 minutes. The second of the run reaction also gave 99.4% DS.

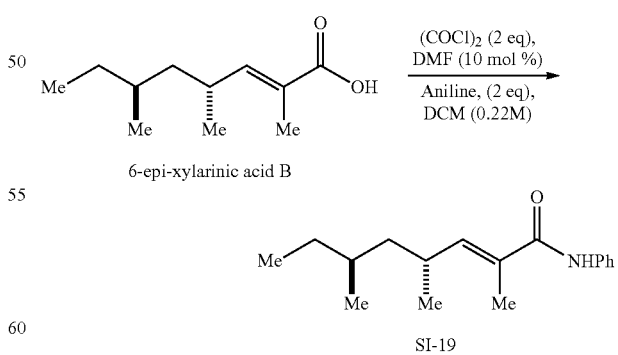

Phenyl Amide SI-19 was prepared from 6-epi-xylarinic acid B using the same procedure for phenyl amide SI-16. The d.r. of the crude phenyl amide was determined to be 99.4:0.6 (100% DS) by HPLC (OD-H chiral column, 1% IPA in hexanes, 2.0 mL/min, 254.4 nm absorbance).

Major=17.7 minutes; minor=21.9 minutes. The second of the run reaction gave 99.8% DS.

Example 6. Determination of the Stereochemical Outcome

A. Absolute Configuration of BIDA Boronates
Determining the Absolute Configuration of the C2 Stereocenter of 5a:

The absolute stereochemistry of the 2-butyl stereocenter was determined by x-ray crystallography of crystals grown by slow diffusion of Et$_2$O into an acetone solution of 5a in acetone at 23° C. using the known stereocenters of the cyclopentyl ring as reference.

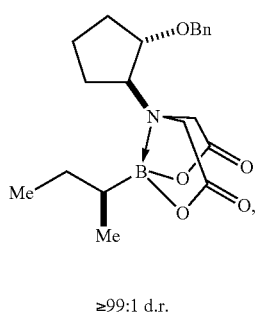

5a

≥99:1 d.r.

Determining the Absolute Configuration of the C2 Stereocenter of 7e:

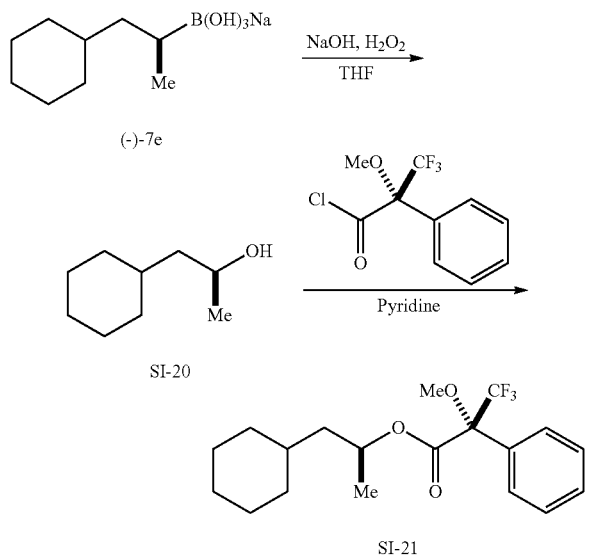

The trihydroxyborate salt (−)-7e (synthesized from 5e using general procedure B) was treated with 1M NaOH (5 equiv) followed by 30% H$_2$O$_2$ (3 eq) dropwise, causing the product to oil out. The mixture was stirred for 1 h at 23° C., then quenched with saturated aqueous sodium thiosulfate (10 equiv). The solution was extracted with DCM, dried with Na$_2$SO$_4$, and concentrated to give SI-20 an oil. The crude alcohol (4.0 mg, 0.028 mmol) thus obtained was dissolved in pyridine (50 µL, 0.056 Molar) and treated with (S)-(+)-α-methoxy-α-trifluoromethylphenylacetyl chloride (10 mg, 0.04 mmol, 1.4 eq) at 23° C. and stirred for three hours. 2M HCl was added and the mixture extracted with EtOAc twice. The organic phase was dried with Na$_2$SO$_4$ and concentrated under vacuum. The product SI-21 (7 mg, 0.020 mmol 70%) was obtained after purification by silica gel chromatography (2% EtOAc/hexanes). The $^1$H NMR and $^{13}$C NMR matched that of S4 independently synthesized from (S)-propylene oxide as described below, thus confirming that the configuration of the C2 stereocenter is (S).

Independent Synthesis of SI-20 and SI-21:

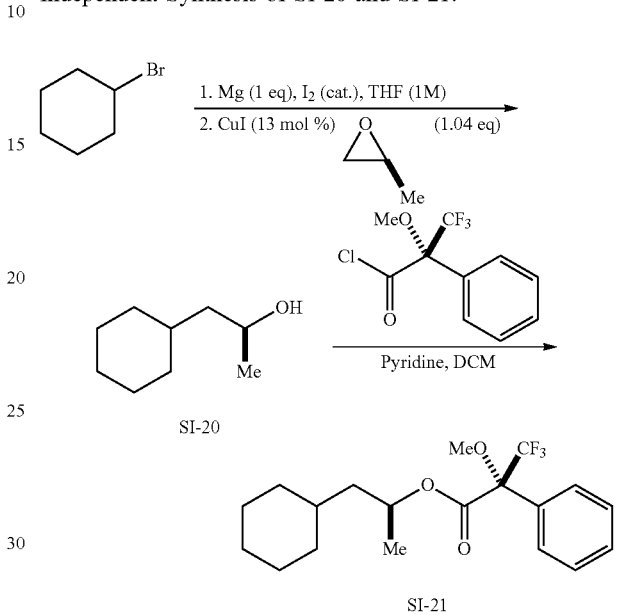

Following a literature procedure (Cannillo et al., *Chemistry (Weinheim an der Bergstrasse, Germany)* 2013, 19 (28), 9127), a 7-mL vial was charged with Mg turnings (24 mg, 1 mmol, 1 eq) and I$_2$ (1 mg, catalytic), followed by anhydrous THF (1 mL, 1 Molar) and bromocyclohexane (163 mg, 1 mmol, 1 eq) under nitrogen. The mixture was stirred at 50° C. until most of the Mg dissolved. CuI (24 mg, 0.13 mmol) was added. (S)-propylene oxide (Aldrich #540021, 73 µL, 1.04 mmol) was then added dropwise at 23° C. After stirring for 1 h, the black suspension was quenched with saturated aqueous NH$_4$Cl, and the mixture extracted with EtOAc. The organics were dried with Na$_2$SO$_4$, filtered and concentrated. The crude product was purified by silica gel column (10% to 15% EtOAc/hexanes) to give SI-20 (Buitrago et al., *Advanced Synthesis & Catalysis* 2012, 354, 217) as a colorless oil. Spectra matched those reported previously.

A 7 mL vial equipped with a stir bar was charged with SI-20 (15.2 mg, 0.107 mmol, 1.0 eq), DCM (0.5 mL, 0.21 Molar) and pyridine (30 µL, 0.37 mmol, 3.5 eq). (S)-(+)-α-Methoxy-α-trifluoromethylphenylacetyl chloride (20 µL, 0.107 mmol, 1.0 eq) was added at 23° C. and the reaction stirred at the same temperature overnight. The solvent was removed under a stream of nitrogen and the crude product loaded onto a silica gel column with 4% Et$_2$O/pentane. After silica gel purification (4% Et$_2$O/pentane), a white crystalline solid was obtained as the desired product SI-21 (34.9 mg, 0.0974 mmol, 91%).

SI-21: $^1$H NMR (500 MHz, CDCl$_3$) δ 7.67-7.50 (m, 2H), 7.45-7.31 (m, 3H), 5.26 (ddt, J=11.1, 4.9, 3.1 Hz, 1H), 3.58 (q, J=1.3 Hz, 3H), 1.78-1.47 (m, 7H), 1.38-1.23 (m, 4H), 1.16-0.99 (m, 4H), 0.91-0.72 (m, 2H). $^{13}$C NMR (126 MHz, CDCl$_3$) δ 166.09, 132.62, 129.42, 128.30, 127.12, 124.52, 122.22, 71.71, 55.40, 43.34, 33.61, 33.59, 32.47, 26.39, 26.14, 25.98, 20.44. $[\alpha]^{20}_D$=+68.4 (c 1.74, CHCl$_3$). HRMS (ES$^+$) Calculated for C$_{19}$H$_{25}$O$_3$F$_3$Na: 381.1653; Found: 381.1648.

Determining the Absolute Configuration of the C2 Stereocenter of 5f for Xylarinic Acid and 4-epi-xylarinic Acid:

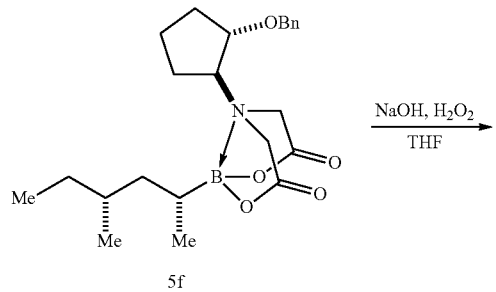

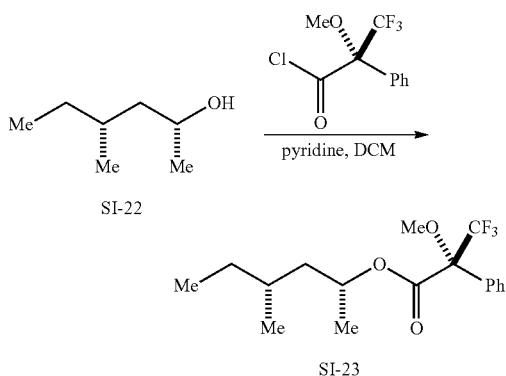

To a solution of BIDA boronate 5f (20 mg, 0.048 mmol) in THF (0.24 mL) was added 1N NaOH (0.24 mL, 0.24 mmol, 5.0 eq). The mixture was stirred for 5 minutes, and then 30% H$_2$O$_2$ (25 µL, 0.24 mmol, 5.0 eq) was added. The resulting mixture was stirred for 15 min, then diluted with Et$_2$O. The organic layer was washed with saturated aqueous Na$_2$S$_2$O$_3$, washed with brine, dried over Na$_2$SO$_4$, filtered, and concentrated under vacuum to give alcohol SI-22. The alcohol was dissolved in DCM (0.48 mL, 0.1 Molar), and then pyridine (12 µL, 0.144 mmol, 3.0 eq) and (S)-(+)-α-Methoxy-α-trifluoromethylphenylacetyl chloride (10 µL, 0.053 mmol, 1.1 eq) were added at 23° C. The reaction was stirred overnight and then quenched with the addition of H$_2$O. The product was extracted with DCM, dried over Na$_2$SO$_4$, filtered and concentrated. After silica gel purification (20% Et$_2$O/pentane), the Mosher ester SI-23, was obtained as a colorless oil. The NMR data matches that of SI-23 below, thus confirming that the C2 stereocenter is (R).

$^1$H NMR (500 MHz, CDCl$_3$) δ 7.59-7.48 (m, 2H), 7.40 (dd, J=5.0, 2.0 Hz, 3H), 5.35-5.15 (m, 1H), 3.55 (d, J=1.5 Hz, 3H), 1.75 (ddd, J=14.0, 9.3, 4.6 Hz, 1H), 1.39 (dt, J=12.9, 6.8 Hz, 1H), 1.36-1.09 (m, 5H), 0.89 (d, J=6.6 Hz, 3H), 0.85 (t, J=7.4 Hz, 3H). $^{13}$C NMR (126 MHz, CDCl$_3$) δ 166.21, 132.38, 129.46, 128.30, 127.35, 124.49, 72.41, 55.36, 42.69, 30.85, 29.73, 20.22, 18.82, 11.17. HRMS (ES$^+$) Calculated for C$_{17}$H$_{23}$O$_3$FNa: 355.1497; Found: 355.1497.

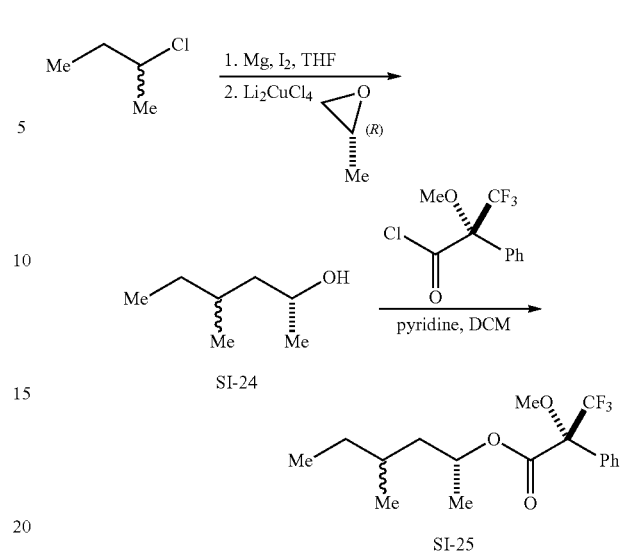

In an unoptimized procedure, 2-chlorobutane (0.635 mL, 6 mmol, 1.0 eq) was added to a mixture of Mg (146 mg, 6 mmol, 1.0 eq), I$_2$ (one crystal) and Et$_2$O (6 mL, 1.0 Molar) dropwise at 23° C. The reaction was stirred for 2.5 hours after the addition. The solution of the Grignard reagent was then added dropwise to a solution of (R)-propylene oxide (0.14 mL, 2 mmol, 0.33 eq) and Li$_2$CuCl$_4$ (1M in THF, 2 mL, 0.2 mmol, 0.033 eq) in THF (6 mL) at −50° C. The reaction was warmed to room temperature and stirred overnight, then cooled to 0° C. Saturated aqueous NH$_4$Cl (12 mL) was added, and the mixture was stirred until most of the brown solids dissolved. The mixture was transferred to a separatory funnel with H$_2$O and Et$_2$O (10 mL). After mixing and phase separation, the aqueous layer was extracted with Et$_2$O (10 mL). The combined organics were washed with brine, dried over MgSO$_4$, filtered, and concentrated. The residue was purified by silica gel chromatography (30 to 40% Et$_2$O/pentane) to give alcohol SI-24 (130 mg, 37%). The Mosher ester SI-25, which is a mixture of diastereomers with a stereodefined C2 stereocenter was synthesized from SI-24 using the procedure described above for the synthesis SI-23 from SI-22.

$^1$H NMR (500 MHz, CDCl$_3$) δ 7.61-7.45 (m, 4H), 7.47-7.33 (m, 6H), 5.36-5.14 (m, 2H), 3.55 (dq, J=2.5, 1.3 Hz, 6H), 1.75 (ddd, J=14.0, 9.3, 4.6 Hz, 1H), 1.62-1.53 (m, 1H), 1.52-1.36 (m, 4H), 1.35-1.08 (m, 11H), 0.93-0.80 (m, 13H). $^{13}$C NMR (126 MHz, CDCl$_3$) δ 166.22, 166.13, 132.40, 129.48, 128.33, 127.36, 124.50, 72.67, 72.42, 55.36, 42.70, 42.58, 30.94, 30.86, 29.74, 28.95, 20.22, 19.67, 19.20, 18.83, 11.18, 11.07.

B. Absolute Configuration of Coupled Products

To determine the absolute stereochemistry of (+)-3a obtained from the coupling reaction of (S)-1a and 2a, (S)-3a was independently synthesized from (S)-3-phenylbutyric acid:

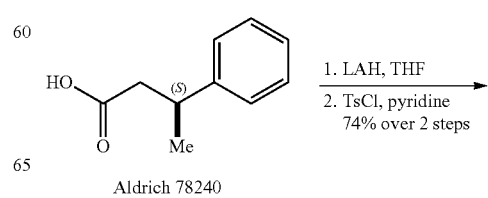

Aldrich 78240

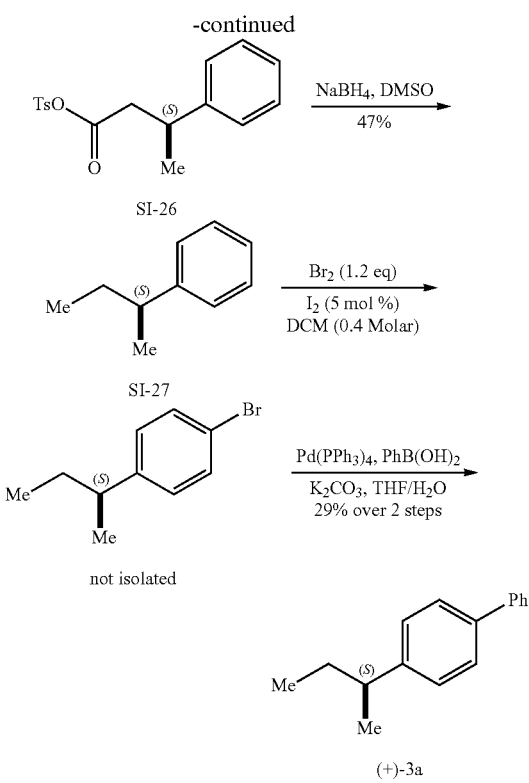

(S)-3-phenylbutyl 4-methylbenzenesulfonate SI-26

In a glovebox, lithium aluminum hydride powder (88 mg, 2.2 mmol) was added to a dry 3-neck flask. This was fitted with a reflux condenser and 2 septa. In a fume hood, dry THF (10 mL) was added and the mixture was stirred at 23° C. (+)-(S)-3-phenylbutyric acid (Sigma Aldrich 78240, Lot # BCBF9385V), was added dropwise as a solution in THF (3.5 mL) and the mixture was stirred at reflux for 12 hours. TLC (3:1 Hex/EtOAc, KMnO$_4$) showed complete conversion. The reaction was quenched with 1M aqueous Rochelle salt and extracted three times with DCM. The combined DCM phase was dried over sodium sulfate and concentrated under vacuum. The crude material (310 mg) was used directly in the next step.

The crude alcohol (310 mg) was combined in a 7 mL vial with distilled pyridine (1.0 mL) and toluenesulfonyl chloride (0.419 g, 2.2 mmol) that had been recrystallized from hot hexanes. The reaction was capped and stirred at 23° C. until complete conversion of the alcohol as seen by TLC. At 5 h, 1M HCl was added and the mixture was extracted three times with Et$_2$O. The combined Et$_2$O phase was washed with 1M HCl, then H$_2$O, then saturated NaHCO$_3$. The solution was dried over sodium sulfate and concentrated under vacuum. The crude was purified by silica column using a gradient of 5% to 15% EtOAc in hexanes, giving the product SI-26 as a colorless oil (0.460 g, 1.51 mmol, 74% from (S)-3-phenylbutyric acid).

$^1$H NMR (400 MHz, CDCl$_3$) δ 7.74 (d, J=8.3 Hz, 2H), 7.32 (d, J=8.0 Hz, 2H), 7.25-7.13 (m, 3H), 7.04 (d, J=7.1 Hz, 2H), 3.97 (dt, J=9.8, 5.9 Hz, 1H), 3.82 (ddd, J=9.8, 7.9, 5.8 Hz, 1H), 2.87-2.75 (m, 1H), 2.45 (s, 2H), 2.01-1.79 (m, 2H), 1.21 (d, J=7.0 Hz, 3H). $^{13}$C NMR (101 MHz, CDCl$_3$) δ 145.46, 144.78, 133.16, 129.93, 128.66, 128.02, 127.01, 126.47, 68.98, 37.17, 35.97, 22.15, 21.79. [α]$^{20}_D$=+97.1 (c 1.0, CDCl$_3$). HRMS (EI$^+$) Calculated for C$_{17}$H$_{20}$O$_3$S: 304.1133; Found: 304.1132.

(S)-sec-butylbenzene SI-27

To a 20 mL vial with a septum cap and stir bar were added (S)-3-phenylbutyl 4-methylbenzenesulfonate (0.450 g, 1.45 mmol, 1.00 eq), followed by DMSO (8 mL) and NaBH$_4$ (0.281 g, 7.43 mmol, 5.1 eq). The headspace was purged with nitrogen the reaction was stirred at 70° C., during which time the reaction became homogeneous. Monitoring of the reaction by TLC (4:1 Hex/EtOAc, KMnO$_4$) showed complete conversion of the substrate at 20 hours. H$_2$O (8 mL) was added and the solution was extracted four times with pentane. The combined pentane phase was washed twice with H$_2$O, then with 3% H$_2$O$_2$, and again with H$_2$O. The solution was dried over sodium sulfate and concentrated under light vacuum to give SI-27 as an oil (0.128 g, 0.770 mmol, 47% yield). This was used in the next step without purification. The spectral properties of sec-butylbenzene were identical to those reported previously (Duan et al., *Organic Letters* 2016, 18 (16), 4012). Comparison of the optical rotation to the literature value showed a high level of enantiopurity.

[α]$^{20}_D$=+27.4 (c 1.0, CHCl$_3$). Lit. +25.0.

(S)-4-(sec-butyl)-1,1'-biphenyl (S)-3a

Elemental bromine (12.4 μl, 38.5 mg, 0.241 mmol) was added dropwise to a solution of sec-butylbenzene SI-27 (27 mg, 0.16 mmol, 1.0 eq) and iodine (2.5 mg, 0.010 mmol, 6 mol %) in DCM (0.5 mL, 0.3 Molar) in an ice bath under nitrogen. The reaction was stirred at 23° C. for 2 hours. The conversion could not be determined by TLC (100% pentane). The reaction was quenched with 0.5M KOH and extracted twice with DCM. The DCM phase was dried over sodium sulfate and concentrated under vacuum. This material was filtered through a silica plug with pentane and concentrated to afford an oil (23 mg). $^1$H-NMR shows a 1:1 ratio of starting material (0.061 mmol, 10.1 mg) to product (0.061 mmol, 12.9 mg). This mixture was taken on to the coupling reaction without purification.

To the crude product from the above reaction in a 7 mL vial in a glove box were added Pd(PPh$_3$)$_4$ (1.7 mg, 1.5 μmol, 2.5 mol %), phenylboronic acid (12.1 mg, 0.10 mmol, 1.6 eq), K$_2$CO$_3$ (0.236 g, 1.9 mmol, 32 eq), and THF (0.8 mL, 0.08 Molar). In a fume hood, H$_2$O (0.57 mL, 0.11 Molar) was added. The headspace was purged with nitrogen, capped and stirred 10 hours at 75° C. TLC (100% pentane, UV) showed product. The THF was removed under vacuum. The solution was then extracted three times with pentane. The pentane phase was dried over sodium sulfate, concentrated under vacuum, and purified by silica column with 100% pentane, giving (S)-3a as a colorless oil (12.3 mg, 0.0507 mmol, 32% yield).

$^1$H NMR (500 MHz, CDCl$_3$) δ 7.61 (d, J=7.1 Hz, 2H), 7.55 (d, J=8.2 Hz, 2H), 7.45 (t, J=7.7 Hz, 2H), 7.34 (t, J=7.4 Hz, 1H), 7.28 (d, J=8.3 Hz, 2H), 2.66 (h, J=7.0 Hz, 1H), 1.65 (pd, J=7.3, 2.2 Hz, 2H), 1.30 (d, J=7.0 Hz, 3H), 0.88 (t, J=7.4 Hz, 3H). $^{13}$C NMR (101 MHz, CDCl$_3$) δ 146.95, 141.30, 138.81, 128.81, 127.60, 127.12, 127.11, 127.06, 41.48, 31.32, 21.98, 12.46.

The product (S)-3a had an e.r. of >99.5:0.5 as determined using a Chiralcel OD-H column of 4.6 mm×250 mm, hexanes, 2.0 mL/min., 210 nm absorbance. Major: 5.7, Minor: 9.3. The retention time of the (S)-3a obtained here matches that of the coupling product (+)-3a, thus confirming that the coupling reaction went with stereoretention.

C. Crystal Structures.

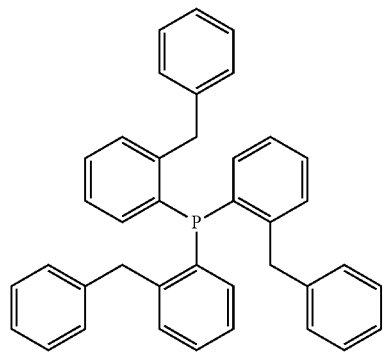

L4

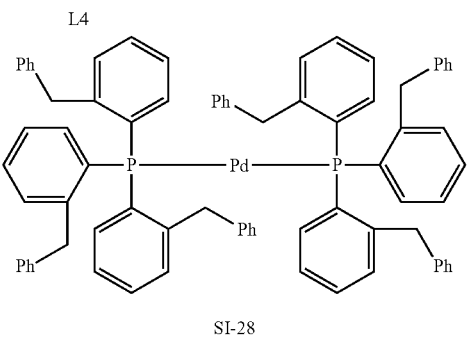

SI-28

Bis[tris(2-benzyl-phenyl)phosphine] SI-28

A solution of P(2-benzyl-phenyl)$_3$ (0.533 g, 1.00 mmol, 1.00 eq) and Pd$_2$dba$_3$ (0.229 g, 0.25 mmol, 0.50 eq) was prepared in anhydrous DMF (40 mL, 0.025 Molar) under nitrogen. The reaction was stirred for 10 hours at room temperature, during which time a yellow-green precipitate formed and the dark red color of Pd$_2$dba$_3$ faded. The DMF was filtered by syringe, requiring a long time to carry out. The filtered solid was washed with Et$_2$O (5 mL), and the color began to change. The solid was dissolved in THF, causing a color change to dark orange. The solution was drawn portionwise into a 20 mL syringe. A disc-shaped filter was fitted to the syringe, and then it was equipped with a needle. After filtration, solution was recrystallized from DCM (20 mL) and pentane (60 mL) with overnight stirring at 0° C. Crystals of SI-28 were collected by filtration (0.340 g, 0.290 mmol, 58% yield).

X-ray crystals were prepared by dissolving the product in benzene with slow diffusion into Et$_2$O.

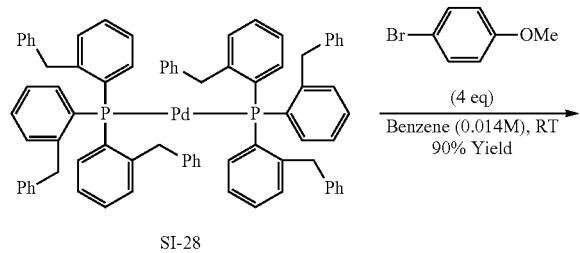

SI-28

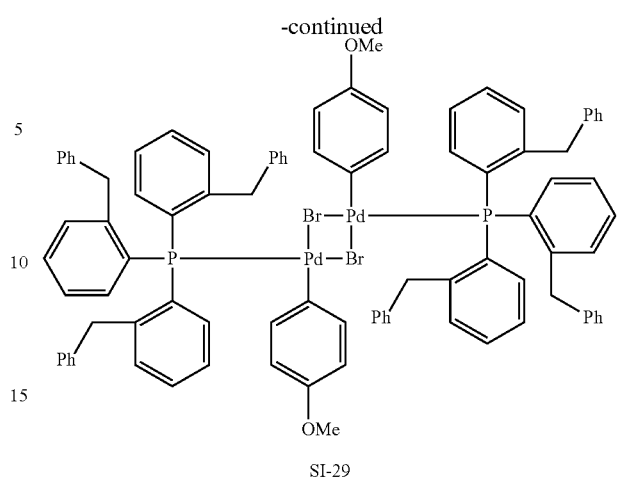

SI-29

{[(2-Benzyl-phenyl)$_3$P]Pd(4-OMe-phenyl)(Br)}$_2$
SI-29

Bis[tris(2-benzyl-phenyl)phosphine]Pd(0) SI-28 (50 mg, 0.0427 mmol, 1.00 eq) was combined with 4-bromoanisole (32 mg, 0.171 mmol, 4.0 eq). Dry benzene (3.0 mL, 0.014 Molar) was added under a nitrogen stream, and a solid cap was fitted on the vial. The yellow suspension was stirred for 24 hours at room temperature. Solvent was removed by rotary evaporation, and then the product was washed with Et$_2$O (2×2.5 mL) using a centrifuge.

X-ray crystals were obtained by dissolving the dimeric complex in a minimal sufficient amount of DCM. This solution was passed through a syringe filter into a 7 mL vial containing Et$_2$O (approximately 6 mL) using a needle to slowly load the solution into a bottom layer. The vial was filled to the top with Et$_2$O and fitted with a solid screw cap, allowing crystals to form by slow diffusion.

Example 6. Assay to Test for Racemization of Boronic Acids

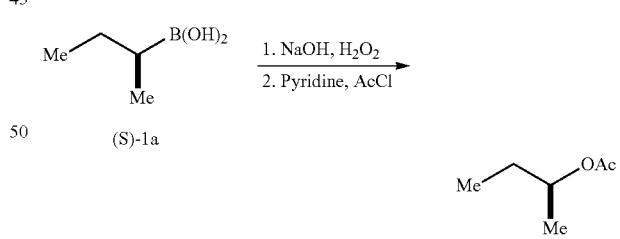

A solution of 1 mmol of (S)-1a, produced by hydrolysis of BIDA boronate 5a of ≥99:1 d.r. following general procedures B and C, was diluted to 0.5 Molar in dioxane in a 7 mL vial in an ice bath. To this was added 30% H$_2$O$_2$ (0.227 g, 2.0 mmol, 2.0 eq) and 1 Molar NaOH (2.0 mL, 2.0 mmol, 2.0 eq). The mixture was stirred until complete conversion of the boronic acid was seen by TLC (1:1 Hex/EtOAc, KMnO$_4$). 1 Molar HCl (5 mL) and Et$_2$O (5 mL) were then added, and the organic layer was washed with saturated sodium bisulfate, H$_2$O, and brine. It was dried with sodium sulfate and concentrated to a 2 mL volume (a small aliquot was removed, the Et$_2$O was removed under an air stream, and the sample was analyzed by $^1$H-NMR, showing the presence of 2-butanol). To this solution was then added pyridine (0.242 mL, 0.238 g, 3.00 mmol, 3.00 eq) followed by the dropwise addition of acetyl chloride (0.213 mL, 0.234 g, 3.00 mmol, 3.00 eq). The heterogeneous mixture was capped and stirred 8 hours at 23° C. The mixture was washed three times with 1 Molar HCl, once with saturated NaHCO$_3$, and once with brine. The solvent was removed under light vacuum to yield 25 mg of 2-butylacetate (confirmed by 1H NMR) as a colorless oil. This 2-butylacetate was determined by chiral GC to be of ≥99:1 e.r. (Agilent chiral G-TA column was used, with 0.8 mL/minute gas flow, 24° C. to 55° C. at 1° C./minute. Major: 20.6, Minor: 22.1), indicating that no racemization took place during the synthesis of (S)-1a.

Stability Tests.

The long-term bench top stability of these compounds was determined as follows. Two 2 mL Teflon-lined screw-cap vials were each filled with 10 mg of MIDA boronate (±)-6a. Similarly, two of these vials were filled with 15 mg of BIDA boronate 5a of 99:1 dr and two were filled with 10 mg of trihydroxyborate salt (±)-7a. 0.5 mL of a solution of 1.15M (±)-1a in dioxane, prepared by general procedure C, was added to one vial. Each compound was initially quantified by adding 0.5 mL of DMSO-d$_6$ with 0.10 Molar 1,4-dimethoxybenzene standard to one of the vials containing (±)-6a, 5a or (±)-7a. The solutions were transferred to NMR tubes. 50 μl of the solution of (±)-1a was also added to an NMR tube with 0.5 mL of DMSO-d$_6$ with 0.1 Molar 1,4-dimethoxybenzene standard. Mmol of compound was determined by $^1$H-NMR integration with a relaxation delay of 10 seconds. The remaining vials were tightly capped under air and stored on the bench top for 4 months. Then, the NMR quantification was repeated. All three solid compounds showed no decomposition. The concentration of (±)-1a decreased by <10% (1.05M), with small amounts of decomposition products present in the spectrum.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A phosphine compound of Formula I:

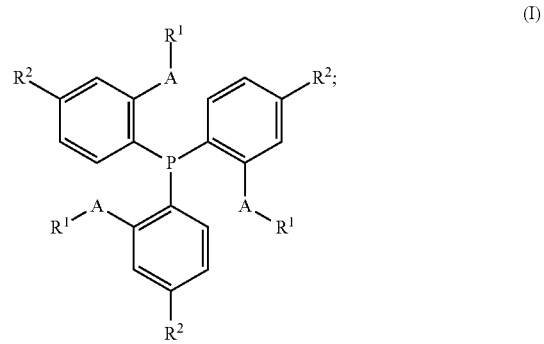

(I)

wherein

A is CH$_2$, C=O, or NR$^4$;

R$^1$ is aryl, heteroaryl, tert-butyl, cycloalkyl, or heterocycloalkyl, wherein aryl, heteroaryl, cycloalkyl and heterocycloalkyl are optionally substituted;

R$^2$ is H, (C$_1$-C$_8$)alkyl, (C$_1$-C$_8$)alkoxy, N(R$^4$)$_2$, or an electron withdrawing group; and each R$^4$ is independently H or (C$_1$-C$_8$)alkyl; wherein the electron withdrawing group is halo, trifluorom-

| Compound | 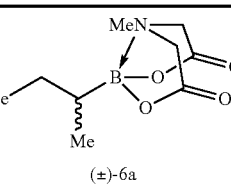 (±)-6a | 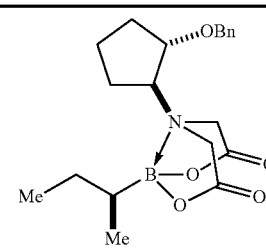 5a, ≥ 99:1 d.r. | 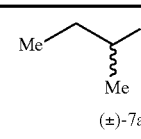 (±)-7a | 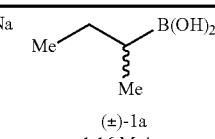 (±)-1a 1.16 Molar in dioxane |
|---|---|---|---|---|
| Result at 4 months | No decomposition | No decomposition | No decomposition | Concentration decreased to 1.06 Molar |

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

ethyl, pentafluoroethyl, trifluoromethoxy, nitrile, nitro, CO$_2$R$^4$, C(O)N(R$^4$)$_2$, SO$_2$R$^4$, SO$_2$N(R$^4$)$_2$, or P(O)[N(R$^4$)$_2$]$_2$.

2. The phosphine compound of claim 1 wherein R$^1$ is aryl or (C$_3$-C$_8$)cycloalkyl, wherein aryl and (C$_3$-C$_8$)cycloalkyl are optionally monosubstituted or disubstituted.

3. A The phosphine compound of Formula II:

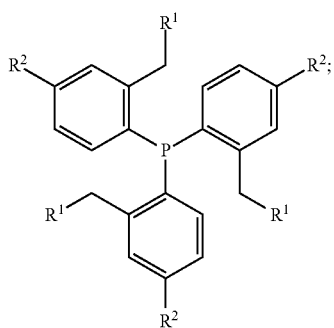
(II)

wherein
$R^1$ is phenyl or $(C_3-C_6)$cycloalkyl, wherein phenyl and $(C_3-C_6)$cycloalkyl are optionally monosubstituted or disubstituted; and
$R^2$ is H, $(C_1-C_5)$alkyl, $(C_1-C_5)$alkoxy, $N(R^4)_2$, halo, trifluoromethyl, pentafluoroethyl, trifluoromethoxy, nitrile, nitro, $CO_2R^4$, or $C(O)N(R^4)_2$; and each $R^A$ is independently H or $(C_1-C_8)$alkyl.

4. The phosphine compound of claim 3 wherein $R^2$ is H, halo, trifluoromethyl, pentafluoroethyl, trifluoromethoxy, nitrile, nitro, $CO_2R^4$, or $C(O)N(R^4)_2$.

5. The phosphine compound of claim 3 wherein the phosphine compound is phosphine compound of Formula III:

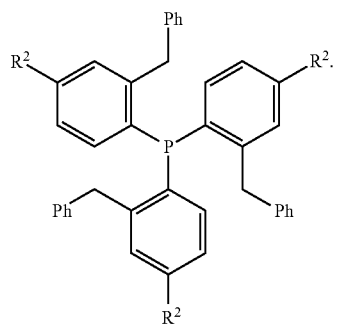
(III)

6. The phosphine compound of claim 5 wherein $R^2$ is H, methyl ethyl, methoxy, ethoxy, dimethylamine, diethylamine, halo, trifluoromethyl, pentafluoroethyl, trifluoromethoxy, nitrile, nitro, $CO_2R^4$, or $C(O)N(R^4)_2$.

7. The phosphine compound of claim 3 wherein the phosphine compound is one of phosphine compounds IIIA-IIIC:

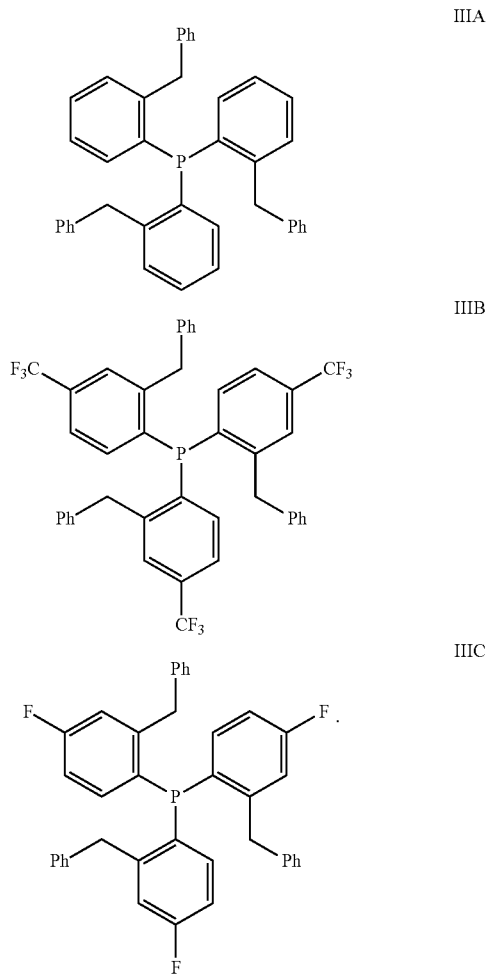

* * * * *